United States Patent
Basu et al.

(10) Patent No.: US 11,643,651 B2
(45) Date of Patent: May 9, 2023

(54) COMPOSITIONS AND METHODS FOR PROTEIN PRODUCTION

(71) Applicant: Syngenta Participations AG, Basel (CH)

(72) Inventors: Shib Sankar Basu, Durham, NC (US); Kristen Kamerath Dang, Seattle, WA (US); Thomas Z. McNeill, Frisco, TX (US); Kasimalai Azhakanandam, Research Triangle Park, NC (US); Sheng Guo, Jiangsu Province (CN)

(73) Assignee: Syngenta Participations AG, Basel (CH)

( * ) Notice: Subject to any disclaimer, the term of this patent is extended or adjusted under 35 U.S.C. 154(b) by 827 days.

(21) Appl. No.: 15/433,396

(22) Filed: Feb. 15, 2017

(65) Prior Publication Data

US 2017/0226504 A1    Aug. 10, 2017

Related U.S. Application Data

(60) Division of application No. 14/593,707, filed on Jan. 9, 2015, now Pat. No. 9,605,258, which is a division
(Continued)

(51) Int. Cl.
*G01N 33/48* (2006.01)
*G01N 33/50* (2006.01)
*C12N 15/10* (2006.01)

(52) U.S. Cl.
CPC ..... *C12N 15/1089* (2013.01); *C12N 15/1034* (2013.01)

(58) Field of Classification Search
CPC .............. C12N 15/1089; C12N 15/1034
See application file for complete search history.

(56) References Cited

U.S. PATENT DOCUMENTS

| 6,366,860 B1 | 4/2002 | Rozzell, Jr. et al. |
| 6,733,994 B2 | 5/2004 | Weiner et al. |

(Continued)

FOREIGN PATENT DOCUMENTS

| WO | 0168835 A2 | 9/2001 |
| WO | WO 01/68835 A2 | 9/2001 |

(Continued)

OTHER PUBLICATIONS

Takashi Fujita, et al., "Structure of the human interleukin 2 gene", *Proc. Natl. Acad. Sci. USA*, vol. 80, pp. 7437-7441, Dec. 1983.

(Continued)

*Primary Examiner* — Russell S Negin
(74) *Attorney, Agent, or Firm* — Dale Skalla

(57) ABSTRACT

The present invention provides a method of selecting a mRNA for production of a polypeptide of interest comprising: a) producing an array of individual mRNA sequences comprising different nucleotide sequences encoding the polypeptide of interest; b) determining one or more or two or more of the following parameters for each individual mRNA sequence of (a): (i) minimum free energy (MFE) RNA secondary structure; (ii) ensemble free energy (EFE); (iii) frequency of the minimum free energy (FMFE) RNA secondary structure in a thermodynamic ensemble; and (iv) ensemble diversity (ED); c) ranking the individual mRNA sequences of the array according the parameters determined in step (b); and d) selecting a mRNA sequence from the ranked array of step (c), wherein the selected mRNA produces the polypeptide of interest. The present invention further provides a method of selecting a mRNA for enhanced and reduced production of a polypeptide of interest.

13 Claims, 6 Drawing Sheets

Specification includes a Sequence Listing.

Related U.S. Application Data of application No. 13/708,479, filed on Dec. 7, 2012, now Pat. No. 9,334,494, which is a continuation-in-part of application No. PCT/US2011/039701, filed on Jun. 9, 2011.

(60) Provisional application No. 61/353,879, filed on Jun. 11, 2010.

(56) References Cited

U.S. PATENT DOCUMENTS

| | | |
|---|---|---|
| 6,818,752 B2 | 11/2004 | Rozzell, Jr. et al. |
| 2004/0002083 A1 | 1/2004 | Ding et al. |
| 2005/0196774 A1 | 9/2005 | Rozzell, Jr. et al. |
| 2006/0024679 A1 | 2/2006 | Voges et al. |
| 2008/0268503 A1 | 10/2008 | Samaddar et al. |
| 2011/0082673 A1 | 4/2011 | Warshel et al. |
| 2013/0084641 A1 | 4/2013 | Basu et al. |

FOREIGN PATENT DOCUMENTS

| | | |
|---|---|---|
| WO | 0229088 A2 | 4/2002 |
| WO | WO 02/29088 A2 | 4/2002 |

OTHER PUBLICATIONS

D.R. Gallie, et al., "A translation enhancer derived from tobacco mosaic virus is functionally equivalent to a Shine-Dalgarno sequence", Proc. Natl. Acad. Sci. USA, vol. 86, pp. 129-132, Jan. 1989.
GenBank AAB46883.1, interleukin-2 [Homo sapiens], http://www.ncbi.nlm.nih.gov/protein/1836111, printed from Internet Mar. 12, 2015.
Lei Zhang, et al., "Alteration in the IL-2 signal peptide affects secretion of proteins invitro and in vivo", J Gene Med 2005; 7: pp. 354-365.
Devos et al., Molecular cloning of human Interleukin 2 cDNA and its expression in E. coli, Nucleic Acids Research, vol. 11, No. 13, 1983. pp. 4307-4323.
Lu et al., Efficient siRNA selection using hybridization thermodynamics, Nucleic Acids Research, vol. 36, No. 2, 2008, pp. 640-647.
Melnikov et al., One core, two shells: bacterial and eukaryotic ribosomes, Nature Structural & Molecular Biology, vol. 19, Nos. Jun. 2012, pp. 560-567.
Taylor, Interpretation of the Correlation Coefficient: A Basic Review, JDMS, 1, Jan./Feb. 1990, pp. 35-39.
Extended European Search Report in corresponding European Application No. 11793130.3; dated Nov. 22, 2013; 7 pp.
Jackson et al., "The mechanism of eukaryotic translation initiation and principles of its regulation" Nature Reviews Molecular Cell Biology 10:113-127 (2010).
Zuker, "Calculating nucleic acid secondary structure" Current Opinion in Structural Biology 10:303-310 (2000).
Hofacker et al. "Fast Folding and Comparison of RNA Secondary Structures", Monatshefte fur Chemie Chemical Monthly, 125, 167-188, (1994).
Waldispuhl et al. "RNAmutants: a web server to explode the mutational landscape of RNA secondary structures", Nucleic Acids Research, Jun. 16, 2009, vol. 37, Web Server Issue, W281-286.
International Search Report and Written Opinion Corresponding to International Application No. PCT/US 11/ 39701; dated Apr. 16, 2012; 18 Pages.
Bernhart S.H et al., "Partition function and base pairing probabilities of RNA heterodimers", Algorithms for Molecular Biology, 2006, 1:3.
Dirks, R.M. et al., "A Partition Function Algorithm for Nucleic Acid Secondary Structure Including Pseudoknots", J Comput Chem, 24: 1664-1677, 2003.
Gu W. et al., "A Universal Trend of Reduced mRNA Stability near the Translation-Initiation Site in Prokaryotes and Eukaryotes", PLoS Computational Biology, Feb. 2010, vol. 6, Issue 2, e1000664.
Kudla G. et al., "Coding-Sequence Determinants of Gene Expression in Escherichia coli", Science, vol. 324, Apr. 10, 2009, 255-258.
Mathews D.H. et al., "Expanded Sequence Dependence of Thermodynamic Parameters Improves Prediction of RNA Secondary Structure", J. Mol. Biol., 1999, 288, 911-940.
McCaskill J.S., "The Equilibrium Partition Function and Base Pair Binding Probabilities for RNA Secondary Structure", Biopolymers, vol. 29, 1105-1119, 1990.
Wuchty S. et al., "Complete Suboptimal Folding of RNA and the Stability of Secondary Structures", Biopolymers, vol. 49, 145-165, 1999.
Zuker M. et al., "Optimal computer folding of large RNA sequences using thermodynamics and auxiliary information", Nucleic Acids Research, 9(1):133-148, 1981.
Notification of Transmittal of International Preliminary Report on Patentability in corresponding International Application No. PCT/US2011/039701, dated Dec. 27, 2012 (12 pages).
Zuker, Calculating nucleic acid secondary structure, Current opinion in Structural Biology, 2000, 10, 303-310.
Extended European Search Report in corresponding European Application No. 11793130.3; dated Nov. 22, 2013; 7 pages.
Jackson et al., The mechanism of eukaryotic translation initiation and principles of its regulation, Nature Reviews Molecular Cell Biology, 10: 113-137, 2010.
Kozak, Initiation of translation in prokaryotes and eukaryotes, Gene, 234, 187-208, 1999.
Shine et al., Determinant of cistron specificity in bacterial ribosomes, Nature, 254, 34-38, 1975.
Bernhart, Partition function and base pairing probabilities of RNA heterodimers, Algorithms for Molecular Biology, 2006, 1, 3.
Dirks et al., A partition function algorithm for nucleic acid secondary structure including pseudoknots, J. Comput Chem, 2003, 24, 1664-1677.
Gu et al., A universal trend of reduced mRNA stability near the translation-initiation site in prokaryotes and eukaryotes, PLoS Computational Biology, Feb. 2010, 6, 2, e1000664.
Kudla et al., Coding-sequence determinants of gene expression in Escherichia coli, Science, 2009, 324, 255-258.
Mathews et al., Expanded sequence dependence of thermodynamic parameters improves prediction of RNA secondary structure, J. Mol. Biol., 1999, 288, 911-940.
McCaskill, The equilibrium partition function and base pair binding probabilities for RNA secondary structure, Biopolymers, 1990, 29, 1105-1119.
Wuchty et al., Complete suboptimal folding of RNA and the stability of secondary structures, Biopolymers, 1999, 49, 145-165.
Zuker et al., Optimal computer folding of large RNA sequences using thermodynamics and auxiliary information, Nucleic Acids Research, 1981, 9, 1, 133-148.
Ding, Statistical and bayesian approaches to RNA secondary structure prediction, RNA, 2006, 12, 323-331.
Freyhult et al., A comparison of RNA folding measures, BMC Bioinformatics, Oct. 2005, 6, 241.
Hofacker et al., Fast folding and comparison of RNA secondary structures, Monatshefte fur Chemie Chemical Monthly, 1994, 125, 167-188.
Waldispuhl et al., RNA mutants: a web server to explode the mutational landscape of RNA secondary structures, Nucleic Acids Research, Jun. 16, 2009, 37, Web Server Issue, W281-W286.
International Search Report and Written Opinion corresponding to International Application No. PCT/US11/39701, dated Apr. 16, 2012.
Notification of Transmittal of International Preliminary Report on Patentability in corresponding to International Application No. PCT/US11/39701, dated Dec. 27, 2012.
Devos et al., Molecular cloning of human interleukin 2 cDNA and its expression in E. coli, Nucleic Acids Research, 11, 13, 1983, 4307-4823.
Lu et al., Efficient siRNA selection using hybridization thermodynamics, Nucleic Acids Research, 36, 2, 2008, 640-647.
Melnikov et al., One core, two shells: bacterial and eukaryotic ribosomes, Nature Structural & Molecular Biology, 19, 6, Jun. 2012, 560-567.

(56) References Cited

OTHER PUBLICATIONS

Taylor, Interpretation of the Correlation Coefficient: A Basic Review, JDMS, 1, Jan./Feb. 1990, 35-39.

Fujita et al., Structure of the human interleukin 2 gene, Proc. Natl. Acad. Sci., USA, Dec. 1983, 80, 7437-7441.

Gallie et al., A translation enhancer derived from tobacco mosaic virus is functionally equivalent to Shine-Dalgarno sequence, Proc. Natl. Acad. Sci., USA, Jan. 1989, 86, 129-132.

GenBank AAB46883.1, interleukin-2[*Homo sapiens*}, http://www.ncbi.nim.nih.gov/protein/1836111, printed from Internet Mar. 12, 2015.

Lei Zhang et al., Alteration in the IL-2 signal peptide affects secretion of proteins in vitro and in vivo, J. Gene Med, 2005, 7, 354-365.

US 11,643,651 B2

COMPOSITIONS AND METHODS FOR PROTEIN PRODUCTION

STATEMENT OF PRIORITY

This application is a divisional application of U.S. patent application Ser. No. 14/593,707, filed Jan. 9, 2015, now U.S. Pat. No. 9,605,258, which is a divisional application of U.S. patent application Ser. No. 13/708,479, filed Jun. 9, 2011, now U.S. Pat. No. 9,334,494, which is a continuation-in-part of PCT/US2011/39701, which claims the benefit, under 35 U.S.C. § 119(e), of U.S. Provisional Application No. 61/353,879; filed Jun. 11, 2010, the entire contents of which are incorporated by reference herein.

FIELD OF THE INVENTION

The present invention provides methods related generally to the field of protein production. Specifically, the present invention provides methods for selecting a mRNA for production of a polypeptide of interest.

BACKGROUND OF THE INVENTION

Many factors influence protein production including gene copy number, gene location, transcription and translation efficiency, transcription factors and mRNA stability. Efforts have focused on the development of technology to manipulate these and other factors in order to increase protein production. Thus, for example, numerous reports of increased protein expression through altered codon usage are found in the literature, making this synthetic gene approach a common strategy for protein expression. Despite the reported advantages, often experimental observations underscore the importance of other factors in determining the efficiency of heterologous protein production. Thus, as yet no method has been devised that provides the level of predictability in protein production that is needed.

Accordingly, the present invention addresses the previous shortcomings of the art by providing methods for selecting a mRNA producing a protein of interest at a desired amount.

SUMMARY OF THE INVENTION

A first aspect of the present invention provides a method of selecting a mRNA for production of a polypeptide of interest, the method comprising: a) producing an array of individual mRNA sequences comprising different nucleotide sequences encoding the polypeptide of interest; b) determining one or more of the following parameters for each individual mRNA sequence of (a): (i) ensemble free energy (EFE); (ii) frequency of the minimum free energy (FMFE) RNA secondary structure in a thermodynamic ensemble; and (iii) ensemble diversity (ED); c) ranking the individual mRNA sequences of the array according to the parameters determined in step (b); and d) selecting a mRNA sequence from the ranked array of step (c), wherein the selected mRNA produces the polypeptide of interest.

A further aspect of the invention provides a method of selecting a mRNA for production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

In other aspects, the present invention provides a method of selecting a mRNA for production of a polypeptide of interest, the method comprising: a) producing an array of individual mRNA sequences comprising different nucleotide sequences encoding the polypeptide of interest; b) determining ensemble free energy (EFE) for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

The present invention further provides a method of selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the highest values for MFE RNA secondary structure and the lowest values for FMFE RNA secondary structure or the mRNA sequence is selected from among the mRNA sequences having an MFE RNA secondary structure in a range from about 0 kcal/mol to about −2 kcal/mol as measured at room temperature and the lowest values for FMFE RNA secondary structure, wherein expression of the selected mRNA sequence results in enhanced production of the polypeptide of interest as compared to the wild-type mRNA sequence.

An additional aspect of the invention provides a method of selecting a mRNA for reduced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the lowest values for MFE RNA secondary structure and the highest values for FMFE RNA secondary structure or the mRNA sequence is selected from among the mRNA sequences having an MFE RNA secondary structure in a range from about −9 kcal/mol to about −18 kcal/mol as measured at room temperature and the highest values for FMFE RNA secondary structure, wherein expression of the selected mRNA sequence results in reduced production of the polypeptide of interest as compared to the wild-type mRNA sequence.

In other aspects of the invention a method is provided for selecting a mRNA for enhanced production of a polypeptide of interest, the method comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble for each individual mRNA sequence of (a); and c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the highest values for EFE and the lowest values for FMFE RNA secondary structure, wherein expression of the selected mRNA sequence results in enhanced production of the polypeptide of interest as compared to the wild-type mRNA sequence.

In still other aspects, the invention provides a method of selecting a mRNA for reduced production of a polypeptide of interest, the method comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble; c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the lowest values for EFE and the highest values for FMFE RNA secondary structure, wherein expression of the selected mRNA sequence results in reduced production of the polypeptide of interest as compared to the wild-type mRNA sequence.

The present invention further provides a method of selecting a mRNA for production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); c) ranking the individual mRNA sequences of the array according to the MFE RNA secondary structure determined in (b) from highest MFE RNA secondary structure to lowest MFE RNA secondary structure; and d) selecting a mRNA sequence from the ranked array of step (c), wherein the mRNA is selected from the group of mRNAs having a MFE RNA secondary structure in a range from about 0 kcal/mol to about −2 kcal/mol, the group of mRNAs having a MFE RNA secondary structure in a range from about −2 kcal/mol to about −9 kcal/mol, or the group of mRNAs having a MFE RNA secondary structure in a range from about −9 kcal/mol to about −18 kcal/mol, wherein the selected mRNA produces the polypeptide of interest.

Additionally provided is a method of selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); and c) selecting a mRNA sequence of (a) having an MFE RNA secondary structure in the range from about 0 kcal/mol to about −2 kcal/mol, wherein expression of the selected mRNA sequence results in enhanced production of the polypeptide of interest as compared to the wild-type mRNA sequence.

In additional aspects of this invention, a method of selecting a mRNA for reduced production of a polypeptide of interest is provided, the method comprising: a) producing an array of individual mRNA sequences comprising different nucleotide sequences encoding the polypeptide of interest; b) determining minimum free energy (MFE) RNA secondary structure for each individual mRNA sequence of (a) and the expression level of each individual mRNA sequence of (a); c) selecting a mRNA sequence of (a) having an MFE RNA secondary structure in the range from about −9 kcal/mol to about −18 kcal/MFE, wherein expression of the selected mRNA sequence results in enhanced production of the polypeptide of interest as compared to the wild-type mRNA sequence.

In some embodiments of the present invention, a method for modifying the production of a polypeptide of interest in a cell of an organism is provided, the method comprising: (a) selecting an mRNA encoding a polypeptide of interest according to the methods of this invention; (b) mutating the nucleotide sequence of the mRNA of (a) to produce a mutated mRNA having an increased or reduced MFE RNA secondary structure as compared to the MFE RNA secondary structure of the nucleotide sequence of the mRNA of (a)) and encoding a polypeptide sequence that is mutated compared to the polypeptide sequence encoded by the mRNA of (a); wherein the mutated polypeptide sequence retains the function of the polypeptide encoded by the mRNA of (a), and expression of the mutated mRNA sequence in a cell of an organism results in modified production of the polypeptide of interest as compared to the wild-type mRNA sequence.

In further embodiments of this invention, a method for modifying the production of a polypeptide of interest in a cell of an organism is provided, the method comprising: (a) selecting an mRNA encoding a polypeptide of interest according to the methods of this invention; (b) identifying the differences between the nucleotide sequence of the mRNA selected according to (a) and a wild-type endogenous nucleotide sequence of said organism, wherein the wild-type endogenous nucleotide sequence encodes a polypeptide of interest that is the same as that encoded by the mRNA selected according to (a); and (c) mutating in situ the endogenous nucleotide sequence encoding the polypeptide of interest to incorporate each of the nucleotide differences identified in (b) into the endogenous nucleotide sequence, whereby the production of the polypeptide of interest from the in situ mutated endogenous nucleotide sequence in the cell of the organism is modified.

Other and further objects, features and advantages would be apparent and more readily understood by reading the following specification and by reference to the accompanying drawing forming a part thereof, or any examples of the embodiments of the invention given for the purpose of the disclosure.

DETAILED DESCRIPTION OF THE INVENTION

Figure 1:
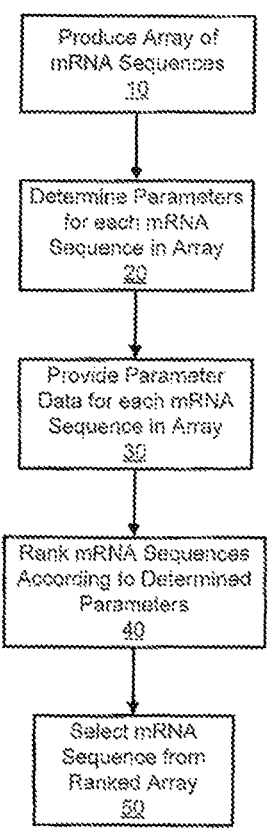
FIG. 1 is a flowchart illustrating operations according to some embodiments of the present invention.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

The present inventors have discovered that by determining one or more (e.g., 1, 2, 3, 4, 5, etc.), or two or more (e.g., 2, 3, 4, 5, etc.) thermodynamic variables of the secondary structure of an mRNA encoding a protein of interest, that a mRNA encoding a polypeptide of interest can be selected that produces a protein at a desired or preselected rate and/or level and/or under specific production conditions. Thus, some embodiments of the invention provide a method of selecting an mRNA for modulated (enhanced or diminished (e.g., reduced)) production of a polypeptide of interest. Accordingly, in some embodiments of the present invention a mRNA encoding a polypeptide of interest can be selected that produces an enhanced or increased amount of protein as compared to the amount of protein produced by the wild-type (i.e., native) mRNA encoding the same polypeptide of interest. In still other embodiments of the invention, a mRNA encoding a polypeptide of interest can be selected that produces a reduced or diminished amount of protein as compared to the amount of protein produced by the wild-type mRNA encoding the same polypeptide of interest. In further aspects of the invention, a first mRNA encoding a polypeptide of interest can be selected that produces an enhanced or increased amount of protein as compared to the amount of protein produced by a second mRNA (e.g., not the native mRNA) encoding the same polypeptide of interest. In still further aspects of the invention, a first mRNA encoding a polypeptide of interest can be selected that produces a diminished or reduced amount of protein as compared to the amount of protein produced by a second selected mRNA encoding the same polypeptide of interest. The amount of enhancement (e.g, increase) or diminishment (e.g., reduction; decrease) can be varied as desired based on the selection of the mRNA using the methods of the present invention. Thus, any mRNA of an array generated based on a native or a second mRNA but that produces a modified amount of a polypeptide of interest as compared to the wild type or native mRNA or second mRNA can be selected using the methods of this invention.

In addition, the methods described here can be used as a tool to overcome RNA silencing. As an example, strong promoters are often used to generate a high level of RNA transcript. However, as is known by those of skill in the art, strong promoters often result in gene silencing. Instead, a moderate or weak promoter can be used in combination with a gene construct comprising a mRNA selected according to the methods of the present invention to produce a mRNA transcript that is more efficiently translated. Thus, despite the use of a weak or moderate promoter, a high level of protein production can be achieved using the methods of the present invention that can identify mRNA transcripts that are more efficiently translated and at the same time avoiding gene silencing due to high transcript levels.

Accordingly, one aspect of the present invention provides a method of selecting a mRNA for production of a polypeptide of interest, the method comprising: a) producing an array of individual mRNA sequences comprising different nucleotide sequences encoding the polypeptide of interest; b) determining one or more of the following parameters for each individual mRNA sequence of (a): (i) ensemble free energy (EFE); (ii) frequency of the minimum free energy (FMFE) RNA secondary structure in a thermodynamic ensemble; and (iii) ensemble diversity (ED); c) ranking the individual mRNA sequences of the array according to the parameters determined in step (b); and d) selecting a mRNA sequence from the ranked array of step (c), wherein the selected mRNA produces the polypeptide of interest. In some embodiments, when two or more parameters are determined, the ranking the individual mRNA sequences of the array in step (c) is according to joint distribution of the parameters determined in step (b), as described previously.

A further aspect of the invention provides a method of selecting a mRNA for production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

In other aspects, the present invention provides a method of selecting a mRNA for production of a polypeptide of interest, the method comprising: a) producing an array of individual mRNA sequences comprising different nucleotide sequences encoding the polypeptide of interest; b) determining ensemble free energy (EFE) for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

Accordingly, in some embodiments of the present invention, the following parameters or combination of parameters can be determined for each individual mRNA sequence of an array and used to rank the individual mRNA sequences (it is noted that when two or more parameters are determined the ranking is according to a joint distribution of the parameters): (1) EFE; (2) FMFE; (3) MFE; (4) ED; (5) EFE and FMFE; (6) EFE and ED; (7) FMFE and ED; (8) EFE, FMFE and ED; (9) MFE and FMFE; (10) MFE and ED; and (11) MFE, FMFE and ED. Further, in some aspects, the present invention further comprises determining base pairing probability (BPP) for each individual mRNA sequence in addition to the parameters or combinations of parameters described above. Thus, as further provided herein, the following combinations of parameters can be determined for each individual mRNA sequence of an array and used to rank the individual mRNA sequences according to a joint distribution: (1) EFE and BPP; (2) FMFE and BPP; (3) ED and BPP; (4) EFE, FMFE and BPP; (5) EFE, ED and BPP; (6) FMFE, ED and BPP; (7) EFE, FMFE, ED and BPP; (8) MFE, FMFE and BPP; (9) MFE, ED and BPP; and (10) MFE, FMFE, ED and BPP.

It will be understood that, although the terms "first," "second," etc. may be used herein to describe various elements, these elements should not be limited by these terms. These terms are only used to distinguish one element from another. Thus, a "first" element (e.g., a first mRNA sequence) discussed below could also be termed a "second" element (e.g., a second mRNA sequence) without departing from the teachings of the present invention.

"Wild type" nucleic acid, nucleotide sequence, polypeptide or amino acid sequence refers to a naturally occurring ("native") or endogenous nucleic acid, nucleotide sequence, polypeptide or amino acid sequence. Thus, a "wild type" mRNA" is an mRNA that is naturally occurring in or endogenous to the organism.

As used herein, the term "thermodynamic optimization method" means any implementation of the Zuker algorithm for determining the minimum free energy structure of a nucleic acid molecule (Zuker et al., *Nucleic Acids Research*, 9, 133-148 (1981); see also, Mathews et al., *J. Mol. Biol.* 288:911-940 (1999) and Walter et al., *PNAS* 91:9218-9222 (1994)).

The term "minimum free energy RNA secondary structure" (MFE) as used herein means the structure found by thermodynamic optimization (i.e. an implementation of the Zuker algorithm (M. Zuker and P. Stiegler., *Nucleic Acids Research* 9:133-148 (1981)) that has the lowest free energy value.

The term "frequency of the minimum free energy RNA secondary structure" (FMFE) refers to the fraction of the MFE structure in the thermodynamic ensemble: $(e^{(-E/kT)})/Z$, where E is the minimum free energy of the structure, k is the Boltzmann constant, T is the temperature and Z is the partition function (Wuchty et al., *Biopolymers* 49:145-165 (1999)). Accordingly, the partition function and the structures of the thermodynamic ensemble are used in determination of the FMFE RNA secondary structure.

As used herein, the term "partition function" refers to partition function as defined by J. S. McCaskill (*Biopolymers* 29:1105-1119 (1990)): $Z=\text{sum}(e^{[Ei/kT]})$, where Ei is the free energy of structure i and the sum is taken over all structures (from i=1 to i=n) for a given sequence.

The term "ensemble free energy" (EFE) as used herein means $-kT*\ln Z$, where k, T, and Z are defined as above and implemented e.g. in the ViennaRNA software package (I. L. Hofacker et al, *Monatsh. Chem.*, 125: 167-188 (1994)). The ensemble free energy is defined by J. S. McCaskill in *Biopolymers* 29:1105-1119 (1990).

As used herein, the term "ensemble diversity" (ED) means the average base pair difference between all structures in the themodynamic ensemble: sum_a,b p_a*p_b*d (a,b), where the sum goes over all pairs of possible structure a,b, p_a is the Boltzmann weight of structure a, and d(a,b) is the base pair distance, where base pair distance is defined by Wuchty et al. in *Biopolymers* 49:145-165 (1999)).

"Joint distribution" of the parameters defines the probability of events in terms of the particular parameters determined such as MFE, EFE, FMFE, ED and/or BPP. Thus, when two or more of the parameters MFE, EFE, FMFE, ED and/or BPP are determined, a joint distribution is used to rank the mRNAs according to the values determined for each parameter for each individual mRNA.

Thus, as used herein, "joint distribution" can be defined by selection of an initial fraction of sequences of interest (e.g., the upper 5% of the MFE structures, as defined above) and then using the other parameter that was determined (e.g., FMFE) to select a fraction of the initial fraction. For example, take the upper and lower 10% of the MFE structures (e.g., for enhanced and reduced expression, respectively), and then take the top 50% of each of those fractions according to their FMFE value.

The term "base pairing probability" (BPP) as used herein means the average across all positions in the nucleotide sequence of the per-position Shannon entropies of the base pairing probabilities. The calculation of the base pairing probabilities is defined by J. S. McCaskill (*Biopolymers* 29:1105-1119 (1990)) and implemented, for example, in the ViennaRNA software package (I. L. Hofacker et al., *Monatsh. Chem.*, 125:167-188 (1994)). The calculation of the entropy values is described by M. Huynen (*J Mol. Biol.* 267:1104-1112 (1997)).

In particular embodiments of the present invention, the methods comprise producing an array of individual mRNA sequences comprising different nucleotide sequences encoding the polypeptide of interest.

In some embodiments of the present invention, an array is produced by backtranslating a polypeptide of interest to produce mRNAs that encode the polypeptide of interest. In particular embodiments, an array is produced by backtranslating the N-terminal end of a polypeptide of interest to produce mRNAs that encode the N-terminal end of a polypeptide of interest. In further embodiments, an array is produced by backtranslating the N-terminal end of a polypeptide of interest to produce mRNAs that encode the N-terminal end of the polypeptide of interest, wherein the individual mRNAs that are produced comprise a start codon and a length of about 20 to 70 nucleotides.

Thus, in some embodiments, an array of individual mRNA sequences is produced, wherein the individual mRNA sequences each comprise the start codon and a length of about 20 to about 25 nucleotides, about 20 to about 30 nucleotides, about 20 to about 35 nucleotides, about 20 to about 40 nucleotides, about 20 to about 45 nucleotides, about 20 to about 50 nucleotides, about 20 to about 55 nucleotides, about 20 to about 55 nucleotides, about 20 to about 60 nucleotides, about 20 to about 65 nucleotides, about 25 to about 30 nucleotides, about 25 to about 35 nucleotides, about 25 to about 40 nucleotides, about 25 to about 45 nucleotides, about 25 to about 50 nucleotides, about 25 to about 55 nucleotides, about 25 to about 60 nucleotides, about 25 to about 65 nucleotides, about 25 nucleotides to about 70 nucleotides, about 30 to about 35 nucleotides, about 30 to about 40 nucleotides, about 30 to about 45 nucleotides, about 30 to about 55 nucleotides, about 30 to about 55 nucleotides, about 30 to about 60 nucleotides, about 30 to about 65 nucleotides, about 30 nucleotides to about 70 nucleotides, about 35 to about 40 nucleotides, about 35 to about 45 nucleotides, about 35 to about 50 nucleotides, about 35 to about 55 nucleotides, about 35 to about 60 nucleotides, about 35 to about 65 nucleotides, about 35 to about 70 nucleotides, about 40 to about 45 nucleotides, about 40 to about 50 nucleotides, about 40 to about 55 nucleotides, about 40 to about 60 nucleotides, about 40 to about 65 nucleotides, about 40 to about 70 nucleotides, about 45 to about 50 nucleotides, about 45 to about 55 nucleotides, about 45 nucleotides to about 60 nucleotides, about 45 to about 65 nucleotides, about 45 to about 70 nucleotides, about 50 to about 55 nucleotides, about 50 to about 60 nucleotides, about 50 to about 65 nucleotides, about 50 to about 70 nucleotides, about 55 to about 60 nucleotides, about 55 to about 65 nucleotides, about 55 to about 70 nucleotides, about 60 to about 65 nucleotides, about 60 to about 70 nucleotides, about 65 to about 70 nucleotides, and the like. Thus, in further embodiments, the individual mRNA sequences of an array comprise a start codon and a length of about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides, about 31 nucleotides, about 32 nucleotides, about 33 nucleotides, about 34 nucleotides, about 35 nucleotides, about 36 nucleotides, about 37 nucleotides, about 38 nucleotides, about 39 nucleotides, about 40 nucleotides, about 41 nucleotides, about 42 nucleotides, about 43 nucleotides, about 44 nucleotides, about 45 nucleotides, about 46 nucleotides, about 47 nucleotides, about 48 nucleotides, about 49 nucleotides, about 50 nucleotides, about 51 nucleotides, about 52 nucleotides, about 53 nucleotides, about 54 nucleotides, about 55 nucleotides, about 56 nucleotides, about 57 nucleotides, about 58 nucleotides, about 59 nucleotides, about 60 nucleotides, about 61 nucleotides, about 62 nucleotides, about 63 nucleotides, about 64 nucleotides, about 65 nucleotides, about 66 nucleotides, about 67 nucleotides, about 68 nucleotides, about 69 nucleotides, or about 70 nucleotides. In particular embodiments of the invention, the individual mRNA sequences of an array comprise a start codon and about 40 nucleotides.

In further embodiments of the present invention, the individual mRNA sequences of the array comprise nucleotides at positions −20 through 50 relative to the start codon (i.e., the A of the ATG (AUG) start codon is zero). In some particular embodiments of the invention, the 5′ ends of the individual mRNA sequences comprise nucleotides at positions −4 through 35 relative to the start codon. In additional embodiments of the invention, the 5′ ends of the individual mRNA sequences comprise nucleotides at positions −4 through 37 relative to the start codon.

In other embodiments, the individual mRNA sequences comprise nucleotides at positions −15 through 50 relative to the start codon, at positions −10 through 50 relative to the start codon, at positions −5 through 50 relative to the start codon, at positions −20 through 45 relative to the start codon, at positions −15 through 45 relative to the start codon, at positions −10 through 45 relative to the start codon, at positions −5 through 45 relative to the start codon, at positions −20 through 40 relative to the start codon, at positions −15 through 40 relative to the start codon, at positions −10 through 40 relative to the start codon, at positions −5 through 40 relative to the start codon, at positions −20 through 35 relative to the start codon, at positions −15 through 35 relative to the start codon, at positions −10 through 35 relative to the start codon, at positions −5 through 35 relative to the start codon, at positions −20 through 30 relative to the start codon, at positions −15 through 30 relative to the start codon, at positions −10 through 30 relative to the start codon, at positions −5 through 30 relative to the start codon, at positions −20 through 25 relative to the start codon, at positions −15 through 25 relative to the start codon, at positions −10 through 25 relative to the start codon, at positions −5 through 25 relative to the start codon, at positions −20 through 20 relative to the start codon, at positions −15 through 20 relative to the start codon, at positions −10 through 20 relative to the start codon, at positions −5 through 20 relative to the start codon, at positions −20 through 15 relative to the start codon, at positions −15 through 15 relative to the start codon, at positions −10 through 15 relative to the start codon, at positions −5 through 15 relative to the start codon, at positions −20 through 10 relative to the start codon, at positions −15 through 10 relative to the start codon, at positions −10 through 10 relative to the start codon, and the like. Thus, in some particular embodiments, the individual mRNA sequences of an array comprise a start codon and about 40 nucleotides with the 5′ end of the individual mRNA sequences comprising nucleotides at positions −4 through 35 relative to the start codon.

In some embodiments of the present invention, an array is produced comprising all possible mRNAs that encode the polypeptide of interest. In other embodiments of the invention, an array is produced that is a "representative array." Thus, as used herein, a representative array means an array in which not all mRNAs that could possibly encode for a polypeptide of interest are produced and evaluated for the parameters described herein but instead a subpopulation or subgroup that is representative of the distribution of mRNAs that could encode for the polypeptide of interest is produced and evaluated. A representative array can be produced using biased or unbiased protocols as known in the art. A non-limiting example of an unbiased method of generating a representative array begins with an input amino acid sequence. An automated random sampling procedure is used to generate nucleotide sequences encoding the input amino acid sequence (e.g., BioPerl). (Stajich et al. *Genome Res* 12(10):1611-8 (2002)). For each position in the amino acid sequence, codons for that position are selected by sampling the possible codons from a uniform distribution. Thus, in some embodiments, ten thousand nucleotide sequences are produced in this manner for each input amino acid sequence. In other embodiments, a larger or smaller number of nucleotide sequences are produced. The number of sequences produced will depend on a number of factors including the length of the input amino acid sequence.

Accordingly, in some particular embodiments of the invention, an array comprises about $10^3$ to about $10^8$ individual mRNA sequences. In other embodiments, an array of the invention comprises about $10^3$, about $2\times10^3$, about $4\times10^3$, about $6\times10^3$, about $8\times10^3$, about $10^4$, about $2\times10^4$, about $4\times10^4$, about $6\times10^4$, about $8\times10^4$, about $10^5$, about $2\times10^5$, about $4\times10^5$, about $6\times10^5$, about $8\times10^5$, about $10^6$, about $2\times10^6$, about $4\times10^6$, about $6\times10^6$, about $8\times10^6$, about $10^7$, about $2\times10^7$, about $4\times10^7$, about $6\times10^7$, about $8\times10^7$, or about $10^8$ individual mRNA sequences.

As described herein, the present invention provides methods of selecting a mRNA having a desired level of production of a polypeptide of interest. Thus, in some embodiments, the present invention provides a method of selecting a mRNA for production of a polypeptide of interest, wherein the production of the polypeptide of interest is enhanced. In other embodiments, a method is provided for selecting a mRNA for production of a polypeptide of interest, wherein the production of the polypeptide of interest is reduced. A mRNA selected as described herein can have slightly enhanced, moderately enhanced or greatly enhanced protein production.

In other embodiments of the invention, a mRNA can be selected having a desired level of protein production that is slightly reduced, moderately reduced or greatly reduced. In some embodiments, the level of protein production by a selected mRNA is enhanced or reduced as compared to the production of the same polypeptide of interest by the wild-type mRNA. In some embodiments, a mRNA sequence is selected that produces the same amount of protein as compared to the production of the same polypeptide of interest by the wild-type mRNA (0% enhanced or reduced).

As used herein, slightly enhanced or slightly reduced can mean a change in production of a polypeptide of interest of about 0.0001%, 0.0005%, 0.001%, 0.005%, 0.01%, 0.05%, 0.1%, 0.5%, 1%, 2%, 3%, 4%, 5%, 6%, 7%, 10%, 11%, 12%, 13%, 14%, 15%, 16%, 17%, 18%, 19%, 20%, 21%, 22%, 23%, 24%, 25%, and the like, as compared to a native mRNA or other selected mRNA. Moderately enhanced or moderately reduced can mean a change in production of a polypeptide of interest of about 25%, 26%, 27%, 28%, 29%, 30%, 31%, 32%, 33%, 34%, 35%, 36%, 37%, 38%, 39%, 40%, 41%, 42%, 43%, 44%, 45%, and the like as compared to a native mRNA or other selected mRNA. Greatly enhanced or greatly reduced can mean a change in production of a polypeptide of interest of about 45% to about 100% (e.g., 45%, 46%, 47%, 48%, 49%, 50%, 51%, 52%, 53%, 54%, 55%, 60%, 65%, 70%, 75%, 80%, 85%, 90%, 95%, 100%, etc.) as compared to a native mRNA or other selected mRNA.

In other embodiments, the present invention provides a method of selecting a first mRNA (selected mRNA) for production of a polypeptide of interest, wherein the production of the polypeptide of interest by the first mRNA is enhanced or reduced as compared to the production of the polypeptide by a second mRNA that encodes the same polypeptide of interest as encoded by the first mRNA.

Thus, the present invention provides methods for selecting an mRNA based on its ranking within the distribution of values for each parameter determined for the individual mRNA sequences in the array. Thus, for example, the mRNAs of an array are ranked from highest to lowest value for each parameter determined (i.e., MFE RNA secondary structure, EFE, FMFE RNA secondary structure, ED and/or BPP); thus, providing a distribution of mRNAs coding for a single polypeptide of interest but having different values for the determined parameter (i.e, MFE RNA secondary structure, EFE, FMFE RNA secondary structure, ED, and/or BPP). The distribution can be described as ranging from the highest value at 100% to the lowest value at less than 1% (e.g., 0.0001%, 0.0005%, 0.001%, 0.005%, 0.01%, etc.). A mRNA can be selected from anywhere along the distribution from less than 1% (e.g., 0.0001%, 0.0005%, 0.001%, 0.005%, 0.01%, etc.) to 100%. Thus, by selecting a mRNA as described herein a desired level of protein production can be achieved.

Accordingly, in some embodiments of the present invention, a mRNA can be selected from among the mRNAs of a given array having an MFE RNA secondary structure value between about 95%-100% of the highest MFE value determined for that array of sequences. In other embodiments, a mRNA can be selected from among the mRNA sequences having an MFE value in a range of between about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%-15%, 5%-10%, 0%-5%, and the like, of the highest MFE value determined for that array of mRNA sequences. Thus, in some embodiments, a mRNA can be selected from among the mRNA sequences having an MFE value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest MFE value determined for that array of sequences.

In other embodiments, the MFE RNA secondary structure (MFE) value versus level of protein production for the mRNAs within the array does not form a linear pattern but instead forms a step-wise pattern with the mRNAS falling into groups in which the level of expression or protein production is the same for the mRNAs within each group despite having different MFE values. Specifically, in a step-wise pattern, when other factors affecting protein expression hold constant, mRNAs with MFE values falling within a particular range can have same protein expression level. Thus, the grouping of mRNAs in some embodiments is based on the calculated MFE.

A step-wise pattern of expression level can occur because the energy required to open up a given mRNA structure for translation can be the same for mRNAs having different MFE values. Thus, for example, the $\Delta G°$ for hydrolysis of a single GTP to GDP at 25° C. is −6.95 kcal/mol (at 37° C. the $\Delta G°$ is −7.14). Accordingly, in some instances, certain mRNAs having different MFE values can each require the energy of a single GTP (a "single packet of energy") in order to open up their structure for translation. Thus, the level of expression or protein production from those mRNAs requiring a "single packet of energy" (e.g., ATP, GTP and the like) can be the same or similar despite the different MFE values and therefore, similar levels of protein production can be achieved by selecting any mRNA from within a particular range of MFE values. As an example, a mRNA having a MFE value of −3 kcal/mol and another mRNA having MFE value of −6 kcal/mol, both may require one or less than one packet of energy in order to open up their structure for translation. Consequently, the efficiency of protein production for these two mRNAs is the same and therefore either may be selected without consequences for the level of protein production.

The boundaries between ranges are determined by the number of "energy packets" (e.g., GTP, ATP and the like) hydrolyzed and the corresponding energy released. Thus, for example, the first range can correspond to zero GTP hydrolysis, the second range to 1 GTP hydrolysis, and so on. The boundaries can be variable to some degree and there are some overlapping between neighboring ranges because (1) the energy released from the hydrolysis varies with temperature and in vivo aquatic and ionic environment and (2) the calculation of MFE for mRNAs can be approximate. Generally, the boundaries are calculated by experiment and mRNAs near the boundaries are avoided. As described herein, the equation for calculating MFE is known in the art (i.e., $e^{(-E/kT)}/Z$, where E is the minimum free energy of the structure, k is the Boltzmann constant, T is the temperature and Z is the partition function (Wuchty et al., *Biopolymers* 49:145-165 (1999))

Accordingly, in some embodiments, a mRNA can be selected from among a group of mRNAs in a given array having an MFE RNA secondary structure value in a range from about 0 kcal/mol to about −2 kcal/mol, in a range from about −2 kcal/mol to about −9 kcal/mol, or in a range from about −9 kcal/mol to about −18 kcal/mol. The choice of which group to select from will depend on the level of protein production desired. Thus, in some embodiments, when enhanced protein production is desired, the mRNA can be selected from a group of mRNAs having an MFE RNA secondary structure value in a range from about 0 kcal/mol to about −2 kcal/mol. Therefore, a mRNA can be selected that has a MFE value of about 0 kcal/mol, −0.1 kcal/mol, −0.2 kcal/mol, −0.3 kcal/mol, −0.4 kcal/mol, −0.5 kcal/mol, −0.6 kcal/mol, −0.7 kcal/mol, −0.9 kcal/mol, −1 kcal/mol, −1.1 kcal/mol, −1.2 kcal/mol, −1.3 kcal/mol, −1.4 kcal/mol, −1.5 kcal/mol, −1.6 cal/mol, −1.7 kcal/mol, −1.8 kcal/mol, −1.9 kcal/mol, −2 kcal/mol, and the like.

In other embodiments, when reduced protein production is desired, the mRNA can be selected from a group of mRNAs having an MFE RNA secondary structure value in a range from about −9 kcal/mol to about −18 kcal/mol. In some embodiments, when reduced protein production is desired, the mRNA can be selected from a group of mRNAs having an MFE RNA secondary structure value in a range from about −9 kcal/mol to about −23 kcal/mol. In other embodiments, when reduced protein production is desired, the mRNA can be selected from a group of mRNAs having an MFE RNA secondary structure value in a range from about −9 kcal/mol to about −30 kcal/mol. Thus, in some embodiments, when reduced protein production is desired, a mRNA can be selected that has a MFE value of about −9 kcal/mol, −9.1 kcal/mol, −9.2 kcal/mol, −9.3 kcal/mol, −9.4 kcal/mol, −9.5 kcal/mol, −9.6 kcal/mol, −9.7 kcal/mol, −9.9 kcal/mol, −10 kcal/mol, −10.1 kcal/mol, −10.2 kcal/mol, −10.3 kcal/mol, −10.4 kcal/mol, −10.5 kcal/mol, −10.6 cal/mol, −10.7 kcal/mol, −10.8 kcal/mol, −10.9 kcal/mol, −11 kcal/mol, −11.1 kcal/mol, −11.2 kcal/mol, −11.3 kcal/mol, −11.4 kcal/mol, −11.5 kcal/mol, −11.6 cal/mol, −11.7 mol, −11.8 kcal/mol, −11.9 kcal/mol, −12 kcal/mol, −12.1 kcal/mol, −12.2 kcal/mol, −12.3 kcal/mol, −12.4 kcal/mol, −12.5 kcal/mol, −12.6 cal/mol, −12.7 kcal/mol, −12.8 kcal/mol, −12.9 kcal/mol, −13 kcal/mol, −13.1 kcal/mol, −13.2 kcal/mol, −13.3 kcal/mol, −13.4 kcal/mol, −13.5 kcal/mol, −13.6 cal/mol, −13.7 kcal/mol, −13.8 kcal/mol, −13.9 kcal/mol, −14 kcal/mol, −14.1 kcal/mol, −14.2 kcal/mol, −14.3 kcal/mol, −14.4 kcal/mol, −14.5 kcal/mol, −14.6 cal/mol, −14.7 kcal/mol, −14.8 kcal/mol, −14.9 kcal/mol, −15 kcal/mol, −15.1 kcal/mol, −15.2 kcal/mol, −15.3 kcal/mol, −15.4 kcal/mol, −15.5 kcal/mol, −15.6 cal/mol, −15.7 kcal/mol, −15.8 kcal/mol, −15.9 kcal/mol, −16 kcal/mol, −16.1 kcal/mol, −16.2 kcal/mol, −16.3 kcal/mol, −16.4 kcal/mol, −16.5 kcal/mol, −16.6 cal/mol, −16.7 kcal/mol, −16.8 kcal/mol, −16.9 kcal/mol, −17 kcal/mol, −17.1 kcal/mol, −17.2 kcal/mol, −17.3 kcal/mol, −17.4 kcal/mol, −17.5 kcal/mol, −17.6 cal/mol, −17.7 kcal/mol, −17.8 kcal/mol, −17.9 kcal/mol, −18 kcal/mol, −18.1 kcal/mol, −18.2 kcal/mol, −18.3 kcal/mol, −18.4 kcal/mol, −18.5 kcal/mol, −18.6 cal/mol, −18.7 kcal/mol, −18.8 kcal/mol, −18.9 kcal/mol, −19 kcal/mol, −19.5 kcal/mol, −20 kcal/mol, −20.5 kcal/mol, −21 kcal/mol, −21.5 kcal/mol, −22 kcal/mol, −22.5 kcal/mol, −23 kcal/mol, −23.5 kcal/mol, −24 cal/mol, −24.5 kcal/mol, −25 kcal/mol, −25.5 kcal/mol, −26 kcal/mol, −26.5 kcal/mol, −27 kcal/mol, −27.5 kcal/mol, −28.5 kcal/mol, −29 kcal/mol, −29.5 kcal/mol, −30 kcal/mol, and the like.

In still other embodiments, depending on the desired level of expression, the mRNA can be selected from a group of mRNAs having an MFE RNA secondary structure value in a range from about −2 kcal/mol to about −9 kcal/mol. Thus, a mRNA can be selected that has a MFE value of about −2 kcal/mol, −2.1 kcal/mol, −2.2 kcal/mol, −2.3 kcal/mol, −2.4 kcal/mol, −2.5 kcal/mol, −2.6 kcal/mol, −2.7 kcal/mol, −2.9 kcal/mol, −3 kcal/mol, −3.1 kcal/mol, −3.2 kcal/mol, −3.3 kcal/mol, −3.4 kcal/mol, −3.5 kcal/mol, −3.6 cal/mol, −3.7 kcal/mol, −3.8 kcal/mol, −3.9 kcal/mol, −4 kcal/mol, −4.1 kcal/mol, −4.2 kcal/mol, −4.3 kcal/mol, −4.4 kcal/mol, −4.5 kcal/mol, −4.6 cal/mol, −4.7 kcal/mol, −4.8 kcal/mol, −4.9 kcal/mol, −5 kcal/mol, −5.1 kcal/mol, −5.2 kcal/mol, −5.3 kcal/mol, −5.4 kcal/mol, −5.5 kcal/mol, −5.6 kcal/mol, −5.7 kcal/mol, −5.8 kcal/mol, −5.9 kcal/mol, −6 kcal/mol, −6.1 kcal/mol, −6.2 kcal/mol, −6.3 kcal/mol, −6.4 kcal/mol, −6.5 kcal/mol, −6.6 kcal/mol, −6.7 kcal/mol, −6.8 kcal/mol, −6.9 kcal/mol, −7 kcal/mol, −7.1 kcal/mol, −7.2 kcal/mol, −7.3 kcal/mol, −7.4 kcal/mol, −7.5 kcal/mol, −7.6 cal/mol, −7.7 kcal/mol, −7.8 kcal/mol, −7.9 kcal/mol, −8 kcal/mol, −8.1 kcal/mol, −8.2 kcal/mol, −8.3 kcal/mol, −8.4 kcal/mol, −8.5 kcal/mol, −8.6 cal/mol, −8.7 kcal/mol, −8.8 kcal/mol, −8.9 kcal/mol, −9 kcal/mol, and the like.

Therefore, in some embodiments of this invention, a method of selecting a mRNA for production of a polypeptide of interest is provided, the method comprising: a) producing an array of individual mRNA sequences comprising different nucleotide sequences encoding the polypeptide of interest; b) determining minimum free energy (MFE) RNA secondary structure for each individual mRNA sequence of (a); c) ranking the individual mRNA sequences of the array according to the MFE RNA secondary structure determined in (b) from highest MFE RNA secondary structure to lowest MFE RNA secondary structure; and d) selecting a mRNA sequence from the ranked array of step (c), wherein the mRNA is selected from the group of mRNAs having a MFE RNA secondary structure in a range of about 0 kcal/mol to about −2 kcal/mol, the group of mRNAs having a MFE RNA secondary structure in a range of about −2 kcal/mol to about −9 kcal/mol, or the group of mRNAs having a MFE RNA secondary structure in a range from about −9 kcal/mol to about −18 kcal/mol, wherein the selected mRNA produces the polypeptide of interest.

In other embodiments, the present invention provides a method of selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); and c) selecting a mRNA sequence of (a) having an MFE RNA secondary structure in the range of about 0 kcal/mol to about −2 kcal/mol, wherein expression of the selected mRNA sequence results in enhanced production of the polypeptide of interest as compared to the wild-type mRNA sequence.

In additional embodiments, a method of selecting a mRNA for reduced production of a polypeptide of interest is provided, the method comprising: a) producing an array of individual mRNA sequences comprising different nucleotide sequences encoding the polypeptide of interest; b) determining minimum free energy (MFE) RNA secondary structure for each individual mRNA sequence of (a) and the expression level of each individual mRNA sequence of (a); c) selecting a mRNA sequence of (a) having an MFE RNA secondary structure in the range of about −9 kcal/mol to about −18 kcal/MFE, wherein expression of the selected mRNA sequence results in enhanced production of the polypeptide of interest as compared to the wild-type mRNA sequence.

In other embodiments, a mRNA can be selected from among the mRNAs of a given array having an EFE value between about 95%-100% of the highest EFE value determined for that array of sequences. In other embodiments, a mRNA can be selected from among the mRNA sequences having an EFE value in a range of between about 90%400%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%45%, 5%40%, 0%-5%, and the like, of the highest EFE value determined for that array of mRNA sequences. Thus, in some embodiments, a mRNA can be selected from among the mRNA sequences having an EFE value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest EFE value determined for that array of sequences.

In still other embodiments, a mRNA can be selected from among the mRNA sequences of a given array having an FMFE RNA secondary structure value between about 95%-100% of the highest FMFE value determined for that array of sequences. In other embodiments, a mRNA can be selected from among the mRNAs having an FMFE value in a range of between about 90%400%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%-15%, 5%-10%, 0%-5%, and the like, of the highest FMFE value determined for that array of sequences. Thus, in further embodiments, a mRNA can be selected from among the mRNA sequences having an FMFE value of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest FMFE value determined for that array of sequences.

In further embodiments, a mRNA can be selected from among the mRNA sequences of a given array having an MFE RNA secondary structure value between about 95%-100% of the highest MFE value determined for that array of sequences. In other embodiments, a mRNA can be selected from among the mRNAs having an MFE value in a range of between about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%-15%, 5%-10%, 0%-5%, and the like, of the highest MFE value determined for that array of sequences. Thus, in further embodiments, a mRNA can be selected from among the mRNA sequences having an MFE value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest MFE value determined for that array of sequences.

In still further embodiments of the invention, a mRNA can be selected from among the mRNAs of a given array having an ED value between about 95%-100% of the highest ED value determined for that array of sequences. In other embodiments, a mRNA can be selected from among the mRNA sequences having an ED value in a range of between about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%-15%, 5%-10%, 0%-5%, and the like, of the highest ED value determined for that array of mRNA sequences. Thus, in some embodiments, a mRNA can be selected from among the mRNA sequences having an ED value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest ED value determined for that array of sequences.

In additional aspects of the invention, a mRNA can be selected from among the mRNA sequences of a given array having an BPP value between about 95%-100% of the highest BPP value determined for that array of sequences. In other embodiments, a mRNA can be selected from among the mRNA sequences having an BPP value in a range between about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, 50%-55%, 45%-55%, 40%-55%, 45%-50%, 40%-50%, 35%-50%, 40%-45%, 35%-45%, 30%-45%, 35%-40%, 30%-40%, 25%-40%, 30%-35%, 25%-35%, 20%-35%, 25%-30%, 20%-30%, 15%-30%, 20%-25%, 15%-25%, 10%-25%, 15%-20%, 10%-20%, 5%-20%, 10%-15%, 5%-15%, 0%-15%, 5%-10%, 0%-5%, and the like, of the highest BPP value determined for that array of sequences. Thus, in further embodiments, a mRNA can be selected from among the mRNAs having an BPP value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% of the highest BPP value determined for that array of sequences.

In further aspects of the invention, when selecting a mRNA for enhanced production of a polypeptide of interest as described herein and MFE RNA secondary structure, EFE, and/or ED is a parameter(s) determined for each individual mRNA sequences of an array that is used in ranking the individual mRNA sequences of the array, then the mRNA is selected from among the mRNA sequences having the highest values for MFE RNA secondary structure, EFE, and/or ED determined for that array of mRNA sequences. Thus, in particular aspects of the invention, when selecting a mRNA for enhanced production of a polypeptide of interest, the mRNA can be selected from among the mRNA sequences having a value for MFE RNA secondary structure, EFE, and/or ED that is about 95-100% of the highest value for the parameter that is determined for that array of sequences. In other embodiments, when selecting a mRNA for enhanced production of a polypeptide of interest, the mRNA can be selected from among the mRNAs having a value in a range of about 90%400%, 85%400%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, and the like, of the highest value for MFE RNA secondary structure, EFE, and/or ED that is determined for that array of sequences. In still other embodiments, when selecting a mRNA for enhanced production of a polypeptide of interest, the mRNA is selected from among the mRNA sequences of the array having a value of about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, and the like, of the highest value for MFE RNA secondary structure, EFE, and/or ED that is determined for that array of sequences.

In other aspects of the invention, when selecting a mRNA for enhanced production of a polypeptide of interest as described herein and FMFE RNA secondary structure is a parameter determined for each individual mRNA sequences of an array that is used in ranking the individual mRNA sequences of the array, then the mRNA is selected from among the mRNA sequences having the lowest value for FMFE RNA secondary structure determined for that array of mRNA sequences. Thus, in particular aspects of the invention, the mRNA can be selected from among the mRNAs having a value for FMFE of about 0%-5% of the highest value for FMFE RNA secondary structure determined for that array of sequences. In other embodiments, the mRNA can be selected from among the mRNAs having a value in a range of about 0%-10%, 5%-10%, 0%-15%, 0%-20%, 5%-15%, 10%-15%, 5%-20%, 10%-20%, 15%-20%, 10%-25%, 15%-25%, 20%-25%, 15%-30%, 20%-30%, 25%-30%, 20%-35%, 25%-35%, 30%-35%, 25%-40%, 30%-40%, 35%-40%, 30%-45%, 35%-45%, 40%-45%, 35%-50%, 40%-50%, 45%-50%, 40%-55%, 45%-55%, and the like, of the highest value for FMFE RNA secondary structure that is determined for that array of sequences. In still other embodiments, when selecting a mRNA for enhanced production of a polypeptide of interest, the mRNA is selected from among the mRNA sequences of the array having a value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, and the like, of the highest value for FMFE that is determined for that array of sequences.

In further aspects of the invention, when selecting a mRNA for enhanced production of a polypeptide of interest as described herein and BPP is a parameter determined for each individual mRNA sequences of an array that is used in ranking the individual mRNA sequences of the array, then the mRNA is selected from among the mRNA sequences having the highest values for BPP determined for that array of mRNA sequences. Thus, in particular aspects of the invention, when selecting a mRNA for enhanced production of a polypeptide of interest, the mRNA can be selected from among the mRNA sequences having a value for BPP that is about 95-100% of the highest value for the parameter that is determined for that array of sequences. In other embodiments, when selecting a mRNA for enhanced production of a polypeptide of interest, the mRNA can be selected from among the mRNAs having a value in a range of about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, and the like, of the highest value for BPP that is determined for that array of sequences. In still other embodiments, when selecting a mRNA for enhanced production of a polypeptide of interest, the mRNA is selected from among the mRNA sequences of the array having a value of about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, and the like, of the highest value for BPP that is determined for that array of sequences.

In other aspects of the invention, when selecting a mRNA for reduced production of a polypeptide of interest as described herein and MFE RNA secondary structure, EFE, and/or ED is a parameter(s) determined for each individual mRNA sequences of an array that is used in ranking the individual mRNA sequences of the array, then the mRNA is selected from among the mRNA sequences having the lowest value for MFE RNA secondary structure, EFE, and/or ED, respectively, determined for that array of mRNA sequences. Thus, in particular aspects of the invention, when selecting a mRNA for reduced production of a polypeptide of interest, the mRNA can be selected from among the mRNAs having a value of about 0%-5% of the highest value for MFE RNA secondary structure, EFE, and/or ED determined for that array of sequences. In other embodiments, when selecting a mRNA for reduced production of a polypeptide of interest, the mRNA can be selected from among the mRNAs having a value in a range of about 0%-10%, 5%-10%, 0%-15%, 0%-20%, 5%-15%, 10%-15%, 5%-20%, 10%-20%, 15%-20%, 10%-25%, 15%-25%, 20%-25%, 15%-30%, 20%-30%, 25%-30%, 20%-35%, 25%-35%, 30%-35%, 25%-40%, 30%-40%, 35%-40%, 30%-45%, 35%-45%, 40%-45%, 35%-50%, 40%-50%, 45%-50%, 40%-55%, 45%-55%, and the like, of the highest value for MFE RNA secondary structure, EFE, and/or ED determined for that array of sequences. In still other embodiments, when selecting a mRNA for reduced production of a polypeptide of interest, the mRNA is selected from among the mRNA sequences of the array having a value of about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, and the like, of the highest value for MFE RNA secondary structure, EFE, and/or ED that is determined for that array of sequences.

In further aspects of the invention, when selecting a mRNA for reduced production of a polypeptide of interest as described herein and FMFE RNA secondary structure is a parameter(s) determined for each individual mRNA sequences of an array that is used in ranking the individual mRNA sequences of the array, then the mRNA is selected from among the mRNA sequences having the highest value for FMFE RNA secondary structure determined for that array of sequences. Thus, in particular aspects of the invention, when selecting a mRNA for reduced production of a polypeptide of interest, the mRNA can be selected from among the mRNAs having a value for FMFE RNA secondary structure of about 95-100% of the highest value for FMFE that is determined for that array of sequences. Thus, in some embodiments, when selecting a mRNA for reduced production of a polypeptide of interest, the mRNA can be selected from among the mRNAs having a value in a range of about 90%-100%, 85%-100%, 90%-95%, 85%-95%, 80%-95%, 85%-90%, 80%-90%, 75%-90%, 80%-85%, 75%-85%, 70%-85%, 75%-80%, 70%-80%, 65%-80%, 70%-75%, 65%-75%, 60%-75%, 65%-70%, 60%-70%, 55%-70%, 60%-65%, 55%-65%, 50%-65%, 55%-60%, 50%-60%, 45%-60%, and the like, of the highest value for FMFE RNA secondary structure that is determined for that array of sequences. In still other embodiments, when selecting a mRNA for reduced production of a polypeptide of interest, the mRNA is selected from among the mRNA sequences of the array having a value of about 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, and the like, of the highest value for FMFE that is determined for that array of sequences.

In additional embodiments, when selecting a mRNA for enhanced production of polypeptide of interest and MFE RNA secondary structure is determined for each individual mRNA sequence of an array and used in ranking the individual mRNA sequences of the array, then the mRNA is selected from among about 0.0001% to about 20% (e.g., about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%) of the mRNA sequences in the ranked array with the highest values for MFE RNA secondary structure determined for that array. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of mRNA sequences in the ranked array with the highest values for MFE RNA secondary structure. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the highest values for MFE RNA secondary structure.

In other aspects of the invention, when selecting a mRNA for enhanced production of polypeptide of interest as described herein and EFE is a parameter determined for each individual mRNA sequence of an array that is used in ranking the individual mRNA sequences of the array, then the mRNA is selected from among about 0.0001% to about 20% (e.g., 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%) of the mRNA sequences in the ranked array with the highest values for EFE. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the highest values for EFE. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the highest values for EFE.

In other aspects of the invention, when selecting a mRNA for enhanced production of polypeptide of interest as described herein and ED is a parameter determined for each individual mRNA sequence of an array that is used in ranking the individual mRNA sequences of the array, then the mRNA is selected from among about 0.0001% to about 20% (e.g., 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%) of the mRNA sequences in the ranked array with the highest values for ED. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the highest values for ED. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the highest values for ED.

In still other aspects of the invention, when selecting a mRNA for enhanced production of polypeptide of interest as described herein and FMFE RNA secondary structure is a parameter determined for each individual mRNA sequence of an array that is used in ranking the individual mRNA sequences of the array, then the mRNA is selected from among about 0.0001% to about 20% (e.g., 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%) of the mRNA sequences in the ranked array with the lowest values for FMFE RNA secondary structure. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for FMFE RNA secondary structure. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the lowest values for FMFE RNA secondary structure.

The present invention further provides that when selecting a mRNA for enhanced production of polypeptide of interest as described herein and BPP is a parameter determined for each individual mRNA sequence of an array that is used in ranking the individual mRNA sequences of the array, then the mRNA is selected from among about 0.0001% to about 20% of the mRNA sequences in the ranked array with the highest values for BPP. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about 15% to about 20%, or any combination thereof, of the mRNA sequences in the ranked array with the highest values for BPP. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the highest values for BPP.

In still further aspects of the invention, when selecting a mRNA for reduced production of polypeptide of interest as described herein and MFE RNA secondary structure is a parameter determined for each individual mRNA sequences of an array that is used in ranking the individual mRNA sequences of the array, then the mRNA is selected from among about 0.0001% to about 20% (e.g., 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%) of the mRNA sequences in the ranked array with the lowest values for MFE RNA secondary structure. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for MFE RNA secondary structure. In other embodiments, when selecting a mRNA for reduced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the lowest values for MFE RNA secondary structure.

In still further aspects of the invention, when selecting a mRNA for reduced production of polypeptide of interest as described herein and EFE is a parameter determined for each individual mRNA sequences of an array that is used in ranking the individual mRNA sequences of the array, then the mRNA is selected from among about 0.0001% to about 20% of the mRNA sequences in the ranked array with the lowest values for EFE. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for EFE. In other embodiments, when selecting a mRNA for reduced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the lowest values for EFE.

In some aspects of the invention, when selecting a mRNA for reduced production of polypeptide of interest as described herein and ED is a parameter determined for each individual mRNA sequences of an array that is used in ranking the individual mRNA sequences of the array, then the mRNA is selected from among about 0.0001% to about 20% of the mRNA sequences in the ranked array with the lowest values for ED. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for ED. In other embodiments, when selecting a mRNA for reduced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination or range thereof, of the mRNA sequences in the ranked array with the lowest values for ED.

In other aspects of the invention, when selecting a mRNA for reduced production of polypeptide of interest as described herein and FMFE RNA secondary structure is a parameter determined for each individual mRNA sequences of an array that is used in ranking the individual mRNA sequences of the array, then the mRNA is selected from among about 0.0001% to about 20% of the mRNA sequences in the ranked array with the highest values for FMFE RNA secondary structure. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the highest values for FMFE RNA secondary structure. In other embodiments, when selecting a mRNA for reduced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination or range thereof, of the mRNA sequences in the ranked array with the highest values for FMFE RNA secondary structure.

The present invention further provides that when selecting a mRNA for reduced production of polypeptide of interest as described herein and BPP is a parameter determined for each individual mRNA sequence of an array that is used in ranking the individual mRNA sequences of the array, then the mRNA is selected from among about 0.0001% to about 20% of the mRNA sequences in the ranked array with the lowest values for BPP. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for BPP. In other embodiments, when selecting a mRNA for reduced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination or range thereof, of the mRNA sequences in the ranked array with the lowest values for BPP.

Accordingly, in some aspects of the present invention, a method is provided for selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the highest values for MFE RNA secondary structure and the lowest values for FMFE RNA secondary structure or the mRNA sequence is selected from among the mRNA sequences having an MFE RNA secondary structure in a range of about 0 kcal/mol to about −2 kcal/mol as measured at room temperature and the lowest values for FMFE RNA secondary structure, wherein expression of the selected mRNA sequence results in enhanced production of the polypeptide of interest as compared to the wild-type mRNA sequence. Thus, in additional aspects of the invention, when selecting a mRNA for enhanced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the highest values for MFE RNA secondary structure and the lowest values for FMFE RNA secondary structure. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the highest values for MFE RNA secondary structure and the lowest values for FMFE RNA secondary structure.

Further, in some aspects, the present invention further comprises determining base pairing probability (BPP) for each individual mRNA sequence in addition to MFE and FMFE. Thus, when selecting a mRNA for enhanced production of a polypeptide of interest and BPP is determined and used in ranking the individual mRNA sequences of the array according to a joint distribution, then the mRNA is selected from among about 0.0001% to about 20% of sequences in the ranked array with the highest values for BPP. Thus, in additional aspects of the invention, when selecting a mRNA for enhanced production of polypeptide of interest, the mRNA can be selected from among about 0.0001% to about 10%, about 1 to about 10%, about 5% to about 15%, about 10% to about 15%, about 10% to about 20%, about the 15% to about 20%, or any combination thereof, of the mRNA sequences in the ranked array with the highest values for BPP. In other embodiments, when selecting a mRNA for enhanced production of polypeptide of interest, the mRNA is selected from among about 0.0001%, 0.0005%, 0.001%, 0.005%, 0.01%, 0.05%, 0.1%, 0.5%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the highest values for BPP.

In a further aspect of the invention, a method is provided for selecting a mRNA for reduced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the lowest values for MFE RNA secondary structure and the highest values for FMFE RNA secondary structure or the mRNA sequence is selected from among the mRNA sequences having an MFE RNA secondary structure in a range of about −9 kcal/mol to about −18 kcal/mol as measured at room temperature and the highest values for FMFE RNA secondary structure. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for MFE RNA secondary structure and the highest values for FMFE RNA secondary structure. In other embodiments, when selecting a mRNA for reduced production of polypeptide of interest, the mRNA is selected from among about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the lowest values for MFE RNA secondary structure and the highest values for FMFE RNA secondary structure.

Further, in some aspects, the present invention further comprises determining base pairing probability (BPP) for each individual mRNA sequence in addition to MFE and FMFE. In some aspects of the present invention, the method further comprises determining base pairing probability (BPP) for each individual mRNA sequence in addition to MFE and FMFE. Thus, when selecting a mRNA for reduced production of a polypeptide of interest and BPP is determined and used in ranking the individual mRNA sequences of the array according to a joint distribution, then the mRNA is selected from among about 0.0001% to about 20% of sequences in the ranked array with the lowest values for BPP. Thus, in additional aspects of the invention, when selecting a mRNA for reduced production of polypeptide of interest, the mRNA can be selected from among about 0.0001% to about 10%, about 1 to about 10%, about 5% to about 15%, about 10% to about 15%, about 10% to about 20%, about the 15% to about 20%, or any combination thereof, of the mRNA sequences in the ranked array with the lowest values for BPP. In other embodiments, when selecting a mRNA for reduced production of polypeptide of interest, the mRNA is selected from among about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination thereof, of the mRNA sequences in the ranked array with the lowest values for BPP.

The present invention additionally provides a method of selecting a mRNA for enhanced production of a polypeptide of interest, the method comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble for each individual mRNA sequence of (a); and c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the highest values for EFE and the lowest values for FMFE RNA secondary structure. In other embodiments, when selecting a mRNA for enhanced production of polypeptide of interest, the mRNA is selected from among about 0.0001% to about 10%, about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the highest values for EFE and the lowest values for FMFE RNA secondary structure.

In some aspects of the present invention, the method further comprises determining base pairing probability (BPP) for each individual mRNA sequence in addition to EFE and FMFE. Thus, when selecting a mRNA for enhanced production of a polypeptide of interest and BPP is determined and used in ranking the individual mRNA sequences of the array according to a joint distribution, then the mRNA is selected from among about 0.0001% to about 20% of sequences in the ranked array with the highest values for BPP. Thus, in additional aspects of the invention, when selecting a mRNA for enhanced production of polypeptide of interest, the mRNA can be selected from among about 0.0001% to about 10%, about 1 to about 10%, about 5% to about 15%, about 10% to about 15%, about 10% to about 20%, about the 15% to about 20%, or any combination thereof, of the mRNA sequences in the ranked array with the highest values for BPP. In other embodiments, when selecting a mRNA for enhanced production of polypeptide of interest, the mRNA is selected from among about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the highest values for BPP.

In other embodiments, the present invention provides a method of selecting a mRNA for reduced production of a polypeptide of interest, the method comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble; c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the lowest values for EFE and the highest values for FMFE RNA secondary structure. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for EFE and the highest values for FMFE RNA secondary structure. In other embodiments, when selecting a mRNA for reduced production of polypeptide of interest, the mRNA is selected from among about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the lowest values for EFE and the highest values for FMFE RNA secondary structure.

In additional aspects of the present invention, the method further comprises determining base pairing probability (BPP) for each individual mRNA sequence in addition to EFE and FMFE. Thus, when selecting a mRNA for reduced production of a polypeptide of interest and BPP is determined and used in ranking the individual mRNA sequences of the array according to a joint distribution, then the mRNA is selected from among about 0.0001% to about 20% of sequences in the ranked array with the lowest values for BPP. Thus, in additional aspects of the invention, when selecting a mRNA for reduced production of polypeptide of interest, the mRNA can be selected from among about 0.0001% to about 10%, about 1% to about 10%, about 5% to about 15%, about 10% to about 15%, about 10% to about 20%, about the 15% to about 20%, or any combination thereof, of the mRNA sequences in the ranked array with the lowest values for BPP. In other embodiments, when selecting a mRNA for reduced production of polypeptide of interest, the mRNA is selected from among about 0.0001%, 0.0005%, 0.001%, 0.005%, 0.01%, 0.05%, 1%, 2%, 3%, 4%, 5%, 6%, 7%, 8%, 9%, 10%, 11%, 12%, 13%, 14%, 15%, 16%, 17%, 18%, 19%, 20%, or any combination e thereof, of the mRNA sequences in the ranked array with the lowest values for BPP.

The selected mRNAs of the present invention can be further modified for protein production. As an example, the base pairing in and/or around the start codon (AUG) of a selected mRNA coding for the polypeptide of interest can be further modified to make the start codon of the selected mRNA more open (e.g., having fewer or no base pairings for enhanced protein production/translation initiation) or less open (e.g, having more base pairings for decreased protein production/translation initiation). The amount of base pairing of the start codon of the selected mRNA (i.e., more or less open) is in comparison to the start codon of the wild-type (native) mRNA that encodes for the polypeptide of interest or in comparison to the start codon of a second mRNA that encodes the polypeptide (other than the selected mRNA (e.g., first mRNA)). In further embodiments of the present invention, the selected mRNAs of the present invention can be combined with other factors that modify protein production such as transcription and translation enhancers.

In some embodiments of this invention, to achieve the desired level of protein production, the selected mRNA sequences are further altered (i.e., mutated) so that the encoded amino acid sequence of the polypeptide of interest is mutated to incorporate one or more nonconsequential mutations (e.g., one or more conservative amino acid substitutions), which result in a desired change in the MFE value of the mRNA and a corresponding desired change in the level of protein production. Thus, while the mutated mRNA sequence encodes a mutated amino acid sequence, the mutation in the amino acid sequence does not alter the function of the polypeptide as compared to the wild type polypeptide sequence.

Thus, in some embodiments of the present invention, a method for modifying the production of a polypeptide of interest in a cell of an organism is provided, the method comprising: (a) selecting an mRNA encoding a polypeptide of interest according to any of the preceding claims; (b) mutating the nucleotide sequence of the mRNA of (a) to produce a mutated mRNA having an enhanced or reduced MFE RNA secondary structure as compared to the MFE RNA secondary structure of the nucleotide sequence of the mRNA of (a)) and encoding a polypeptide sequence that is mutated compared to the polypeptide sequence encoded by the mRNA of (a); wherein the mutated polypeptide sequence retains the function of the polypeptide encoded by the mRNA of (a), and expression of the mutated mRNA sequence in a cell of an organism results in modified production of the polypeptide of interest as compared to the wild-type mRNA sequence.

Figure 2:
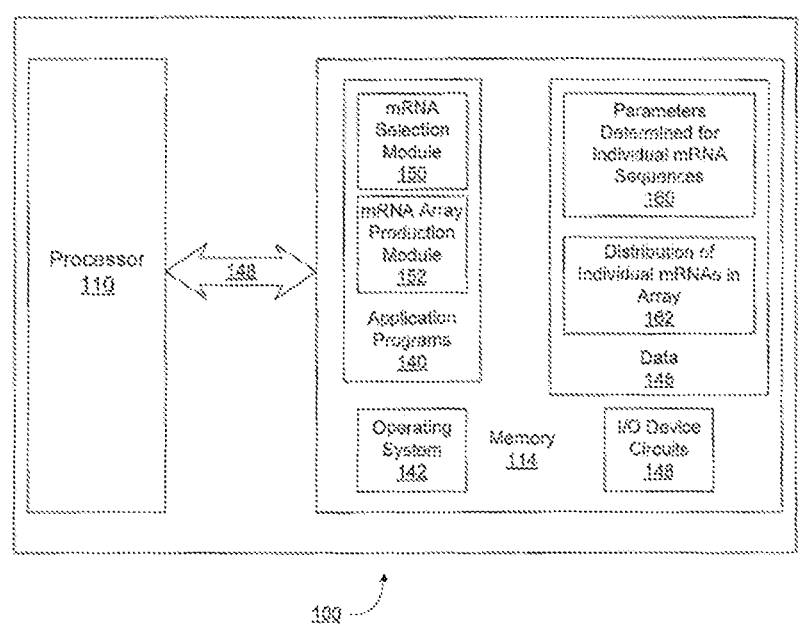
FIG. 2 is a block diagram illustrating systems according to some embodiments of the invention.

Conservative or nonconsequential mutations include point mutations (replacement of a single base nucleotide with another nucleotide). The types of point mutations that can result in nonconsequential mutations (i.e., do not affect function) are well known in the art (See, e.g., D. Bordo and P. Argos, Suggestions for "Safe" Residue Substitutions in Site-Directed Mutagensis, J. Mol. Biol. 217:721-729 (1991); FIG. 2). Thus, for example, an array of mRNA sequences can be generated in which conservative point mutations are introduced into the mRNA sequence and from this array a mRNA having a desired MFE value and encoding a polypeptide that is mutated but retains the wild type function (e.g., nonconsequential mutation) can be selected. Thus, the MFE of a selected mRNA of the present invention can be further manipulated by mutating the sequence of the mRNA with the mutation resulting in a nonconsequential mutation in the polypeptide. Such mutations provide additional flexibility in choice of mRNA sequence for use in achieving a desired level of protein production.

In further embodiments, the polypeptide of interest may be further optimized by using preferred codons for improved expression in a particular organism of interest, or may be synthesized using codons at a preferred codon usage frequency. Thus, in some embodiments, the GC content of the gene will be increased. See, e.g., Campbell & Gowri (1990) *Plant Physiol.* 92:1-11 for a discussion of host-preferred codon usage.

Alternatively, rare codons, which are known to impeded or slow translation, can be useful for modulating (e.g., reducing) protein production relative to the protein production of a wild-type mRNA or another selected mRNA. Rare codons are determined based on the particular species (i.e., particular codons may be rare in one species but not rare in another species). Thus, as used herein, a "rare codon" is a codon that is encoded by a tRNA having an abundance of less than about 15% of the total tRNAs that code for a particular amino acid in a particular species or cell-type within a species. Accordingly, in some embodiments of this invention, the individual mRNA sequences selected according to the methods of this invention can comprise one or more rare codons near the start codon. Alternatively, in other embodiments of this invention mRNA sequences comprising rare codons can be eliminated from the array Elimination of sequences comprising rare codons can be done using software programs.

As used herein, "near the start codon" means those codons encoding the first 12 amino acids (AUG to +12 amino acids). On the polypeptide level, "near the start codon" comprises nucleotide 1 to +36.

As used herein, "a," "an" or "the" can mean one or more than one. For example, "a" cell can mean a single cell or a multiplicity of cells.

As used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound (e.g., mRNA) or agent of this invention, dose, time, percentage, temperature, and the like, is meant to encompass variations of ±20%, ±10%, ±5%, ±1%, ±0.5%, or even ±0.1% of the specified amount.

As used herein, the term "polypeptide" encompasses both peptides and proteins, unless indicated otherwise.

As used herein, an "isolated" polypeptide or polypeptide fragment means a polypeptide or polypeptide fragment separated or substantially free from at least some of the other components of the naturally occurring organism, for example, the cellular components or other polypeptides or nucleic acids commonly found associated with the polypeptide.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "reduce," "reduced," "reducing," "reduction," "diminish," and "decrease" (and grammatical variations thereof), as used herein, describe a decrease in the production of a polypeptide of interest encoded by a selected mRNA. This decrease can be observed by comparing the production of a polypeptide of interest by the selected mRNA to the production of the polypeptide of interest by the wild-type (i.e., native) mRNA that encodes for the same polypeptide of interest or by comparing the production of a polypeptide of interest by the selected mRNA to the production of the polypeptide by another (second) mRNA (other than the selected (first) mRNA) that encodes the same polypeptide of interest as encoded by the selected mRNA.

The terms "enhance," "enhanced," "enhancing," "enhancement," and "increase," (and grammatical variations thereof), as used herein, describe an increase in the production of polypeptide of interest encoded by a selected mRNA. This increase can be observed by comparing the production of a polypeptide of interest by the selected mRNA to the production of the polypeptide of interest by the wild-type (i.e., native) mRNA that encodes for the same polypeptide of interest as encoded by the selected mRNA or by comparing the production of a polypeptide of interest by the selected mRNA to the production of the polypeptide by another (second) mRNA (other than the selected (first) mRNA) that encodes the same polypeptide of interest as encoded by the selected mRNA.

The term "modulate," "modulates," modulated" or "modulation" refers to enhancement (e.g., an increase) or inhibition (e.g., a reduction) in the specified activity (e.g., modulated protein production).

A polypeptide of interest can be any polypeptide. Non-limiting examples of polypeptides of interest that are suitable for expression in plants include those resulting in agronomically important traits such as herbicide resistance, virus resistance, bacterial pathogen resistance, insect resistance, nematode resistance, and fungal resistance. See, e.g., U.S. Pat. Nos. 5,569,823; 5,304,730; 5,495,071; 6,329,504; and 6,337,431. The polypeptide of interest may also be one that results in increases in plant vigor or yield (including polypeptides that allow a plant to grow at different temperatures, soil conditions and levels of sunlight and precipitation), or one that allows identification of a plant exhibiting a trait of interest (e.g., selectable marker gene, seed coat color, etc.).

Herbicide resistance is also sometimes referred to as herbicide tolerance. Genes conferring resistance to an herbicide that inhibits the growing point or meristem, such as an imidazalinone or a sulfonylurea can be suitable. Exemplary genes in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a gene encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides of interest encoded by genes for resistance to glyphosate are also suitable. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Genes for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable herbicides include those that inhibit photosynthesis, such as a triazine and a benzonitrile (nitrilase). See, U.S. Pat. No. 4,810,648. Other suitable herbicides include 2,2-dichloropropionic acid, sethoxydim, haloxyfop, imidazolinone herbicides, sulfonylurea herbicides, triazolopyrimidine herbicides, s-triazine herbicides and bromoxynil. Also suitable are genes that confer resistance to a protox enzyme, or provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Application Publication No. 2001/0016956 and U.S. Pat. No. 6,084,155.

The insecticidal proteins useful for the invention may be expressed in an amount sufficient to control insect pests, i.e., insect controlling amounts. It is recognized that the amount of expression of insecticidal protein in a plant necessary to control insects may vary depending upon the cultivar, type of insect, environmental factors and the like. Genes useful for insect or pest resistance include, for example, genes encoding toxins identified in *Bacillus* organisms. Genes encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1Fa, Cry3A, Cry9A, Cry9C and Cry9B; as well as genes encoding vegetative insecticidal proteins such as Vip1, Vip2 and Vip3). A full list of Bt toxins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides of interest that are suitable for expression in plants further include those that improve or otherwise facilitate the conversion of harvested cane into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the heterologous expression of a cellulase enzyme).

In one embodiment, the polypeptide of interest contributes to improved digestibility for food or feed. Xylanases are hemicellulolytic enzymes that improve the breakdown of plant cell walls, which leads to better utilization of the plant nutrients by the animal. This leads to improved growth rate and feed conversion. Also, the viscosity of the feeds containing xylan can be reduced. Expression of xylanases in plant cells also can also potentially act to facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases," Espoo; Souminen and Reinikainen, eds. (1993) *Foundation for Biotechnical and Industrial Fermentation Research* 8:125-135; U.S. Patent Application Publication No. 2005/0208178; and WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In another embodiment, the polypeptide of interest is a polysaccharide degrading enzyme. Such plants may be useful for generating, for example, fermentation feedstocks for bioprocessing. In some embodiments, the enzymes useful for fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as α-amylases (EC 3.2.1.1), glucuronidases (E.C. 3.2.1.131); exo-1,4-α-D glucanases such as amyloglucosidases and glucoamylase (EC 3.2.1.3), β-amylases (EC 3.2.1.2), α-glucosidases (EC 3.2.1.20), and other exo-amylases; and starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-β-D-glucanase (EC 3.2.1.39), β-glucosidase (EC 3.2.1.21); c) L-arabinases, such as endo-1,5-α-L-arabinase (EC 3.2.1.99), α-arabinosidases (EC 3.2.1.55) and the like; d) galactanases such as endo-1,4-β-D-galactanase (EC 3.2.1.89), endo-1,3-β-D-galactanase (EC 3.2.1.90), α-galactosidase (EC 3.2.1.22), β-galactosidase (EC 3.2.1.23) and the like; e) mannanases, such as endo-1,4-β-D-mannanase (EC 3.2.1.78), β-mannosidase (EC 3.2.1.25), α-mannosidase (EC 3.2.1.24) and the like; f) xylanases, such as endo-1,4-β-xylanase (EC 3.2.1.8), β-D-xylosidase (EC 3.2.1.37), 1,3-β-D-xylanase, and the like; g) other enzymes such as α-L-fucosidase (EC 3.2.1.51), α-L-rhamnosidase (EC 3.2.1.40), levanase (EC 3.2.1.65), inulanase (EC 3.2.1.7), and the like.

Further additional enzymes which may be used include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of interest are cellobiohydrolase (CBH) enzymes (EC 3.2.1.91). In one embodiment, the cellobiohydrolase enzyme is CBH1 or CBH2.

Other enzymes (polypeptides of interest) include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

In some embodiments of this invention, a polypeptide of interest further comprises a leader peptide. As is well known in the art, a leader peptide is a peptide that is encoded upstream (5' end of the coding sequence) of a larger open reading frame. Any leader peptide can be used with the methods of the present invention. A leader peptide can be a peptide that is found in nature or it can be a synthetic peptide designed to function as a leader peptide.

Thus, in some embodiments of the present invention, a polypeptide of interest comprises a leader peptide, and thus the 5' end of the mRNA encoding the polypeptide of interest comprises a leader sequence encoding the leader peptide upstream (5' end of the coding sequence) of an open reading frame. Thus, in some embodiments, the array of individual mRNA sequences comprising different nucleotide sequences encoding the polypeptide of interest encode a leader sequence fused to the polypeptide of interest. In some embodiments, the production of a polypeptide of interest can be modulated through the modulation of the expression of a leader sequence fused to the polypeptide of interest. Thus, a mRNA encoding the leader peptide is selected according to any of the methods of the present invention and fused to the polypeptide of interest. By modulating the expression of the leader sequence, the expression of the polypeptide to which it is fused can be modulated. Thus, the expression of the polypeptide of interest can be modulated without altering the nucleotide sequence encoding the polypeptide of interest or the amino acid sequence of the polypeptide of interest.

Non-limiting examples of leader peptides include signal peptides, transit peptides, targeting peptides, signal sequences, and the like. As is well known in the art, signal/transit peptides target or transport a protein encoded by a nuclear gene to a particular organelle such as the mitochondrion, plastids (e.g., apicoplast, chromoplast, chloroplast, cyanelle, thylakoid, amyloplast, and the like), microbodies (e.g., single membrane-bounded small organelles, such as peroxisomes, hydrogenosomes, glyoxysomes and glycosome).

Leader peptides are well known in the art and can be found in public databases such as the "Signal Peptide Website: An Information Platform for Signal Sequences and Signal Peptides." (www.signalpeptide.de); the "Signal Peptide Database" (proline.bic.nus.edu.sg/spdb/index.html) (Choo et al., BMC Bioinformatics 6:249 (2005)(available on www.biomedcentral.com/1471-2105/6/249/abstract); ChloroP (www.cbs.dtu.dk/services/ChloroP/; predicts the presence of chloroplast transit peptides (cTP) in protein sequences and the location of potential cTP cleavage sites); LipoP (www.cbs.dtu.dk/services/LipoP/; predicts lipoproteins and signal peptides in Gram negative bacteria); MITOPROT (ihg2.helmholtz-muenchen.de/ihg/mitoprot.html; predicts mitochondrial targeting sequences); PlasMit (gecco.org.chemie.uni-frankfurt.de/plasmit/index.html; predicts mitochondrial transit peptides in *Plasmodium falciparum*); Predotar (urgi.versailles.inra.fr/predotar/predotar.html; predicts mitochondrial and plastid targeting sequences); PTS1 (mendel.imp.ac.at/mendeljsp/sat/ptsl/PTS1predictor.jsp; predicts peroxisomal targeting signal 1 containing proteins); SignalP (www.cbs.dtu.dk/services/SignalP/; predicts the presence and location of signal peptide cleavage sites in amino acid sequences from different organisms: Gram-positive prokaryotes, Gram-negative prokaryotes, and eukaryotes. The method incorporates a prediction of cleavage sites and a signal peptide/non-signal peptide prediction based on a combination of several artificial neural networks and hidden Markov models); and TargetP (www.cbs.dtu.dk/services/TargetP/); predicts the subcellular location of eukaryotic proteins—the location assignment is based on the predicted presence of any of the N-terminal presequences: chloroplast transit peptide (cTP), mitochondrial targeting peptide (mTP) or secretory pathway signal peptide (SP)). (See also, von Heijne, G., *Eur J Biochem* 133 (1) 17-21 (1983); Martoglio et al. *Trends Cell Biol* 8 (10):410-5 (1998); Hegde et al. *Trends Biochem Sci* 31(10):563-71 (2006); Dultz et al. *J Biol Chem* 283(15):9966-76 (2008); Emanuelsson et al. *Nature Protocols* 2(4) 953-971(2007); Zuegge et al. 280(1-2):19-26 (2001); Neuberger et al. *J Mol Biol.* 328(3):567-79 (2003); and Neuberger et al. *J Mol Biol.* 328(3):581-92 (2003)).

Specific non-limiting examples of transit peptides are provided in Table 1.

TABLE 1

Leader peptides that target proteins to various organelles including the chloroplast, endoplasmic reticulum, peroxisome, mitochondria and vacuole.

| Transit Peptide | Source Protein/ Organism | Target Sub-Cellular Compartment | Amino Acid Sequence |
|---|---|---|---|
| xFNR | | Chloroplast | mafvasvpvfanasglkteakvcqkpalknsffrgeevtsrsffasqavsakpattg evdttir (SEQ ID NO: 105) |
| Cyt-0550 | *Synechococcus* sp. PCC 7002 | Chloroplast | MNKILGIDPLKKPIFGISAFVLLFWQLNVGAANA (SEQ ID NO: 106) |
| Cyt-553 | *Synechocystis* sp. PCC 6803 | Chloroplast | MFKLFNQASRIFFGIALPCLIFLGGIFSLGNTALA (SEQ ID NO: 107) |
| PSAF | *Synechocystis* sp. PCC 6803 | Chloroplast | MKHLLALLLAFTLWFNFAPSASA (SEQ ID NO: 108) |
| P28 | *Chlamydomonas reinhardtii* | Chloroplast | MALVARPVLSARVAASRPRVAARKAVRVSA (SEQ ID NO: 109) |
| P30 | *Chlamydomonas reinhardtii* | Chloroplast | MQALSSRVNIAAKPQRAQRLVVRA (SEQ ID NO: 110) |
| P35 | *Chlamydomonas reinhardtii* | Chloroplast | MQTLASRPSLRASARVAPRRAPRVAVVTKA (SEQ ID NO: 111) |
| P37 | *Chlamydomonas reinhardtii* | Chloroplast | MQALATRPSAIRPTKAARRSSVVVRA (SEQ ID NO: 112) |
| SSRub | *Chlamydomonas reinhardtii* | Chloroplast | MAAVIAKSSVSAAVARPARSSVRPMAALKPAVKAAPVAAPAQANQ (SEQ ID NO: 113) |
| ATPase | *Chlamydomonas reinhardtii* | Chloroplast | MAAMLASKQGAFMGRSSFAPAPKGVASRGSLQVV (SEQ ID NO: 114) |
| Cyt-C6 | *Cyanophora paradoxa* | Chloroplast | MAAFVAALPVIPSKAFIAGKADVAKAPVATNKGGVRM (SEQ ID NO: 115) |
| EPSPS | *Dunaliella sauna* | Chloroplast | MLARQGGSLRASQCNAGLARRVEVGALVVPRPISVNDVVPHVYSAPLSVARRSCSKS SIRSTRRLQTTVCSATLAAHSAP (SEQ ID NO: 116) |

TABLE 1-continued

Leader peptides that target proteins to various organelles including the chloroplast, endoplasmic reticulum, peroxisome, mitochondria and vacuole.

| Transit Peptide | Source Protein/ Organism | Target Sub-Cellular Compartment | Amino Acid Sequence |
|---|---|---|---|
| Optimized Transit Peptide | | Chloroplast | MASISSSVATVSRTAPAQANMVAPFTGLKSNAAFPTTKKANDFSTLPSNGGRVQCMQ VWPAYGNKKFETLSYLPPLSMAPTVMMASSATAVAPFQGLKSTASLPVARRSSRSLG NVSNGGRIRC (SEQ ID NO: 117) |
| γ-Zein signal sequence | Maize gamma Zein 27 KDa protein signal sequence | Endoplasmic Reticulum | MRVLLVALALLALAASAT (SEQ ID NO: 118) |
| ER targeting signal | | Endoplasmic Reticulum | MetMetSerPheValSerLeuLeuLeuValGlyIleLeuPheTrpAlaThrGluAla GluGlnLeuThrLysCysGuValPheGln (SEQ ID NO: 119) |
| PTS2 | | Peroxisome | Arg-Leu-X$_5$-His-Leu- (X = any amino acid) (SEQ ID NO: 120) |
| Mitochondrial targeting signal | | Mitochondria | MetLeuSerLeuArgGlnSerIleArgPhePheLysProAlaThrArgThrLeuCys SerSerArgTyrLeuLeu (SEQ ID NO: 121) |
| Mitochondrial targeting signal | NADH-ubiquinone oxidoreductase, *Bos taurus* | Mitochondria | MLRIPVRKALVGLSKSSKGCVRT (SEQ ID NO: 122) |
| xZmSOD3.1-01 | Maize Superoxide Dismutase, SOD 3.1 gene | Mitochondria | MALRTLASKKVLSFPFGGAGRPLAAAASAR (SEQ ID NO: 123) |
| xZmHSP60-01 | Maize heat shock protein, HSP60 | Mitochondria matrix | MAYRAAASLASKARQAGNSLATRQVGSRLAWSR (SEQ ID NO: 124) |
| Sporamin N-terminal Pro-peptide 37 AA | Sweet potato, | Vacoular targeting | MKAFTLALFLALSLYLLPNPAHSRFNPIRLPTTHEPA (SEQ ID NO: 125) |
| xOsGlobVTS-01 | Rice Globulin Vacuole Targeting Signal | signal Protein storage vacuole | MQLSESEMRFRDRQCQREVQD (SEQ ID NO: 126) |

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides.

Nucleic acids of this invention can comprise a nucleotide sequence that can be identical in sequence to the sequence which is naturally occurring (i.e., native or wild type) or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained. A nucleic acid of this invention can be single or double stranded. Additionally, the nucleic acids of this invention can also include a nucleic acid strand that is partially complementary to a part of the nucleic acid sequence or completely complementary across the full length of the nucleic acid sequence. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

As used herein, the term "gene" refers to a nucleic acid molecule capable of being used to produce mRNA or antisense RNA. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous).

Thus, an "isolated nucleic acid" is a nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid encoding an additional polypeptide or peptide sequence.

The term "transgene" as used herein, refers to any nucleic acid sequence used in the transformation of a plant, animal, or other organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.*, 2:482-489, 1981, Smith et al., *Nucleic Acids Res.* 11:2205-2220, 1983).

Useful methods for determining sequence identity are also disclosed in Guide to Huge Computers (Martin J. Bishop, ed., Academic Press, San Diego (1994)), and Carillo, H., and Lipton, D., (*Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institute of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and, for polynucleotide sequence BLASTN can be used to determine sequence identity.

As used herein, the term "promoter" refers to a region of a nucleotide sequence that incorporates the necessary signals for the efficient expression of a coding sequence. This may include sequences to which an RNA polymerase binds, but is not limited to such sequences and can include regions to which other regulatory proteins bind together with regions involved in the control of protein translation and can also include coding sequences.

Furthermore, a "promoter" of this invention is a promoter capable of initiating transcription in a cells of an organism of interest (e.g., animal, plant, microorganism). Such promoters include those that drive expression of a nucleotide sequence constitutively, those that drive expression when induced, and those that drive expression in a tissue- or developmentally-specific manner, as these various types of promoters are known in the art.

The term "transformation" as used herein refers to the introduction of a heterologous nucleic acid into a cell. Transformation of a cell may be stable or transient. The term "transient transformation" or "transiently transformed" refers to the introduction of one or more heterologous nucleic acids into a cell wherein the heterologous nucleic acid is not heritable from one generation to another.

"Stable transformation" or "stably transformed" refers to the integration of the heterologous nucleic acid into the genome of the organism or incorporation of the heterologous nucleic acid into the cell or cells of the organism (e.g., via a plasmid) such that the heterologous nucleic acid is heritable across repeated generations. Thus, in one embodiment of the present invention a stably transformed organism is produced. In other embodiments of the present invention a stably transformed plant is produced.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

A nucleic acid (e.g., selected mRNA) of this invention can be introduced into a cell by any method known to those of skill in the art. In some embodiments of the present invention, transformation of a cell comprises nuclear transformation. In other embodiments, transformation of a cell comprises plastid transformation (e.g., chloroplast transformation). Thus, mRNAs selected according to the methods of the present invention can be used to transform any organism using methods know to those of skill in the art.

Procedures for transforming a wide variety of organisms, including, but not limited to, a bacteria, a cyanobacteria, an animal, a plant, a fungus, and the like, are well known in the art and are described throughout the literature.

As an example, such methods for transformation of plants include, but are not limited to, transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, electroporation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

The term "vector" refers to a composition for transferring, delivering or introducing a nucleic acid (or nucleic acids) into a cell. A vector comprises a nucleic acid comprising the nucleotide sequence to be transferred, delivered or introduced. In some embodiments, a vector of this invention can be a viral vector, which can comprise, e.g., a viral capsid and/or other materials for facilitating entry of the nucleic acid into a cell and/or replication of the nucleic acid of the vector in the cell (e.g., reverse transcriptase or other enzymes which are packaged within the capsid, or as part of the capsid). The viral vector can be an infectious virus particle that delivers nucleic acid into a cell following infection of the cell by the virus particle.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

Thus, in some embodiments of this invention, a mRNA encoding a polypeptide of interest selected using the methods described herein can be introduced into a eukaryotic cell to produce a transgenic eukaryotic cell or transgenic eukaryotic organism that thereby produces an enhanced or diminished amount of the polypeptide of interest as compared to the amount of protein produced by the wild-type (i.e., native) mRNA encoding the same polypeptide of interest as the mRNA selected according to the methods of this invention. In other embodiments of this invention, a first mRNA encoding a polypeptide of interest selected using the methods described herein can be introduced into a eukaryotic cell to produce a transgenic eukaryotic cell or transgenic eukaryotic organism that thereby produces an enhanced or diminished amount of the polypeptide of interest as compared to the amount of protein produced by a second mRNA selected using the methods described herein and encoding the same polypeptide of interest as the first mRNA.

In further embodiments, a mRNA encoding a polypeptide of interest selected using the methods described herein can be used as described herein to modify (enhance or reduce) the protein production of an endogenous nucleotide sequence (e.g., present in the genome) encoding the same polypeptide of interest as that encoded by the mRNA that is selected using the methods described herein. Thus, in some embodiments of this invention, a method for modifying the production of a polypeptide of interest in a cell of an organism is provided, the method comprising: (a) selecting a mRNA encoding a polypeptide of interest according to the methods of this invention; (b) identifying the differences between the nucleotide sequence of the mRNA selected according to (a) and a wild-type endogenous nucleotide sequence of said organism, wherein the wild-type endogenous nucleotide sequence encodes a polypeptide of interest that is the same as that encoded by the mRNA selected according to (a); and (c) mutating in situ the endogenous nucleotide sequence encoding the polypeptide of interest to incorporate each of the nucleotide differences identified in (b) into the endogenous nucleotide sequence, whereby the production of the polypeptide of interest from the in situ mutated endogenous nucleotide sequence in the cell of the organism is modified. Methods of in situ modification of nucleotide sequences are known in the art. Thus, for example, zinc finger nucleases can be used as described by Cai et al. (*Plant Mol Biol.* 69(6):699-709 (2009)) to drive site directed DNA integration into native nucleotide sequences.

Gene targeting and genomic DNA modification may also be accomplished through use of activator-like (TAL) effector nucleases as is known by those skilled in the art. WO10054348, Shornack, S. et al. *Gene-for gen mediated recognition of nuclear-targeted AvrBs-like bacterial effector proteins*, Journal of Plant Physiology, 163 (2006) 256-272, Boch et al., *Breaking the code of DNA binding specificity of TAL-type III effectors*, Science, Vol 326, December 2009.

A transgenic organism is also provided herein, comprising, consisting essentially of and/or consisting of one or more nucleic acid constructs of this invention. A transgenic organism is additionally provided herein comprising a transformed cell of this invention. In particular embodiments, a transgenic plant is also provided, comprising, consisting essentially of and/or consisting of one or more nucleic acid constructs of this invention. A transgenic plant is additionally provided herein comprising a transformed plant cell of this invention.

Additionally provided herein is a transgenic seed, a transgenic pollen grain and a transgenic ovule of the transgenic plant of this invention. Further provided is a tissue culture of regenerable transgenic cells of the transgenic plant of this invention.

The present invention further provides a method of selecting an mRNA for enhanced production of a polypeptide of interest, the method comprising determining a nucleotide sequence of a mRNA encoding the polypeptide of interest, wherein the mRNA has a secondary structure comprising fewer than four base paired nucleotides and a start codon comprising no base paired nucleotides.

Additionally provided herein is method of selecting an mRNA for reduced production of a polypeptide of interest, the method comprising determining a nucleotide sequence of a mRNA encoding the polypeptide of interest, wherein the mRNA has a secondary structure comprising at least six base paired nucleotides and a start codon comprising at least one base pair.

In further embodiments, the present invention provides computer-implemented methods of selecting a mRNA for production of a polypeptide of interest, the method comprising: a) producing an array of individual mRNA sequences comprising different nucleotide sequences encoding the polypeptide of interest; b) determining one or more of the following parameters for each individual mRNA sequence of (a): (i) ensemble free energy (EFE); (ii) frequency of the minimum free energy (FMFE) RNA secondary structure in a thermodynamic ensemble; and (iii) ensemble diversity (ED); c) ranking the individual mRNA sequences of the array according to the parameters determined in step (b); and d) selecting a mRNA sequence from the ranked array of step (c), wherein the selected mRNA produces the polypeptide of interest.

In additional embodiments, the present invention provides a computer-implemented method of selecting a mRNA for production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

In other embodiments, the present invention provides a computer-implemented method of selecting a mRNA for production of a polypeptide of interest, the method comprising: a) producing an array of individual mRNA sequences comprising different nucleotide sequences encoding the polypeptide of interest; b) determining ensemble free energy (EFE) for each individual mRNA sequence of (a); c) determining one or more of the following parameters for each individual mRNA sequence of (a): (i) frequency of the minimum free energy (FMFE) RNA secondary structure in a thermodynamic ensemble; and (ii) ensemble diversity (ED); d) ranking the individual mRNA sequences of the array according to a joint distribution of the parameters determined in (b) and (c) above; and e) selecting a mRNA sequence from the ranked array of step (d), wherein the selected mRNA produces the polypeptide of interest.

Embodiments according to the present invention provide a computer-implemented method of selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the highest values for MFE RNA secondary structure and the lowest values for FMFE RNA secondary structure or the mRNA sequence is selected from among the mRNA sequences having an MFE RNA secondary structure in a range from about 0 kcal/mol to about −2 kcal/mol as measured at room temperature and the lowest values for FMFE RNA secondary structure, wherein expression of the selected mRNA sequence results in enhanced production of the polypeptide of interest as compared to the wild-type mRNA sequence.

In other embodiments, a computer-implemented method of selecting a mRNA for reduced production of a polypeptide of interest is provided, the method comprising: a) producing an array of individual mRNA sequences comprising different nucleotide sequences encoding the polypeptide of interest; b) determining minimum free energy (MFE) RNA secondary structure for each individual mRNA sequence of (a) and frequency of the minimum free energy (FMFE) RNA secondary structure in a thermodynamic ensemble for each individual mRNA sequence of (a); c) ranking the individual mRNA sequences of the array according to a joint distribution of the MFE and FMFE determined in step (b) above; and d) selecting a mRNA sequence from the ranked array of step (c), wherein the mRNA is selected from among about 0.0001% to about 20% of sequences in the ranked array with the lowest values for MFE RNA secondary structure and the highest values for FMFE RNA secondary structure or the mRNA sequence is selected from among the mRNA sequences having an MFE RNA secondary structure in a range from about −9 kcal/mol to about −18 kcal/mol as measured at room temperature and the highest values for FMFE RNA secondary structure, wherein expression of the selected mRNA sequence results in reduced production of the polypeptide of interest as compared to the wild-type mRNA sequence.

In still other embodiments of the invention a computer-implemented method is provided for selecting a mRNA for enhanced production of a polypeptide of interest, the method comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble for each individual mRNA sequence of (a); and c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the highest values for EFE and the lowest values for FMFE RNA secondary structure.

Additional embodiments of the invention provide a computer-implemented method of selecting a mRNA for reduced production of a polypeptide of interest, the methods comprising: a) producing an array of individual mRNA sequences comprising different nucleotide sequences encoding the polypeptide of interest; b) determining ensemble free energy (EFE) for each individual mRNA sequence of (a) and frequency of the minimum free energy (FMFE) RNA secondary structure in a thermodynamic ensemble; c) ranking the individual mRNA sequences of the array according to a joint distribution of the EFE and FMFE determined in step (b) above; and d) selecting a mRNA sequence from the ranked array of step (c), wherein the mRNA is selected from among about 0.0001% to about 20% of sequences in the ranked array with the lowest values for EFE and the highest values for FMFE RNA secondary structure.

The present invention further provides a computer-implemented method of selecting a mRNA for production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); c) ranking the individual mRNA sequences of the array according to the MFE RNA secondary structure determined in (b) from highest MFE RNA secondary structure to lowest MFE RNA secondary structure; and d) selecting a mRNA sequence from the ranked array of step (c), wherein the mRNA is selected from the group of mRNAs having a MFE RNA secondary structure in a range from about 0 kcal/mol to about −2 kcal/mol, the group of mRNAs having a MFE RNA secondary structure in a range from about −2 kcal/mol to about −9 kcal/mol, or the group of mRNAs having a MFE RNA secondary structure in a range from about −9 kcal/mol to about −18 kcal/mol, wherein the selected mRNA produces the polypeptide of interest.

Additionally provided is a computer-implemented method of selecting a mRNA for enhanced production of a polypeptide of interest, the method comprising: a) producing an array of individual mRNA sequences comprising different nucleotide sequences encoding the polypeptide of interest; b) determining minimum free energy (MFE) RNA secondary structure for each individual mRNA sequence of (a); and c) selecting a mRNA sequence of (a) having an MFE RNA secondary structure in the range from about 0 kcal/mol to about −2 kcal/mol, wherein expression of the selected mRNA sequence results in enhanced production of the polypeptide of interest as compared to the wild-type mRNA sequence.

In additional aspects of this invention, a computer-implemented method of selecting a mRNA for reduced production of a polypeptide of interest is provided, the method comprising: a) producing an array of individual mRNA sequences comprising different nucleotide sequences encoding the polypeptide of interest; b) determining minimum free energy (MFE) RNA secondary structure for each individual mRNA sequence of (a) and the expression level of each individual mRNA sequence of (a); c) selecting a mRNA sequence of (a) having an MFE RNA secondary structure in the range from about −9 kcal/mol to about −18 kcal/MFE, wherein expression of the selected mRNA sequence results in enhanced production of the polypeptide of interest as compared to the wild-type mRNA sequence.

In some embodiments of the present invention, a computer-implemented method for modifying the production of a polypeptide of interest in a cell of an organism is provided, the method comprising: (a) selecting an mRNA encoding a polypeptide of interest according to the methods of this invention; (b) mutating the nucleotide sequence of the mRNA of (a) to produce a mutated mRNA having an enhanced or reduced MFE RNA secondary structure as compared to the MFE RNA secondary structure of the nucleotide sequence of the mRNA of (a)) and encoding a polypeptide sequence that is mutated compared to the polypeptide sequence encoded by the mRNA of (a); wherein the mutated polypeptide sequence retains the function of the polypeptide encoded by the mRNA of (a), and expression of the mutated mRNA sequence in a cell of an organism results in modified production of the polypeptide of interest as compared to the wild-type mRNA sequence.

In further embodiments of this invention, a computer-implemented method for modifying the production of a polypeptide of interest in a cell of an organism is provided, the method comprising: (a) selecting an mRNA encoding a polypeptide of interest according to the methods of this invention; (b) identifying the differences between the nucleotide sequence of the mRNA selected according to (a) and a wild-type endogenous nucleotide sequence of said organism, wherein the wild-type endogenous nucleotide sequence encodes a polypeptide of interest that is the same as that encoded by the mRNA selected according to (a); and (c) mutating in situ the endogenous nucleotide sequence encoding the polypeptide of interest to incorporate each of the nucleotide differences identified in (b) into the endogenous nucleotide sequence, whereby the production of the polypeptide of interest from the in situ mutated endogenous nucleotide sequence in the cell of the organism is modified.

In some embodiments, systems and/or computer program products for carrying out the methods described herein are provided. Accordingly, the present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Thus, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain or store the program for use by or in connection with the instruction execution system, apparatus, or device.

As illustrated in FIG. 1, operations according to some embodiments of the present invention include producing an array of mRNA sequences encoding a polypeptide of interest (Block 10). For example, an input amino acid sequence is selected and using a random sampling procedure nucleotide sequences encoding the input amino acid sequence are generated. Thermodynamic parameters are determined for each individual mRNA sequence in the array (Block 20). The parameter data is provided for each of the individual mRNA sequences of the array (Block 30). The individual mRNA sequences are ranked according to the value determined for each parameter (Block 40). In the case when more than one parameter is determined the ranking is according to a joint distribution of the parameters. A mRNA sequence is selected from the ranked mRNA sequences based on the level of protein production desired (Block 50). A desired level of protein production can be any level of protein production including greatly enhanced, enhanced, moderately enhanced, moderately reduced or reduced or greatly reduced protein production.

As illustrated in FIG. 2, a data processing system includes a processor 110. The processor 110 communicates with the memory 114 via an address/data bus 148. The processor 110 can be any commercially available or custom microprocessor. The memory 114 is representative of the overall hierarchy of memory devices containing the software and data used to implement the functionality of the data processing system 100. The memory 114 can include, but is not limited to, the following types of devices: cache, ROM, PROM, EPROM, EEPROM, flash memory, SRAM, and DRAM.

As shown in FIG. 2, the memory 114 may include several categories of software and data used in the data processing system: the application programs 140, the operating system 142; the input/output (I/O) device drivers 148; and the data 146. The application programs 140 can include a mRNA selection module 150 and/or a mRNA array production module 152. In the mRNA array production module 152, an input amino acid sequence may be used to generate an array of mRNA sequences encoding the input amino acid sequence. In the mRNA selection module 150, mRNAs may be ranked based on the values for the parameters determined for the individual mRNAs of the array, and a mRNA may be selected based on the desired level of protein production. The data 146 may include the parameter data determined for individual mRNA sequences for an array 160 and the distribution of the individual mRNAs in the array 162. The mRNA selection module 150 and the mRNA array production module 152 can be configured to carry out the operations discussed in FIG. 1.

As will be appreciated by those of skill in the art, the operating system 152 shown in FIG. 2 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or WindowsXP from Microsoft Corporation, Redmond, Wash., Unix or Linux or FreeBSD, Mac OS from Apple Computer, or proprietary operating systems. The I/O device drivers 148 typically include software routines accessed through the operating system 142 by the application programs 144 to communicate with devices such as I/O data port(s), data 146 and certain components of the memory 114 and/or the histology slide imaging system 120. The application programs 140 are illustrative of the programs that implement the various features of the data processing system 100 and can include at least one application which supports operations according to embodiments of the present invention. Finally, the data 140 represents the static and dynamic data used by the application programs 140, the operating system 142, the I/O device drivers 148, and other software programs that may reside in the memory 114.

While the present invention is illustrated, for example, with reference to the mRNA selection module 150 and the mRNA array production module 152 being application program in FIG. 2, as will be appreciated by those of skill in the art, other configurations may also be utilized according to embodiments of the present invention. For example, the mRNA selection module 150 may also be incorporated into the operating system 142, the I/O device drivers 148 or other such logical division of the data processing system 100.

Thus, the present invention should not be construed as limited to the configuration of FIG. 2, which is intended to encompass any configuration capable of carrying out the operations described herein.

The I/O data port can be used to transfer information between the data processing system 100 and another computer system or a network (e.g., the Internet) or to other devices controlled by the processor. These components may be conventional components such as those used in many conventional data processing systems that may be configured in accordance with the present invention to operate as described herein. Therefore, the mRNA selection module 150 can be used to analyze the parameter data determined for individual mRNA sequences for an array 160 and the distribution of individual mRNAs in the array 162 that has been previously collected.

The present invention will now be described with reference to the following examples. It should be appreciated that this example is for the purpose of illustrating aspects of the present invention, and does not limit the scope of the invention as defined by the claims.

EXAMPLES

Example 1. Outline of Methods (1) Generation of RNA folding energies for potential sequences encoding a test amino acid sequence
(2) Selection of the variants (some that are predicted to express protein at high level while others are predicted to result in inefficient protein expression)
(3) Generation of vector constructs of each variant for yeast expression and for tobacco transient expression
(4) Transformation (yeast and tobacco)
(5) Quantitative RT-PCR used to estimate the level of mRNA transcript (to normalize data protein expression data and reduce possible influence of variation(s) in transcription level)
(6) Collection of samples for measuring level of protein expression
(7) Quantitative ELISA
(8) Protein estimation to check the quality of the extract sample to be used in ELISA
(9) Western blot analysis to check for any possible post-translational modification of the expressed protein
(10) Data analysis to build a correlation between thermodynamic parameters of mRNA and level of protein expression.

Example 2. Methods for Generation of RNA Folding Energies for Potential Sequences Encoding a Given Amino Acid Sequence Starting with an input amino acid sequence, BioPerl was used to automate a random sampling procedure that generated nucleotide sequences encoding the input amino acid sequences. (Stajich et al. *Genome Res* 12(10):1611-8 (2002)). For each position in the amino acid sequence, codons for that position were selected by sampling the possible codons from a uniform distribution. Ten thousand nucleotide sequences were generated in this manner for each input amino acid sequence. Each output nucleotide sequence was checked for length and translation to ensure the accuracy of the sampling procedure. The ViennaRNA package version 1.8.2 was used to calculate for each input sequence the minimum free energy, ensemble free energy, and frequency of the MFE structure in the ensemble. (Hofacker et al. *Monatshefte f. Chemie* 125: 167-188 (1994); www.tbi-.univie.ac.at/RNA/). The parameter settings for calculation were "-p0-d2," which turns on calculation of the partition function and ensures that the partition function and the minimum free energy treat dangling end energies in the same manner Calculation of the energies was executed on the in-house Linux cluster. Histograms of the resulting energy distributions were plotted using R. (R Development Core Team. R: A language and environment for statistical computing. R Foundation for Statistical Computing, Vienna, Austria (2009); ISBN 3-900051-07-0; www.R-project.org).

Example 3. Selection of mRNA Variants (Both Enhanced and Reduced Protein Production)

The *Anemonia majano* cyan fluorescent protein (AmCyan reporter gene) with N-terminal chloroplast targeting signal polypeptide from *Chlamydomonas reinhardtii* was chosen as the polypeptide of interest. Selected mRNA variants were synthesized by GENEART® (Germany). Variants of the AmCyan nucleotide sequence were generated by replacing the coding sequence of the 5' region (N-terminal region of the encoded polypeptide). Thus, in this particular example, 40 nucleotides from the 5' end of the nucleotide sequence of the N-terminal signal peptide (upstream of AmCyan reporter sequence) were replaced with the sequences (variants) set forth in Table 2 and/or Table 3, below.

Construct for tobacco transformation and protein expression. A nucleic acid construct encoding the AmCyan nucleotide sequence (CFP) fused with the nucleotide sequence of a ssRubisco chloroplast transit peptide was used to transform tobacco. The nucleotide sequence (SEQ ID NO:1) of the construct and the amino acid sequence (SEQ ID NO:2) encoded by the construct are shown below.

(SEQ ID NO: 1)
CACC ATG gcc gcg gtc ata gcc aaa tca agc gtt tcc gca gccgtggcaaggcctgctagatctagcgtgaggccgatggctgcct tgaaacccgcagtcaaagcggcacctgtggcagctccagcacaagcgaat caggccctgagcaacaagacatcggcgacgacatgaagatgacctaccac atggacggctgcgtgaacggccactacttcaccgtgaagggcgagggcag cggcaagccatacgagggcacccagaccagcaccacaaggtgacgatggc caacggtgcccactggcatcagcttcgacatcctgagcaccgtgacatg tacggcaaccgctgcttcaccgcctacccgaccagcatgccggactactt caagcaggccttcccggacggcatgagctacgagcgcaccttcacctacg aggacggcggcgtggctaccgccagctgggagatcagcctgaagggcaac tgcttcgagcacaagagcaccaccacggcgtgaacttcccagccgacggc ccggtgatggccaagatgaccaccggctgggatccgagcttcgagaagat gactgtgtgcgacggcatcctgaagggcgacgtgaccgccttcctgatgc ttcaaggcggtggcaactaccgctgccagaccacaccagctacaagacca agaagccggtgaccatgccgccaaaccatgccgtggagcacaggatcgcc cgcaccgacctggacaagggcggcaacagcgtccagctgaccgagcacgc cgtggcccacatcaccagcgtggtgccgttctga -continued (SEQ ID NO: 2)
MALSNKFIGDDMKMTYHMDGCVNGHYFTVKGEGSGKPYEGTQTSTFKVTM

ANGGPLAFSFDILSTVFMYGNRCFTAYPTSMPDYFKQAFPDGMSYERTFT

YEDGGVATASWEISLKGNCFEHKSTFHGVNFPADGPVMAKKTTGWDPSFE

KMTVCDGILKGDVTAFLMLQGGGNYRCQFHTSYKTKKPVTMPPNHVVEHR

IARTDLDKGGNSVQLTEHAVAHITSVVPF

The ssRubisco chloroplast transit peptide is indicated in bold letters at the 5' end of SEQ ID NO:1. The bold and underlined nucleotides (also at the 5' end of the sequence) show the portion of SEQ ID NO:1 that is varied among the variants. Further, each variant comprises at its 5' end four nucleotides, CACC (in grey capitol letters), just up-stream of the ATG start codon. The nucleotide sequences used to generate the variants are set forth in Table 2 (SEQ ID NOs:5-26), below.

Clinong: A Laboratory Manual, Cold Spring Harbor Laboratory, Cold Spring Harbor, N.Y. (1989); Silhavy et al., *Experiments with Gene Fusions*, Cold Spring Harbor Laboratory, Cold Spring Harbor, N.Y. (1984); and Ausubel st al. *Current protocols in Molecular Biology*, Greene Publishing Assoc. and Wiley Interscience (1987))

Construct for yeast transformation and protein expression. A nucleic acid construct encoding the AmCyan nucleotide sequence was used to transform yeast (*Saccharomyces cerevisiae*). The AmCyan nucleotide sequences were digested with Xho1/Kpn1 and gel extracted. The single copy yeast expression vector, YpEB/peri_isomaltase/V5 was digested with Xho1/Kpn1 and the backbone was extracted. The fragments were ligated and competent cells were transformed. Colonies were picked and positives were identified by colony PCR and verified by restriction digestion analysis and sequencing.

The nucleotide sequence (SEQ ID NO:3) of the construct and the amino acid sequence (SEQ ID NO:4) encoded by the

TABLE 2

Variants of N-terminal ssRubisco chloroplast transit peptide with AmCyan (CFP) reporter gene (for tobacco expression).

| Variant # | Nucleotide Sequence [-4 to +35] | | MFE | EFE |
|---|---|---|---|---|
| 9532 | CACCATGGCAGCGGTGATTGCCAAATCATCGGTGTCAGCT | (SEQ ID NO: 5) | -17.40 | -17.56 |
| 5605 | CACCATGGCCGCGGTCATTGCGAAAAGCAGTGTGTCGGCC | (SEQ ID NO: 6) | -16.60 | -17.17 |
| 2198 | CACCATGGCGGCGGTTATTGCCAAGTCGTCCGTGAGTGCG | (SEQ ID NO: 7) | -16.60 | -16.81 |
| 6030 | CACCATGGCGGCGGTCATTGCTAAAAGCAGCGTGAGCGCC | (SEQ ID NO: 8) | -14.30 | -15.23 |
| 1386 | CACCATGGCCGCTGTGATCGCAAAGTCCAGCGTGTCAGCC | (SEQ ID NO: 9) | -14.30 | -14.51 |
| 8708 | CACCATGGCCGCGGTCATAGCGAAAAGCTCTGTTTCCGCA | (SEQ ID NO: 10) | -12.30 | -12.38 |
| 811 | CACCATGGCAGCCGTGATAGCTAAGTCGTCTGTCTCGGCT | (SEQ ID NO: 11) | -12.30 | -14.12 |
| 6408 | CACCATGGCAGCAGTGATCGCAAAGTCGAGCGTTAGTGCA | (SEQ ID NO: 12) | -10.20 | -10.27 |
| 3263 | CACCATGGCAGCCGTTATCGCTAAGAGTAGCGTGTCTGCT | (SEQ ID NO: 13) | -10.20 | -12.39 |
| 3143 | CACCATGGCAGCAGTAATCGCGAAATCAAGTGTTAGTGCA | (SEQ ID NO: 14) | -8.90 | -8.94 |
| 7925 | CACCATGGCAGCTGTTATTGCAAAGTCGTCCGTGAGTGCC | (SEQ ID NO: 15) | -8.90 | -11.17 |
| 8256 | CACCATGGCAGCTGTAATAGCAAAATCCTCTGTCTCAGCA | (SEQ ID NO: 16) | -7.40 | -7.51 |
| 3947 | CACCATGGCTGCCGTAATCGCAAAGTCGTCCGTGAGTGCG | (SEQ ID NO: 17) | -7.40 | -9.46 |
| 3909 | CACCATGGCAGCCGTAATCGCAAAGAGCAGCGTAAGTGCT | (SEQ ID NO: 18) | -5.20 | -7.11 |
| 7120 | CACCATGGCAGCTGTAATCGCAAAATCATCTGTCTCCGCA | (SEQ ID NO: 19) | -5.20 | -5.34 |
| 4261 | CACCATGGCCGCCGTGATAGCCAAGTCGTCAGTATCCGCT | (SEQ ID NO: 20) | -3.90 | -5.71 |
| 2159 | CACCATGGCCGCAGTAATAGCCAAATCTTCAGTTTCCGCC | (SEQ ID NO: 21) | -3.90 | -4.10 |
| 6682 | CACCATGGCAGCCGTAATAGCAAAATCATCAGTCAGCGCC | (SEQ ID NO: 22) | -2.30 | -2.85 |
| 5286 | CACCATGGCCGCCGTTATTGCAAAATCGTCTGTGTCTGCA | (SEQ ID NO: 23) | -2.30 | -4.20 |
| 1089 | CACCATGGCCGCCGTAATTGCTAAATCATCTGTCTCTGCC | (SEQ ID NO: 24) | -1.40 | -2.33 |
| 6096 | CACCATGGCCGCCGTAATAGCAAAGAGTTCCGTATCCGCA | (SEQ ID NO: 25) | -1.40 | -2.99 |
| 7397 | CACCATGGCTGCCGTTATTGCAAAATCTTCTGTTTCCGCT | (SEQ ID NO: 26) | -0.80 | -2.73 |

MFE = minimum free energy; EFE = ensemble free energy

The nucleotide sequences were generated using standard recombinant DNA and molecular cloning techniques that are well known in the art (See, e.g., Sambrook et al. Molecular construct are shown below. In this case, in contrast to the construct used for plant expression, the construct used in yeast expression does not have an N-terminal transit peptide.

(SEQ ID NO: 3)
CACC ATG gcc ctg tcc aac aag ttc atc ggc gac gac atg aagatgacctaccacatggacggctgcgtgaacggccactacttca
ccgtgaagggcgagggcagcggcaagccctacgagggcacccagacctcc
accacaaggtgacgatggccaacggcggcccctggccactcatcgacat
cctgtccaccgtgacatgtacggcaaccgctgcttcaccgcctacccac
cagcatgcccgactacttcaagcaggccaccccgacggcatgtcctacga
gagaaccacacctacgaggacggcggcgtggccaccgccagctgggagat
cagcctgaagggcaactgcttcgagcacaagtccaccaccacggcgtgaa
cttcccgccgacggccccgtgatggccaagaagaccaccggctgggatc
cctcatcgagaagatgaccgtgtgcgacggcatcttgaagggcgacgtga
ccgccacctgatgctgcagggcggcggcaactacagatgccagaccacac
ctcctacaagaccaagaagcccgtgaccatgcccccaaccacgtggtgg
agcaccgcatcgccagaaccgacctggacaagggcggcaacagcgtgcag
ctgaccgagcacgccgtggcccacatcacctccgtggtgcccactga
(SEQ ID NO: 4)

-continued
MALSNKFIGDDMKMTYHMDGCVNGHYFTVKGEGSGKPYEGTQTSTFKVTM
ANGGPLAFSFDILSTVFMYGNRCFTAYPTSMPDYFKQAFPDGMSYERTFT
YEDGGVATASWEISLKGNCFEHKSTFHGVNFPADGPVMAKKTTGWDPSFE
KMTVCDGILKGDVTAFLMLQGGGNYRCQFHTSYKTKKPVTMPPNHVVEHR
IARTDLDKGGNSVQLTEHAVAHITSVVPF The nucleotides that are indicated in bold and underlined at the 5' end of SEQ ID NO:3 show the portion of the sequence that is varied among the variants. Further, at the 5' end, each variant nucleotide sequence also includes four nucleotides, CACC (in grey capitol letters), just up-stream of the ATG start codon. The variant nucleotide sequences were generated using standard recombinant DNA and molecular cloning techniques that are well known in the art (See, e.g., Sambrook et al., *Molecular Cloning: A Laboratory Manual*, Cold Spring Harbor laboratory, Cold Spring Harbor, N.Y. (1989); Silhavy et al., *Experiments with Gene Fusions*, Cold Spring Harbor Laboratory, Cold Spring Harbor, N.Y. (1984); and Ausubel et al., *Current Protocols in Molecular Biology*, Greene Publishing Assoc. and Wiley-Interscience (1987). The variant nucleotide sequences used in the yeast experiments are provided in Table 3 (SEQ ID NOs:27-48).

TABLE 3

AmCyan for expression in yeast

| Variant # | Nucleotide Sequence [−4 to +35] | MFE | EFE |
|---|---|---|---|
| 5433 | CACCATGGCGCTCTCCAATAAATTTATTGGAGACGACATG (SEQ ID NO: 27) | −16.30 | −16.49 |
| 1451 | CACCATGGCGCTCTCCAATAAGTTCATTGGAGACGACATG (SEQ ID NO: 28) | −15.20 | −15.33 |
| 4226 | CACCATGGCGTTGTCGAATAAATTTATCGGCGACGACATG (SEQ ID NO: 29) | −15.20 | −15.74 |
| 2753 | CACCATGGCTCTCTCCAATAAATTTATTGGAGACGACATG (SEQ ID NO: 30) | −13.60 | −14.17 |
| 5426 | CACCATGGCCTTGAGCAATAAGTTCATAGGTGATGATATG (SEQ ID NO: 31) | −13.50 | −13.55 |
| 1370 | CACCATGGCGTTGTCAAATAAGTTTATTGGCGACGATATG (SEQ ID NO: 32) | −11.60 | −12.41 |
| 7158 | CACCATGGCCCTGAGCAATAAGTTCATCGGTGATGATATG (SEQ ID NO: 33) | −11.60 | −11.68 |
| 4960 | CACCATGGCCTTGTCTAACAAGTTCATTGGAGACGATATG (SEQ ID NO: 34) | −9.30 | −10.49 |
| 7663 | CACCATGGCACTGTCCAATAAGTTCATCGGTGATGATATG (SEQ ID NO: 35) | −9.30 | −9.34 |
| 3065 | CACCATGGCTTTGTCGAACAAGTTCATCGGGGACGATATG (SEQ ID NO: 36) | −7.60 | −9.47 |
| 5108 | CACCATGGCACTCAGTAATAAATTTATTGGCGATGATATG (SEQ ID NO: 37) | −7.60 | −7.72 |
| 2493 | CACCATGGCGTTGTCTAACAAGTTCATCGGAGACGATATG (SEQ ID NO: 38) | −6.60 | −8.27 |
| 3961 | CACCATGGCGTTGTCCAACAAATTTATAGGAGATGACATG (SEQ ID NO: 39) | −6.60 | −6.71 |
| 3531 | CACCATGGCTTTATCGAATAAATTCATTGGGGACGATATG (SEQ ID NO: 40) | −4.50 | −6.28 |
| 613 | CACCATGGCACTATCCAACAAATTTATAGGAGACGACATG (SEQ ID NO: 41) | −4.50 | −4.59 |
| 5223 | CACCATGGCATTGAGTAACAAATTTATAGGCGACGATATG (SEQ ID NO: 42) | −3.10 | −3.39 |
| 5246 | CACCATGGCCCTGTCAAATAAATTTATAGGCGACGATATG (SEQ ID NO: 43) | −3.10 | −4.87 |
| 1214 | CACCATGGCATTAAGTAATAAATTCATAGGAGACGATATG (SEQ ID NO: 44) | −2.30 | −2.90 |
| 5013 | CACCATGGCATTGAGTAACAAGTTTATCGGGGATGATATG (SEQ ID NO: 45) | −2.30 | −4.00 |
| 7122 | CACCATGGCATTAAGCAACAAATTTATAGGAGACGATATG (SEQ ID NO: 46) | −1.00 | −1.71 |

TABLE 3-continued

AmCyan for expression in yeast

| Variant # | Nucleotide Sequence [-4 to +35] | MFE | EFE |
|---|---|---|---|
| 8537 | CACCATGGCGCTGTCAAACAAATTTATAGGGGATGATATG (SEQ ID NO: 47) | -1.00 | -2.69 |
| 8979 | CACCATGGCGCTTTCAAACAAATTTATAGGGGATGATATG (SEQ ID NO: 48) | -0.42 | -2.44 |

Example 4. Plant Transformation and Expression

Expression vectors capable of directing the expression of the variants were designed as described above. SEQ ID NO:1 and Table 2 provide the sequences of the variants.

The constitutive CaMV 35S promoter was used to drive expression of the dicot optimized variant genes. The tobacco expressed reporter protein, AmCyan, was targeted to the chloroplast via fusion to the *Chlamydomonas reinhardtii* small sub-unit Rubisco transit peptide sequence.

Tobacco expression vectors used the binary vector, pGR106, containing potato virus X (PVX) amplicon (Lu et al., 2003, EMBO J, 22:5690-5699). It is noted that similar vectors can be constructed for transformation and expression in other expression systems.

All expression cassettes are sub-cloned into a binary vector for transformation into tobacco using recombinant DNA techniques that are known in the art. The expression vector can also contain a protoporphyrinogen oxidase (PPO) selection marker driven by the same promoter, hence PPO can serve as an internal control.

Transient expression in tobacco leaves. Expression cassettes were cloned into either a binary vector or a binary vector also containing an origin of replication from beet curly top virus (BCTV). The binary vectors without the origin of replication from BCTV were transferred into *Agrobacterium tumefaciens* strain LBA4404 using the freeze-thaw method (An et al., "Binary vector". In: Gelvin S B, Schilproot R A (eds), *Plant molecular biology manual*. Kluwar Academic Publishers, Dordrecht, pp A3 1-19 (1988)). The binary vectors containing the origin of replication from BCTV (BCTV binary vectors) were transferred into *Agrobacterium tumefaciens* strain LBA4404 containing a helper plasmid that contains a replicase sequence from BCTV also using the freeze-thaw method as described herein.

Tobacco leaves were used for the transient expression of target proteins in plant tissue. Tobacco leaves from transgenic TEV-B tobacco plants (made in the tobacco cultivar Xanthi) containing a mutated P1/HC-Pro gene from TEV that suppresses post-transcriptional gene silencing (Mallory et al., *Nat Biotechnol* 20:622 (2002)) were used for transient expression of selected enzymes. Preparation of *Agrobacterium* cultures and infiltration of tobacco was carried out as described by Azhakanandam et al. (*Plant Mol. Biol.* 63: 393-404 (2007)). In brief, the genetically modified agrobacteria were grown overnight in 50 mL of LB medium containing 100 μM acetosyringone and 10 μM MES (pH 5.6). The agrobacteria were then pelleted by centrifugation at 4000×g for 10 min and the pellets resuspended in infection medium (Murashige and Skoog salts with vitamins, 2% sucrose, 500 μM MES (pH 5.6), 10 μM MgSO4, and 100 μM acetosyringone) to a concentration of OD600=1.0 and subsequently held at 28° C. for 3 hours. Infiltration of individual leaves was carried out on TEV-B tobacco plants (about 4 weeks old) using a 5 mL syringe by pressing the tip of the syringe (without a needle) against the abaxial surface of the leaf. Infiltrated plants were maintained at 22-25° C. with a photoperiod of 16 hours light and 8 hours dark. Plant tissue was harvested after about 5 days post infiltration for subsequent analysis.

Example 5. Yeast Transformation and Expression

The plasmids prepared as described in Example 3 were introduced into yeast (*Saccharomyces cerevisiae*) using the FAST™-Yeast Transformation kit (G-Biosciences, St Louis, Mo., USA). Since the vector contains the kanMX4 cassette, G-418 disulfate salt (Sigma, A1720) was used as the selection agent at a final concentration of 200 μg/ml.

Preparation of Competent Cells. Yeast cells were grown at 30° C. in 10 ml YPD broth until mid-log phase (about 5×106 to about 2×107 cells/ml or an OD600 of about 0.8 to about 1.0). Cells were pelleted at 500×g for 4 minutes and the supernatant discarded. 10 ml Wash Solution was used to wash the pellet. Following the wash, the cells were re-pelleted and the supernatant discarded. One ml Competent Solution was added to the pellet to re-suspend the cells.

Transformation. Competent cells (50 μl) were mixed with 0.2-1 μg DNA in a volume of less than 5 μl. Transformation Solution (500 μl) was added to the cells and mixed thoroughly. The cell/DNA mixture was incubated at 30° C. for 45 minutes and then mixed vigorously by flicking with a finger. The mixing step was performed 2-3 times during the 45 minute incubation.

The transformation mixture (DNA/cells) was spread (50 μl-150 μl) on an appropriate plate as known in the art. The plate with the transformation mixture was then incubated at 30° C. for 2-4 days to allow for growth of transformants.

Transgenic yeast cells were identified based on their ability to produce blue fluorescence when viewed under a fluorescence microscope.

Example 6. Sample Collection from Tobacco Leaves Transiently Expressing Reporter Protein AmCyan Three tobacco plants were planted per construct for sampling for qRT-PCR and ELISA. Two leaves per plant were infiltrated with agrobacteria containing the nucleotide sequences of the variants that express the AmCyan protein. Six samples were collected from the infiltrated leaves three days after infiltration, two samples from each plant. Two "punches" (about 20 mg) of leaf tissue were collected per sample.

Protein extracts were prepared from the approximately 100-500 mg of leaf tissue collected from tobacco plants transiently expressing AmCyan, as described above. Specifically, leaf material was placed into 24 deep well blocks containing small steel balls and pre-cooled on dry ice. Samples were ground to a fine powder using a Genogrinder (SPEC/CertiPrep, Metuchen, N.J.). Samples were then extracted in 500-1000 μl of Western Extraction Buffer (WEB=12.5 mM sodium borate, pH10; 2% BME and 1%

SDS) at room temperature for approximately 30 minutes followed by centrifugation for 5 minutes at 13,000 rpm.

Example 7. Sample Collection from the Yeast Expression System

Three colonies were picked per each variant. Transgenic yeast cells were grown overnight in YPD broth containing G-418 at 30° C. with shaking at 255 rpm. The following morning, cultures were diluted to an O.D. of about 0.5 at 600 nm. Three to four hours later when the O.D. of the cultures reached about 1.0 at 600 nm, the cells were harvested. Two ml for each variant was used and total protein and total RNA were isolated.

Protein was isolated using Y-PER Yeast Protein Extraction Reagent (Thermo Scientific, Rockford, Ill.). Total RNA was isolated using RNA Easy Mini Kit (QIAGEN). To generate spheroplasts, yeast cells were resuspended in 2 ml of Buffer Y containing zymolase and incubated 30 min at 30° C. with gentle shaking at 75 rpm. Buffer Y was prepared by adding 50× (10 mg/ml) zymolase-100T (from *Arthrobacter luteus*; Seikagaku Biobusiness Corporation, Japan) and 0.1% β-mercaptoehtanol to 1M sorbitol and 0.1 EDTA, pH 7.4 solution. To eliminate DNA contamination, RNA samples were digested with RNAse-Free DNase Set (QIAGEN) according to the manufacturer's protocol.

Three protein and three RNA samples were analyzed by ELISA and quantitative PCR for each variant.

Example 8. Estimation of Transcript and Protein Levels

A. Estimation of transcript level by qRT-PCR method. Plant tissue samples or yeast cells expressing the variants were collected and kept frozen at −80° C. until processed. RNA was extracted from the samples by a Magnetic Bead (Promega) procedure followed by DNA digestion. TaqMan assays were selected based on the target of interest. Thus, these assays consist of a forward and reverse primer and a FAM-labeled probe that are specific to the target sequence. A species specific TET-labeled reference target was also run for each sample for relative expression calculation. One-step RT-PCR reactions were set up in triplicate (3 for endogenous reference gene (e.g., wild-type/native) and 3 for the target gene) in 384 well PCR plates. A wild type control and no-RT negative control were included on each plate to test for non-specific amplification and DNA contamination, respectively.

The results were captured on a real-time thermocycler (ABI 7900 HT). The threshold values were set by the analyzer for each reporter and the resulting data was exported to the sampling template. Relative expression was calculated for each sample.

B. Quantitative CFP ELISA. The CFP ELISA immunoassay is a quantitative sandwich assay for the detection of AmCyan fluorescent protein (CFP). It employs two polyclonal antibodies which have been produced against the CFP gene product and immunoadffinity purified against the CFP protein. High-binding polystyrene plates (Costar®, Cambridge Mass.) are coated at 4° C. overnight with 2 µg/ml rabbit anti-CFP (Protein A purified) in 25 mM borate, 75 mM NaCl, pH 8.5. Plates are washed five times with 10 mM Tris, pH 8.0 containing 0.05% Tween-20 and 0.2% NaN$_3$. Samples were prepared by adding four ¼ inch leaf punch samples into 96-well blocks containing steel beads. The samples are ground using a Kleco grinder followed by adding 500 µl 0.1M sodium tetraborate pH 7.5, 0.5% Tween-20, and 0.2% polyvinyl pyrrolidone (extraction buffer) and mixing well. The blocks are centrifuged at 3500×g for 2 min before diluting the supernatant in ELISA diluents (PBS containing 1% BSA, 0.05% Tween-20 and 0.2% NaN$_3$). Standards (128, 64, 32, 16, 8, 4, 2, and 0 ng/ml of purified CFP protein) are prepared in Elisa diluents. One hundred microliters of each appropriately diluted sample or standard is added to the plant, incubated for 1 hour at ambient temperature with shaking at 200 rpm, and washed five times. Goat anti-CFP IgG (100 µl/well) at 5 µg/ml is then added to the plate, incubated for 1 hour at ambient temperature with shaking at 200 rpm, and washed as before. Donkey anti-goat conjugated to alkaline phosphatase (Jackson ImmunoResearch, West Grove, Pa.) at 1 µg/ml is added to the plate (100 µl/well), incubated at ambient temperature with shaking at 200 rpm, and washed. Substrate p-nitropheyl phosphate (Sigma, St. Louis, Mo.) is added and allowed to develop for 30 min at ambient temperature. The absorbance is measured at 405 nm with 492 as a reference using a microplate reader (Tecan Rainbow, Research Triangle Park, N.C.). The standard curve uses a fouparameter curve fit to plot concentration versus the absorbance. It is noted that other methods of quantification of AmCyan involving fluorescent assays (AmCyan can be detected by excitation at 475 nm and emission at 515 nm) may be used to estimate the level of protein expression.

C. Western Blot analysis was performed to check for possible post translational modification of the expressed protein and a data analysis is done to correlate the thermodynamic parameters of mRNA and the level of protein production. Samples were ground to a fine powder and were then extracted in 500-1000 µl of Western Extraction Medium (WEB=12.5 mM sodium borate, pH 10; 2% BME and 1% SDS) at room temperature for approximately 30 minutes followed by centrifugation for 5 minutes at 13,000 rpm.

D. SDS-polyacrylamide gel electrophoresis (SDS-PAGE) was performed by transferring 10 µl of the extracted samples to an eppendorf tube and adding 25 µl 4XBioRad LDS or modified BioRad loading buffer (4× BioRad LDS: BME at a ratio of 2:1). Samples were heated for 10 minutes at 70° C. and then immediately placed on ice for 5 minutes. Following incubation on ice, samples were centrifuged briefly. Sample extracts (5-10 µl) were run on BioRad 4-12% Bis/Tris protein gel (18 well) using MOPS buffer.

E. Immunoblot analysis was performed by transferring SDS-PAGE gels onto a nitrocellulose membrane using chilled Nupage transfer buffer (Invitrogen) for 30 minutes at 100 volts. The total protein transferred to the blot was visualized using Ponceau stain (Sigma). Following Ponceau staining, the membrane was incubated in blocking buffer for 30 minutes in TBST wash buffer (30 mM Tris-HCL, pH 7.5, 100 mM NaCl, and 0.05% Tween 20) with 3% dry milk, then washed three times for 5 minutes in TBST. The primary antibody was added at 1 µg/ml in TBST wash buffer with 3% milk, and the blot incubated 2 hours to overnight. Following incubation, the blot was washed three times for 5 minutes each in TBST wash buffer. The secondary antibody (Rabbit-AP) was diluted 1:8000 (in TBST) and added to blot for at least 30 minutes. Following incubation in the secondary antibody, the blot was again washed three times for 5 minutes each. Visualization of immuno reactive bands was carried out by adding Moss BCIP/NBT-alkaline phosphatase substrate. The blots were rinsed thoroughly in water following incubation in the BCIP/NBT substrate and allowed to air dry.

F. Fluorescent Microscopy. The tobacco leaf samples were examined under the microscope (Nikon SMZ 1500) for accumulation of fluorescent AnCyan protein.

Example 9. Results

A. Tobacco In-Planta Transient Expression System.

Figure 3A:
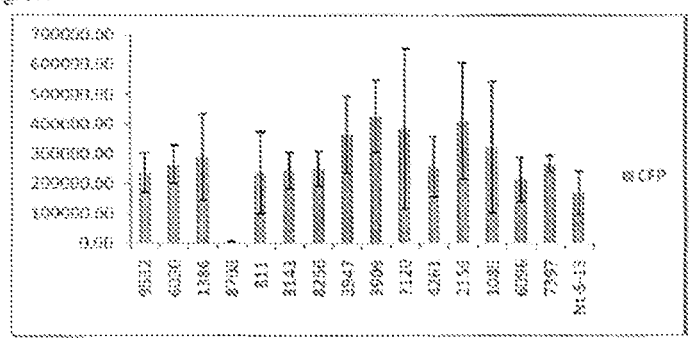
FIG. 3A-B shows the level of AmCyan transcripts (A) and relative mRNA levels of AmCyan to PPO (B) in leaf samples infiltrated with the vector constructs encoding different variants [Table 2] of N-terminal ssRubisco Chloroplast transit peptide with AmCyan (CFP) in tobacco transient system.
Figure 3B:
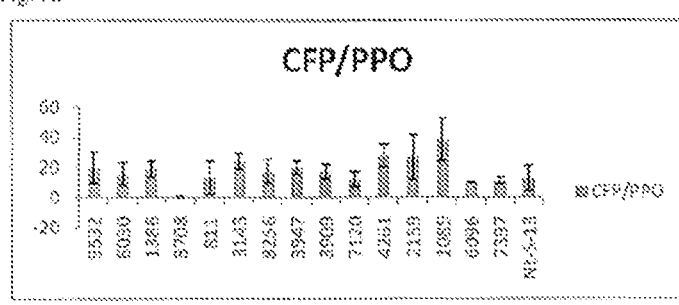

Expression level of transiently expressed AmCyan protein in plants. Two sets of independent experiments were carried out to analyze the expression level of transiently expressed AmCyan protein in tobacco infiltrated with different vector constructs of the variant nucleotide sequences. See FIG. 3, which shows the level of AmCyan transcripts in leaf samples infiltrated with indicator vector constructs (FIG. 3A) and relative mRNA levels of AmCyan to PPO (FIG. 3B).

The qRT-PCR results suggest that all constructs have similar mRNA levels within the variations typical of qRT-PCR for the data with the exception of construct 8707, which had a very low mRNA level.

Figure 4A:
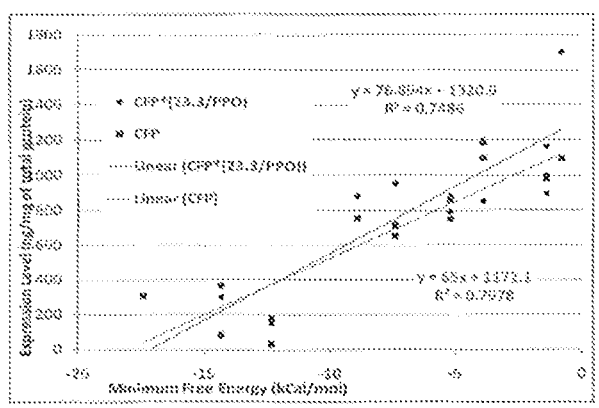
FIG. 4A-B shows the correlation between the levels of protein production (ELISA) of CFP (AmCyan) variants and their minimum free energy levels (A) and their ensemble free energy levels (B).
Figure 4B:
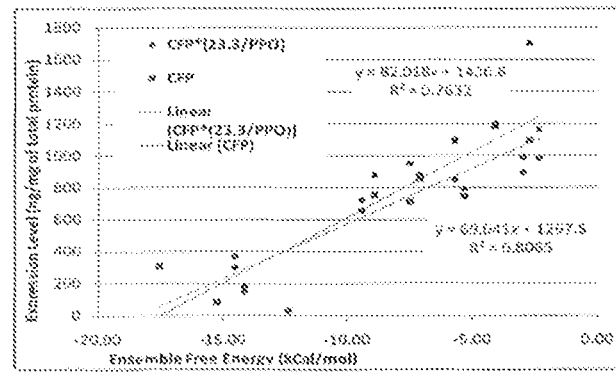
Figure 5A:
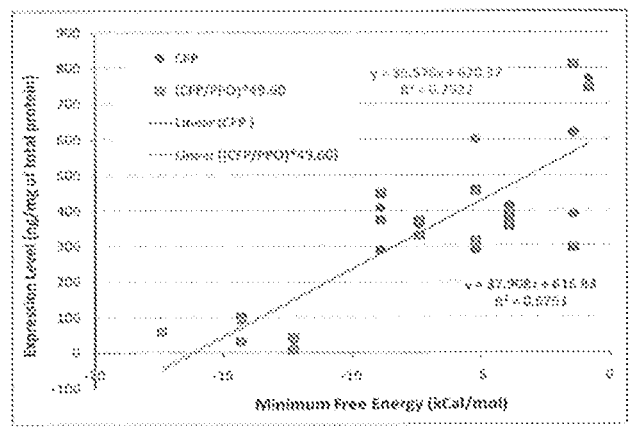
FIG. 5A-B shows the correlation between the levels of protein production (ELISA) of AmCyan (CFP) variants and their minimum free energy levels (A) and their ensemble free energy levels (B). CFP=AmCyan [Cyan Fluorescent Protein] expression level; CFP*(23.3/PPO)=CFP expression level normalized with respect to expression level of PPO (from the same tobacco transient vector).
Figure 5B:
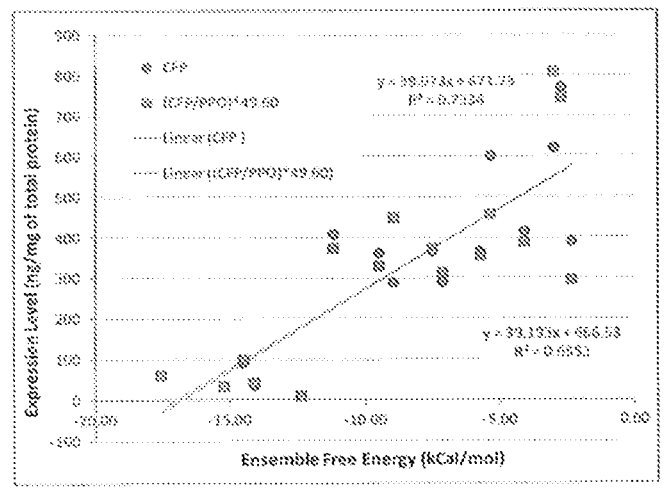

The expression levels of transiently expressed AmCyan protein in tobacco for various constructs were quantified by the ELISA method. Duplicate samples from three tobacco plants were collected for each construct. The expression levels (measured by ELISA) of CPF were normalized with respect to total extracted cellular protein. Averages of six data points are plotted in FIG. 4A and FIG. 4B. The expression levels of the internalized PPO control from the same samples were also quantified by the ELISA method and normalized with respect to total extracted cellular protein. The ELISA data shows that the expression level for PPO is almost the same for the different constructs while the expression level for AmCyan (CFP) varied over a wide range. The expression levels of AmCyan (square-CFP) and the normalized relative values to PPO (circle-CFP*) were plotted against the free energy values (minimum free energy (FIG. 4A) and ensemble free energy (FIG. 4B) and of their 40 nucleotide (−4 to 36) mRNA transcripts. Similar plots for the second data set are shown in FIG. 5A and FIG. 5B.

These results clearly show that AmCyan protein expression levels increase with the increase in the free energy value of the 5' mRNA transcript with an $R^2$ value of 0.8 when the data were fitted with a linear equation. Similar results were observed for the expression level of AmCyan relative to PPO with a $R^2$ value of 0.75.

Figure 6:
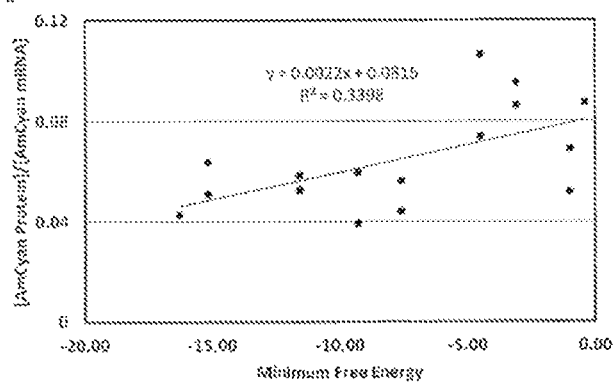
FIG. 6 shows the correlation of calculated mRNA folding energy and protein production (ELISA) in the yeast system, normalized with respect to measured transcript level (qRT-PCR).

An alternative plot of the data described above is shown in FIG. 6. A careful examination of the codon usage in the first 36 nucleotides of the gene indicate that the three contructs with the lowest expression levels have double rare codons of the same type. This suggests that the low expression of these constructs may be partially due to these double rare codons. The remaining data excluding these three constructs fit well with exponential decay ($R^2=0.81$) as shown in FIG. 6.

Fluorescent microscopic observations of tobacco leaf samples infiltrated with variant nucleotide sequence constructs. Visual observations under a fluorescent microscope of samples taken from leaves infiltrated with the different nucleic acid constructs described herein supported the co-relationship between the amount of AmCyan (CFP) variant protein expression and the folding free energy of the associated transcript.

B. Yeast Expression System.

RNA and Protein Analysis in Yeast Cells. The levels of AmCyan mRNA showed variations among different variants, however when they were normalized with respect to measure kanMX4 transcript, an internal control derived from the same vector, the ratios were not significantly different among different variants.

The levels of AmCyan protein measured by ELISA using anti-CFP antibody ranged from 3021 ng/mg to 12,062 ng/mg total soluble protein (Table 4).

TABLE 4

Protein expression levels of individual AmCyan variants measured by ELISA using anti-CFP antibody and their corresponding mRNA levels.

| | | AmCyan Protein | | AmCyan mRNA | | Ratio, |
|---|---|---|---|---|---|---|
| Variant | MFE* | ELISA Av*, ng/mg | ELISA SE** | AmCyan Av | AmCyan SE | Protein/mRNA |
| 5433 | −16.3 | 3021.2 | 836.1 | 70917.6 | 8452.6 | 0.043 |
| 1451 | −15.2 | 4886.6 | 37.0 | 95830.3 | 18253.2 | 0.051 |
| 4226 | −15.2 | 7891.0 | 2936.4 | 123750.5 | 40318.9 | 0.064 |
| 1370 | −11.6 | 9178.1 | 1793.3 | 156901.4 | 22251.8 | 0.058 |
| 7158 | −11.6 | 11622.8 | 2948.0 | 220724.3 | 64475.2 | 0.053 |
| 4960 | −9.3 | 6324.4 | 1775.3 | 161070.6 | 50908.3 | 0.039 |
| 7663 | −9.3 | 6642.6 | 1241.8 | 111453.4 | 16260.3 | 0.060 |
| 3065 | −7.6 | 3779.0 | 1330.2 | 85305.3 | 19265.8 | 0.044 |
| 5108 | −7.6 | 7661.0 | 314.6 | 135452.6 | 15848.1 | 0.057 |
| 3531 | −4.5 | 11603.3 | 2632.7 | 156894.3 | 27269.7 | 0.074 |
| 613 | −4.5 | 12062.0 | 1910.7 | 113197.8 | 19211.5 | 0.107 |
| 5223 | −3.1 | 7846.3 | 1547.9 | 82203.5 | 20914.5 | 0.095 |
| 5246 | −3.1 | 9888.2 | 842.8 | 114470.8 | 28544.8 | 0.086 |
| 7122 | −1 | 8969.3 | 1004.8 | 129938.8 | 23872.6 | 0.069 |
| 8537 | −1 | 6515.7 | 817.3 | 125433.9 | 34025.9 | 0.052 |
| 8979 | −0.42 | 9548.0 | 3310.1 | 109045.2 | 34480.9 | 0.088 |

*Av., Average of measurements (n = 3),
**SE, Standard error (n = 3).

The plot of the transcript folding energy versus the ratio of AmCyan protein expression (as measured by ELISA) over AmCyan mRNA (measured by qRT-PCR) is shown in FIG. 6 (data in Table 4). The correlation between estimated mRNA folding energy and AmCyan protein expression was $R^2=0.34$. Thus, this data shows that as MFE values increase, protein production increases while mRNA transcript levels remain constant.

Figure 7:
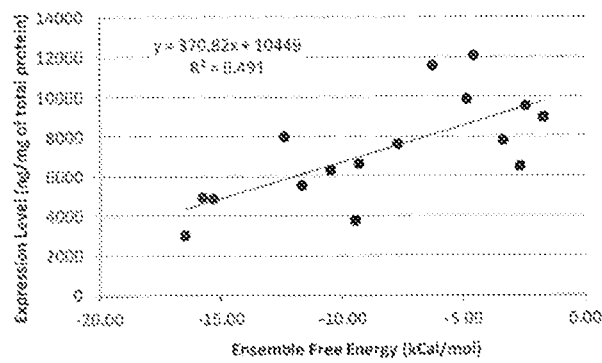
FIG. 7 shows the correlation between protein production levels (ELISA) of AmCyan (CFP) variants in the yeast system and their ensemble free energy levels.

A second plot (FIG. 7) in which the average ELISA data for each AmCyan variant was plotted against folding free energy, shows a linear correlation with $R^2=0.49$. In comparison to the corresponding experiments in tobacco, the correlation between protein expression and folding free energy values was lower in the yeast (0.49 versus 0.8). Some possible reasons for the lower correlation in the yeast expression system may include the overall difference in the expression system (in this case, the yeast system is selected for high levels of protein production), the use of rare codons and/or the occurrence of consecutive rare codons in a few of the AmCyan variants tested. However, it is noted that the $R^2$ value observed for yeast is comparable or slightly better than that observed for the *Escherichia coli* prokaryotic expression system of 0.44 reported by Kudla et al. (*Science* 324 (5924): 255-258 (2009)).

C. Maize In-Planta Transient Expression System.

Expression cassettes were cloned into a binary vector. The constructs were transferred into *Agrobacterium tumefaciens* strain LBA4404 containing helper plasmid (pSBI) using a freeze-thaw method (An et al., *Binary vector*. In: Gelvin S B, Schilproot R A (eds), *Plant molecular biology manual*. Kluwar Academic Publishers, Dordrecht, pp A3 1-19 (1988)). Preparation of *Agrobacterium* cultures was carried out as described by Azhakanandam et al., *Plant Mol. Biol.* 63: 393-404 (2007). In brief, the genetically modified agrobacteria were grown overnight in 50 mL of YP medium containing 100 μM acetosyringone and 10 μM MES (pH 5.6), and subsequently were pelleted by centrifugation at 4000×g for 10 min. The pellets were resuspended in the infection medium (Murashige and Skoog salts with vitamins, 2% sucrose, 500 μM MES (pH 5.6), 10 μM MgSO4, and 100 μM acetosyringone) to OD600=0.5 and subsequently held at 28 degrees C. for 2-3 hours.

The in planta transient expression system was established using maize seedlings. Seeds were germinated under greenhouse conditions in 2.5 inch pots filled with Fafard germination mix. Seedlings were kept under a 14/10 day/night cycle with a day light intensity of 2000 μ-mol-m-2·s-1 maintained with supplemental lighting. The temperature was maintained between 23° C.-26° C. The agroinfiltration experiment performed mostly using primary and secondary leaves of V2 stage (Ritchie S. W., Hanway J. J. Benson G. O. (edts): *How a Corn Plant Develops*: Iowa State Univ Special Report No. 48, July 2005). To make infiltration easier, the seedlings were watered 1-2 hours prior to agroinfiltration, which keeps the leaf turgid and stomata open. Infiltration of individual leaves was carried out on maize seedlings using a 5 mL syringe body (BD 5 ml syringe with Luer-Lok™ Tip, BD™ Franklin Lakes, N.J. 07427, USA), by pressing the tip of the syringe against the abaxial surface of the leaf. The first and second visible leaves of V2 stage were infiltrated with: 1 ml of *agrobacterium* suspension/28 seconds/leaf. Infiltrated plants were transferred and maintained under growth chamber conditions set at 25° C. with a 16/8 day/night cycle with a light intensity of 1900 μ-mol-m-2·s-1. Plant tissue was harvested after 4 days post infiltration for subsequent analysis.

Example 10. Step-Wise Selection of mRNA Sequences

To show the efficacy of selecting a mRNA sequence by group (step-wise rather than linear selection), variant mRNA sequences of ssRubisco chloroplast transit peptide with AmCyan (RbAmCyan) are selected as described herein. The MFE RNA secondary structure (MFE) value versus level of protein production for each mRNA sequence is determined. The sequences presented in Table 5, below, are variants of AmCyan with the chloroplast signal peptide, as described herein, with codon usage being optimized for tobacco expression. With the exception of the first three sequences provided in Table 5, each sequence was optimized for a GC content of about 50%. In addition, rare codon usage was avoided (i.e., codon usage of less than 15%). Approximately 209,952 different sequences were generated by reverse or back translation and 36 were chosen for testing (approximately three variants were selected for every 1 kcal/mol range) (Table 5).

TABLE 5

Sequence variants of RbAmCyan.

| Name | Seq | | MFE |
|---|---|---|---|
| >MAAVIAKSSVSA 90142 | CACCAUGGCUGCUGUCAUUGCCAAGAGUAGUGUCAGCGCC | (SEQ ID NO: 49) | -16.6 |
| >MAAVIAKSSVSA 16649 | CACCAUGGCAGCUGUUAUCGCUAAGAGCUCCGUGAGUGCC | (SEQ ID NO: 50) | -15.9 |
| >MAAVIAKSSVSA 91454 | CACCAUGGCUGCUGUCAUCGCUAAGUCUAGCGUGUCAGCA | (SEQ ID NO: 51) | -14.6 |
| >MAAVIAKSSVSA 220603 | CACCAUGGCAGCUGUCAUUGCAAAGAGCAGUGUUUCAGCA | (SEQ ID NO: 52) | -13.7 |
| >MAAVIAKSSVSA 126667 | CACCAUGGCAGCAGUCAUAGCUAAAAGCAGUGUCUCUGCA | (SEQ ID NO: 53) | -12.6 |
| >MAAVIAKSSVSA 45663 | CACCAUGGCAGCUGUGAUUGCAAAGUCAUCAGUUAGCGCA | (SEQ ID NO: 54) | -11.4 |
| >MAAVIAKSSVSA 24204 | CACCAUGGCUGCUGUUAUAGCAAAAAGCUCUGUCAGUGCC | (SEQ ID NO: 55) | -10.6 |
| >MAAVIAKSSVSA 149781 | CACCAUGGCUGCUGUGAUCGCUAAAAUCUAGCGUAUCUGCA | (SEQ ID NO: 56) | -10.0 |
| >MAAVIAKSSVSA 176557 | CACCAUGGCUGCAGUAAUAGCCAAAAGUAGCGUCUCUGCA | (SEQ ID NO: 57) | -9.6 |
| >MAAVIAKSSVSA 252588 | CACCAUGGCAGCUGUAAUCGCUAAGUCUAGCGUAAGUGCA | (SEQ ID NO: 58) | -9.2 |
| >MAAVIAKSSVSA 198140 | CACCAUGGCAGCAGUAAUUGCUAAAAGCAGUGUCAGCGCA | (SEQ ID NO: 59) | -8.8 |
| >MAAVIAKSSVSA 67 | CACCAUGGCAGCAGUUAUUGCAAAAAGCUCUGUGAGCGCA | (SEQ ID NO: 60) | -8.4 |
| >MAAVIAKSSVSA 134260 | CACCAUGGCUGCAGUAAUUGCUAAGAGCAGCGUAUCAGCA | (SEQ ID NO: 61) | -8.1 |

TABLE 5-continued

Sequence variants of RbAmCyan.

| Name | Seq | | MFE |
|---|---|---|---|
| >MAAVIAKSSVSA 69638 | CACCAUGGCCGCAGUGAUUGCAAAAUCAAGUGUAUCCGCU | (SEQ ID NO: 62) | -7.7 |
| >MAAVIAKSSVSA 12130 | CACCAUGGCAGCCGUUAUAGCAAAGAGCUCUGUAUCUGCU | (SEQ ID NO: 63) | -7.4 |
| >MAAVIAKSSVSA 205840 | CACCAUGGCUGCAGUCAUAGCCAAAAGUUCAGUUAGCGCU | (SEQ ID NO: 64) | -7.2 |
| >MAAVIAKSSVSA 898 | CACCAUGGCAGCCGUAAUUGCAAAAUCAAGCGUAAGCGCA | (SEQ ID NO: 65) | -6.8 |
| >MAAVIAKSSVSA 203464 | CACCAUGGCUGCUGUCAUUGCCAAAUCCAGUGUAAGUGCU | (SEQ ID NO: 66) | -6.5 |
| >MAAVIAKSSVSA 3421 | CACCAUGGCAGCAGUAAUAGCUAAGAGUUCCGUUUCAGCC | (SEQ ID NO: 67) | -6.2 |
| >MAAVIAKSSVSA 146286 | CACCAUGGCAGCUGUAAUCGCUAAAUCUUCAGUGAGCGCU | (SEQ ID NO: 68) | -5.8 |
| >MAAVIAKSSVSA 231944 | CACCAUGGCUGCAGUCAUAGCAAAGUCUAGUGUUAGUGCC | (SEQ ID NO: 69) | -5.5 |
| >MAAVIAKSSVSA 260970 | CACCAUGGCUGCAGUUAUAGCAAAAAGCUCAGUGUCCGCU | (SEQ ID NO: 70) | -5.2 |
| >MAAVIAKSSVSA 18682 | CACCAUGGCUGCUGUUAUAGCUAAAUCAUCCGUAAGCGCC | (SEQ ID NO: 71) | -4.9 |
| >MAAVIAKSSVSA 4483 | CACCAUGGCAGCAGUAAUAGCUAAGAGUAGUGUCAGCGCA | (SEQ ID NO: 72) | -4.5 |
| >MAAVIAKSSVSA 179366 | CACCAUGGCCGCUGUUAUUGCCAAAUCAUCAGUCAGUGCA | (SEQ ID NO: 73 | -4.4 |
| >MAAVIAKSSVSA 245289 | CACCAUGGCUGCAGUCAUCGCAAAAUCUUCAGUUUCCGCA | (SEQ ID NO: 74) | -3.9 |
| >MAAVIAKSSVSA 234943 | CACCAUGGCAGCUGUGAUCGCUAAAAGUUCUGUAUCAGCC | (SEQ ID NO: 75) | -3.6 |
| >MAAVIAKSSVSA 196281 | CACCAUGGCUGCAGUCAUCGCUAAAUCUUCAGUAUCCGCU | (SEQ ID NO: 76) | -3.2 |
| >MAAVIAKSSVSA 291743 | CACCAUGGCCGCCGUAAUAGCAAAAAGUUCUGUAAGCGCU | (SEQ ID NO: 77) | -2.8 |
| >MAAVIAKSSVSA 202071 | CACCAUGGCCGCCGUCAUUGCAAAAAGUUCAGUAUCAGCA | (SEQ ID NO: 78) | -2.4 |
| >MAAVIAKSSVSA 10852 | CACCAUGGCUGCCGUAAUCGCUAAAUCAUCUGUCUCUGCU | (SEQ ID NO: 79) | -2.0 |
| >MAAVIAKSSVSA 80632 | CACCAUGGCCGCUGUUAUUGCAAAAUCCUCCGUAUCUGCU | (SEQ ID NO: 80) | -1.6 |
| >MAAVIAKSSVSA 271445 | CACCAUGGCCGCAGUAAUUGCUAAAUCUUCAGUCUCCGCU | (SEQ ID NO: 81) | -1.4 |
| >MAAVIAKSSVSA 14671 | CACCAUGGCCGCAGUUAUCGCAAAAUCAUCAGUCUCAGCA | (SEQ ID NO: 82) | -1.0 |
| >MAAVIAKSSVSA 289906 | CACCAUGGCCGCCGUAAUUGCAAAAUCAUCUGUUUCCGCU | (SEQ ID NO: 83) | -0.9 |
| >MAAVIAKSSVSA 80081 | CACCAUGGCCGCCGUUAUCGCAAAAUCAUCAGUAUCAGCU | (SEQ ID NO: 84) | -0.4 |

The mRNA sequences in Table 5 are tested in a tobacco transient expression system as before and the expression level of the transcript and protein levels can be estimated by qRT-PCR and ELISA, respectively, as described herein.

To test variants in a corn expression system, sequences were optimized for corn codon usage and sequences comprising rare codons, as defined herein, near the start codon were not used (Table 6). The corresponding tobacco optimized sequences are in Table 5, above.

TABLE 6

Sequence variants optimized for corn codon usage.

| Name | Seq | | MFE |
|---|---|---|---|
| >MAAVIAKSSVSA 91454 | CACCAUGGCUGCUGUCAUCGCUAAGUCUAGCGUGUCAGCA | (SEQ ID NO: 85) | -14.6 |
| >MAAVIAKSSVSA 45663 | CACCAUGGCAGCUGUGAUUGCAAAGUCAUCAGUUAGCGCA | (SEQ ID NO: 86) | -11.4 |
| >MAAVIAKSSVSA 67 | CACCAUGGCAGCAGUUAUUGCAAAAAGCUCUGUGAGCGCA | (SEQ ID NO: 87) | -8.4 |
| >MAAVIAKSSVSA 260970 | CACCAUGGCUGCAGUUAUAGCAAAAAGCUCAGUGUCCGCU | (SEQ ID NO: 88) | -5.2 |
| >MAAVIAKSSVSA 245289 | CACCAUGGCUGCAGUCAUCGCAAAAUCUUCAGUUUCCGCA | (SEQ ID NO: 89) | -3.9 |
| >MAAVIAKSSVSA 14671 | CACCAUGGCCGCAGUUAUCGCAAAAUCAUCAGUCUCAGCA | (SEQ ID NO: 90) | -1.0 |

The expression level of the transcript and the protein is estimated in corn by qRT-PCR & ELISA, respectively, as described herein.

Example 11. Rare Codon Usage

In some instances, avoiding use of rare codon can be a step in optimizing transcript sequence based on its folding free energy. Table 7 provides variants of AmCyan with chloroplast targeting signal peptide each having one or more rare codons near the start codon. Six pairs of variants are tested: one set with rare codons and one set without rare codons. A rare codon is one which has a tRNA with an abundance of less than 15%

The impact of consecutive rare codons near the start codon can be studied using the sequences set forth in Table 7 (see, e.g., AAV and VSA in Table 7 below). Such consecutive rare codons may more severely impact the protein production by a mRNA than one with a single rare codon near the start site.

TABLE 7

RbAmCyan variant sequences with tobacco rare codons

| Name | Seq | | MFE |
|---|---|---|---|
| >MAAVIAKSSVSA RareCodon 18 | CACCAUGGCCGCCGUAAUCGCCAAAAGCAGCGUAAGCGCC | (SEQ ID NO: 91) | −8.8 |
| >MAAVIAKSSVSA RareCodon 119 | CACCAUGGCCGCCGUAAUCGCCAAAUCCAGCGUAAGCGCC | (SEQ ID NO: 92) | −7.7 |
| >MAAVIAKSSVSA RareCodon 96 | CACCAUGGCCGCCGUCAUAGCCAAAAGCUCCGUAAGCGCC | (SEQ ID NO: 93) | −6.2 |
| >MAAVIAKSSVSA RareCodon 85 | CACCAUGGCCGCCGUAAUCGCCAAAAGCUCCGUAAGCGCC | (SEQ ID NO: 94) | −5.8 |
| >MAAVIAKSSVSA RareCodon 110 | CACCAUGGCCGCCGUCAUAGCCAAGAGCUCCGUCUCCGCC | (SEQ ID NO: 95) | −4.9 |
| >MAAVIAKSSVSA RareCodon 3 | CACCAUGGCCGCCGUAAUAGCCAAAAGCUCCGUCUCCGCC | (SEQ ID NO: 96) | −3.9 |

Rare codons usage
Ser, AGC, 0.13, UCC, 0.13
Ala, GCC, 0.17
Val, GUC, 0.17, GUA, 0.17

These variants are tested in tobacco transient system as described herein and the expression level of the transcript and the protein is estimated by qRT-PCR & ELISA, respectively, as described herein.

Example 12. Use of Non-Consequential Mutations to Modulate Protein Production Levels Variants of nucleotide sequence encoding 5-enolpyruvyl-3-phosphoshikimate (EPSP) synthase with chloroplast targeting signal peptide from maize were generated. Also included are wild type (WT) EPSPS sequence as control, also the EPSPS transcript with −6.4 value for MFE RNA secondary structure. The codon usage was optimized for tobacco expression (Table 8).

TABLE 8

Sequence variants with mutation for EPSPS and excluding rare codons in tobacco

| Name | Seq | | MFE |
|---|---|---|---|
| >MAALGTKGGAGT EPSPSMutant 4172 | AACCAUGGCAGCAUUAGGAACAAAAGGGGGAGCAGGAACC | (SEQ ID NO: 97) | −0.85 |

TABLE 8-continued

Sequence variants with mutation for EPSPS and excluding rare codons in tobacco

| Name | Seq | MFE |
|---|---|---|
| >MAAIGTKAGGGT EPSPSMutant 2931 | AACCAUGGCAGCAAUCGGAACAAAAGCAGGAGGAGGUACU (SEQ ID NO: 98) | -1.19 |
| >MAAIGTKAGAGS EPSPSMutant 3713 | AACCAUGGCAGCAAUAGGAACAAAGGCAGGAGCAGGCAGU (SEQ ID NO: 99) | -1.21 |
| >MAAIGSKAGAGT EPSPSMutant 1574 | AACCAUGGCAGCAAUUGGAUCAAAAGCAGGAGCAGGAACC (SEQ ID NO: 100) | -2.8 |
| >MAALGTRGAAGT EPSPSMutant 4993 | AACCAUGGCAGCAUUAGGUACAAGAGGAGCAGCAGGCACU (SEQ ID NO: 101) | -2.8 |
| >MAAIGSRAAAGT EPSPSMutant 5931 | AACCAUGGCAGCAAUAGGUAGUAGAGCAGCAGCAGGCACA (SEQ ID NO: 102) | -3.4 |
| >MAAMATKAAAGT CTP-Zm EPSPS 30418 | AACCAUGGCAGCUAUGGCAACUAAAGCAGCAGCAGGCACA (SEQ ID NO: 103) | -6.4 |
| >MAAMATKAAAGT CTP-Zm_EPSPS WT | AACCAUGGCUGCUAUGGCUACUAAGGCUGCUGCUGGAACU (SEQ ID NO: 104) | -10.6 |

The variants are tested in tobacco transient system as before and the expression level of the transcript and the protein can be estimated by qRT-PCR & ELISA, respectively, as described herein.

All publications, patent applications, patents and other references cited herein are incorporated by reference in their entireties for the teachings relevant to the sentence and/or paragraph in which the reference is presented.

The foregoing is illustrative of the present invention, and is not to be construed as limiting thereof. The invention is defined by the following claims, with equivalents of the claims to be included therein.

That which is claimed is:

1. A method for producing a polypeptide of interest in a cell of an organism, the method comprising:
   a) selecting an mRNA encoding a polypeptide of interest, comprising:
   i) producing an array of individual mRNA sequences comprising different nucleotide sequences encoding the polypeptide of interest, wherein the individual mRNA sequences comprise nucleotides from positions −20 through 50 relative to the start codon;

ii) determining ensemble free energy (EFE) RNA secondary structure for each individual mRNA sequence of (i);
iii) ranking the individual mRNA sequences of the array according to the EFE RNA secondary structure determined in (ii) from highest EFE RNA secondary structure to lowest EFE RNA secondary structure; and
iv) selecting a mRNA sequence from the ranked array of step (iii),wherein the selected mRNA produces the polypeptide of interest in a eukaryotic organism, and at least steps (i) to (iii);
b) mutating the nucleotide sequence of the mRNA of (a) to produce a mutated mRNA having a reduced EFE RNA secondary structure as compared to the EFE RNA secondary structure of the nucleotide sequence of the mRNA of (a); wherein the mutated mRNA encodes a mutated polypeptide sequence as compared to the polypeptide sequence encoded by the mRNA of (a), the mutated polypeptide sequence retains the function of the polypeptide encoded by the mRNA of (a);
c) introducing said mutated mRNA into a plant or a fungus, thereby expressing the mRNA and producing the polypeptide of interest in said plant or a fungus, and expression of the mutated mRNA sequence results in modified production of the polypeptide of interest as compared to the wild-type mRNA sequence.

2. The method of claim 1, wherein the individual mRNA sequences comprise nucleotides at positions −15 through 40 relative to the start codon.

3. The method of claim 1, wherein the individual mRNA sequences comprise nucleotides at positions −4 through 35 relative to the start codon.

4. The method of claim 1, wherein the mRNA is selected for enhanced production of a polypeptide of interest.

5. The method of claim 4, wherein the mRNA is selected from the group of mRNAs having an EFE in the range from about 0 kcal/mol to about −5 kcal/mol, wherein expression of the selected mRNA sequence results in enhanced production of the polypeptide of interest as compared to the wild-type mRNA sequence.

6. The method of claim 1, wherein the mRNA is selected for reduced production of a polypeptide of interest.

7. The method of claim 6, wherein the mRNA is selected from the group of mRNAs having an EFE in the range from about −9 kcal/mol to about −18 kcal/mol, wherein expression of the selected mRNA sequence results in reduced production of the polypeptide of interest as compared to the wild-type mRNA sequence.

8. The method of claim 1, wherein the polypeptide of interest comprises a leader peptide.

9. A method for producing a polypeptide of interest in a cell of an organism, the method comprising:
a) selecting an mRNA encoding a polypeptide of interest, comprising
i) producing an array of individual mRNA sequences comprising different nucleotide sequences encoding the polypeptide of interest, wherein the individual mRNA sequences comprise nucleotides from positions −20 through 50 relative to the start codon;
ii) determining ensemble free energy (EFE) RNA secondary structure for each individual mRNA sequence of (i);
iii) ranking the individual mRNA sequences of the array according to the EFE RNA secondary structure determined in (ii) from highest EFE RNA secondary structure to lowest EFE RNA secondary structure; and
iv) selecting a mRNA sequence from the ranked array of step (iii),wherein the selected mRNA produces the polypeptide of interest in a eukaryotic organism, and at least steps (i) to (iii);
b) identifying the differences between the nucleotide sequence of the mRNA selected according to (a) and a wild-type endogenous nucleotide sequence of said organism, wherein the wild-type endogenous nucleotide sequence encodes a polypeptide of interest that is the same as that encoded by the mRNA selected according to (a); and
c) mutating in situ the endogenous nucleotide sequence encoding the polypeptide of interest to incorporate each of the nucleotide differences identified in (b) into the endogenous nucleotide sequence to produce a mutated mRNA having a reduced EFE RNA secondary structure;
d) introducing said mutated mRNA into a plant or a fungus, thereby expressing the mRNA and producing the polypeptide of interest in said plant or a fungus, whereby the production of the polypeptide of interest from the in situ mutated endogenous nucleotide sequence in the cell of the organism is modified.

10. The method of claim 9, wherein the individual mRNA sequences comprise nucleotides at positions −15 through 40 relative to the start codon.

11. The method of claim 9, wherein the individual mRNA sequences comprise nucleotides at positions −4 through 35 relative to the start codon.

12. The method of claim 9, wherein the mRNA is selected for enhanced production of a polypeptide of interest.

13. The method of claim 12, wherein the mRNA is selected from the group of mRNAs having an EFE in the range from about 0 kcal/mol to about −5 kcal/mol, wherein expression of the selected mRNA sequence results in enhanced production of the polypeptide of interest as compared to the wild-type mRNA sequence.

* * * * *

SEQUENCE LISTING

```
<160> NUMBER OF SEQ ID NOS: 126

<210> SEQ ID NO 1
<211> LENGTH: 826
<212> TYPE: DNA
<213> ORGANISM: Artificial
<220> FEATURE:
<223> OTHER INFORMATION: AmCyan reporter/ssRubisco chloroplast transit
      peptide construct coding sequence

<400> SEQUENCE: 1
caccatggcc gcggtcatag ccaaatcaag cgtttccgca gccgtggcaa ggcctgctag      60
atctagcgtg aggccgatgg ctgccttgaa acccgcagtc aaagcggcac ctgtggcagc     120
tccagcacaa gcgaatcagg ccctgagcaa caagttcatc ggcgacgaca tgaagatgac     180
ctaccacatg gacggctgcg tgaacggcca ctacttcacc gtgaagggcg agggcagcgg     240
caagccatac gagggcaccc agaccagcac cttcaaggtg acgatggcca acggtggccc     300
actggccttc agcttcgaca tcctgagcac cgtgttcatg tacggcaacc gctgcttcac     360
cgcctacccg accagcatgc cggactactt caagcaggcc ttcccggacg gcatgagcta     420
cgagcgcacc ttcacctacg aggacggcgg cgtggctacc gccagctggg agatcagcct     480
gaagggcaac tgcttcgagc acaagagcac cttccacggc gtgaacttcc cagccgacgg     540
cccggtgatg gccaagatga ccaccggctg ggatccgagc ttcgagaaga tgactgtgtg     600
cgacggcatc ctgaagggcg acgtgaccgc cttcctgatg cttcaaggcg gtggcaacta     660
ccgctgccag ttccacacca gctacaagac caagaagccc gtgaccatgc cgccaaacca     720
tgccgtggag cacaggatcg cccgcaccga cctggacaag ggcggcaaca gcgtccagct     780
gaccgagcac gccgtggccc acatcaccag cgtggtgccg ttctga                     826
```

```
<210> SEQ ID NO 2
<211> LENGTH: 229
<212> TYPE: PRT
<213> ORGANISM: Artificial
<220> FEATURE:
<223> OTHER INFORMATION: AmCyan reporter/ssRubisco chloroplast transit
      peptide construct peptide sequence

<400> SEQUENCE: 2

Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Gly Asn Tyr Arg
                165                 170                 175

Cys Gln Phe His Thr Ser Tyr Lys Thr Lys Lys Pro Val Thr Met Pro
            180                 185                 190

Pro Asn His Val Val Glu His Arg Ile Ala Arg Thr Asp Leu Asp Lys
        195                 200                 205

Gly Gly Asn Ser Val Gln Leu Thr Glu His Ala Val Ala His Ile Thr
    210                 215                 220

Ser Val Val Pro Phe
225

<210> SEQ ID NO 3
<211> LENGTH: 694
<212> TYPE: DNA
<213> ORGANISM: Artificial
<220> FEATURE:
<223> OTHER INFORMATION: AmCyan reporter/yeast transformation construct
      coding sequence

<400> SEQUENCE: 3
caccatggcc ctgtccaaca agttcatcgg cgacgacatg aagatgacct accacatgga      60
cggctgcgtg aacggccact acttcaccgt gaagggcgag ggcagcggca agccctacga     120
gggcacccag acctccacct tcaaggtgac gatggccaac ggcggccccc tggccttctc     180
cttcgacatc ctgtccaccg tgttcatgta cggcaaccgc tgcttcaccg cctaccccac     240
cagcatgccc gactacttca agcaggcctt ccccgacggc atgtcctacg agagaacctt     300
cacctacgag gacggcggcg tggccaccgc cagctgggag atcagcctga agggcaactg     360
```

-continued

```
cttcgagcac aagtccacct tccacggcgt gaacttcccc gccgacggcc ccgtgatggc    420
caagaagacc accggctggg atccctcctt cgagaagatg accgtgtgcg acggcatctt    480
gaagggcgac gtgaccgcct tcctgatgct gcagggcggc ggcaactaca gatgccagtt    540
ccacacctcc tacaagacca agaagcccgt gaccatgccc cccaaccacg tggtggagca    600
ccgcatcgcc agaaccgacc tggacaaggg cggcaacagc gtgcagctga ccgagcacgc    660
cgtggcccac atcacctccg tggtgcccct ctga                               694
```

<210> SEQ ID NO 4
<211> LENGTH: 229
<212> TYPE: PRT
<213> ORGANISM: Artificial
<220> FEATURE:
<223> OTHER INFORMATION: AmCyan reporter/yeast transformation construct peptide sequence

<400> SEQUENCE: 4

```
Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Ser Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
    50                  55                  60

Thr Val Phe Met Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
            100                 105                 110

Ile Ser Leu Lys Gly Asn Cys Phe Glu His Lys Ser Thr Phe His Gly
        115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Gly Asn Tyr Arg
                165                 170                 175

Cys Gln Phe His Thr Ser Tyr Lys Thr Lys Lys Pro Val Thr Met Pro
            180                 185                 190

Pro Asn His Val Val Glu His Arg Ile Ala Arg Thr Asp Leu Asp Lys
        195                 200                 205

Gly Gly Asn Ser Val Gln Leu Thr Glu His Ala Val Ala His Ile Thr
    210                 215                 220

Ser Val Val Pro Phe
225
```

<210> SEQ ID NO 5
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 5

```
caccatggca gcggtgattg ccaaatcatc ggtgtcagct                    40
```

<210> SEQ ID NO 6
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 6

```
caccatggcc gcggtcattg cgaaaagcag tgtgtcggcc                    40
```

<210> SEQ ID NO 7
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 7

```
caccatggcg gcggttattg ccaagtcgtc cgtgagtgcg                    40
```

<210> SEQ ID NO 8
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 8

```
caccatggcg gcggtcattg ctaaaagcag cgtgagcgcc                    40
```

<210> SEQ ID NO 9
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 9

```
caccatggcc gctgtgatcg caaagtccag cgtgtcagcc                    40
```

<210> SEQ ID NO 10
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 10

```
caccatggcc gcggtcatag cgaaaagctc tgtttccgca                    40
```

<210> SEQ ID NO 11
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 11

```
caccatggca gccgtgatag ctaagtcgtc tgtctcggct                                40
```

<210> SEQ ID NO 12
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 12

```
caccatggca gcagtgatcg caaagtcgag cgttagtgca                                40
```

<210> SEQ ID NO 13
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 13

```
caccatggca gccgttatcg ctaagagtag cgtgtctgct                                40
```

<210> SEQ ID NO 14
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 14

```
caccatggca gcagtaatcg cgaaatcaag tgttagtgca                                40
```

<210> SEQ ID NO 15
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 15

```
caccatggca gctgttattg caaagtcgtc cgtgagtgcc                                40
```

<210> SEQ ID NO 16
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 16

```
caccatggca gctgtaatag caaaatcctc tgtctcagca                                40
```

<210> SEQ ID NO 17
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 17

```
caccatggct gccgtaatcg caaagtcgtc cgtgagtgcg                                40
```

```
<210> SEQ ID NO 18
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 18
caccatggca gccgtaatcg caaagagcag cgtaagtgct                            40

<210> SEQ ID NO 19
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 19
caccatggca gctgtaatcg caaaatcatc tgtctccgca                            40

<210> SEQ ID NO 20
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 20
caccatggcc gccgtgatag ccaagtcgtc agtatccgct                            40

<210> SEQ ID NO 21
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 21
caccatggcc gcagtaatag ccaaatcttc agtttccgcc                            40

<210> SEQ ID NO 22
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 22
caccatggca gccgtaatag caaaatcatc agtcagcgcc                            40

<210> SEQ ID NO 23
<211> LENGTH: 40
<212> TYPE: DNA
<213> ORGANISM: Artificial
<220> FEATURE:
<223> OTHER INFORMATION: AmCyan reporter/ssRubisco chloroplast transit
      peptide construct variant sequence

<400> SEQUENCE: 23
caccatggcc gccgttattg caaaatcgtc tgtgtctgca                            40
```

<210> SEQ ID NO 24
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 24
caccatggcc gccgtaattg ctaaatcatc tgtctctgcc         40

<210> SEQ ID NO 25
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 25
caccatggcc gccgtaatag caaagagttc cgtatccgca         40

<210> SEQ ID NO 26
<211> LENGTH: 40
<212> TYPE: DNA
<213> ORGANISM: Artificial
<220> FEATURE:
<223> OTHER INFORMATION: AmCyan reporter/ssRubisco chloroplast transit peptide construct variant sequence

<400> SEQUENCE: 26
caccatggct gccgttattg caaaatcttc tgtttccgct         40

<210> SEQ ID NO 27
<211> LENGTH: 40
<212> TYPE: DNA
<213> ORGANISM: Artificial
<220> FEATURE:
<223> OTHER INFORMATION: AmCyan reporter/yeast transformation construct variant sequence

<400> SEQUENCE: 27
caccatggcg ctctccaata aatttattgg agacgacatg         40

<210> SEQ ID NO 28
<211> LENGTH: 40
<212> TYPE: DNA
<213> ORGANISM: Artificial
<220> FEATURE:
<223> OTHER INFORMATION: AmCyan reporter/yeast transformation construct variant sequence

<400> SEQUENCE: 28
caccatggcg ctctccaata agttcattgg agacgacatg         40

<210> SEQ ID NO 29
<211> LENGTH: 40
<212> TYPE: DNA
<213> ORGANISM: Artificial
<220> FEATURE:
<223> OTHER INFORMATION: AmCyan reporter/yeast transformation construct variant sequence

<400> SEQUENCE: 29
caccatggcg ttgtcgaata aatttatcgg cgacgacatg         40

```
<210> SEQ ID NO 30
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 30
caccatggct ctctccaata aatttattgg agacgacatg                          40

<210> SEQ ID NO 31
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 31
caccatggcc ttgagcaata agttcatagg tgatgatatg                          40

<210> SEQ ID NO 32
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 32
caccatggcg ttgtcaaata agtttattgg cgacgatatg                          40

<210> SEQ ID NO 33
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 33
caccatggcc ctgagcaata agttcatcgg tgatgatatg                          40

<210> SEQ ID NO 34
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 34
caccatggcc ttgtctaaca agttcattgg agacgatatg                          40

<210> SEQ ID NO 35
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 35
caccatggca ctgtccaata agttcatcgg tgatgatatg                          40

<210> SEQ ID NO 36
```

-continued

```
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 36
caccatggct ttgtcgaaca agttcatcgg ggacgatatg                          40

<210> SEQ ID NO 37
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 37
caccatggca ctcagtaata aatttattgg cgatgatatg                          40

<210> SEQ ID NO 38
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 38
caccatggcg ttgtctaaca agttcatcgg agacgatatg                          40

<210> SEQ ID NO 39
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 39
caccatggcg ttgtccaaca aatttatagg agatgacatg                          40

<210> SEQ ID NO 40
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 40
caccatggct ttatcgaata aattcattgg ggacgatatg                          40

<210> SEQ ID NO 41
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 41
caccatggca ctatccaaca aatttatagg agacgacatg                          40

<210> SEQ ID NO 42
<211> LENGTH: 40
```

```
<212> TYPE: DNA
<213> ORGANISM: Artificial
<220> FEATURE:
<223> OTHER INFORMATION: AmCyan reporter/yeast transformation construct
      variant sequence

<400> SEQUENCE: 42
caccatggca ttgagtaaca aatttatagg cgacgatatg                              40

<210> SEQ ID NO 43
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 43
caccatggcc ctgtcaaata aatttatagg cgacgatatg                              40

<210> SEQ ID NO 44
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 44
caccatggca ttaagtaata aattcatagg agacgatatg                              40

<210> SEQ ID NO 45
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 45
caccatggca ttgagtaaca agtttatcgg ggatgatatg                              40

<210> SEQ ID NO 46
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 46
caccatggca ttaagcaaca aatttatagg agacgatatg                              40

<210> SEQ ID NO 47
<211> LENGTH: 40
<212> TYPE: DNA
<213> ORGANISM: Artificial
<220> FEATURE:
<223> OTHER INFORMATION: AmCyan reporter/yeast transformation construct
      variant sequence

<400> SEQUENCE: 47
caccatggcg ctgtcaaaca aatttatagg ggatgatatg                              40

<210> SEQ ID NO 48
<211> LENGTH: 40
<212> TYPE: DNA
```

```
<213> ORGANISM: Artificial
<220> FEATURE:
<223> OTHER INFORMATION: AmCyan reporter/yeast transformation construct
      variant sequence

<400> SEQUENCE: 48
caccatggcg ctttcaaaca aatttatagg ggatgatatg                              40

<210> SEQ ID NO 49
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 49
caccauggcu gcugucauug ccaagaguag ugucagcgcc                              40

<210> SEQ ID NO 50
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 50
caccauggca gcuguuaucg cuaagagcuc cgugagugcc                              40

<210> SEQ ID NO 51
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 51
caccauggcu gcugucaucg cuaagucuag cgugucagca                              40

<210> SEQ ID NO 52
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 52
caccauggca gcugucauug caaagagcag uguuucagca                              40

<210> SEQ ID NO 53
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 53
caccauggca gcagucauag cuaaaagcag ugucucugca                              40

<210> SEQ ID NO 54
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 54
```
caccauggca gcugugauug caaagucauc aguuagcgca      40

<210> SEQ ID NO 55
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 55
caccauggcu gcuguuauag caaaaagcuc ugucagugcc      40

<210> SEQ ID NO 56
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 56
caccauggcu gcugugaucg cuaaaucuag cguaucugca      40

<210> SEQ ID NO 57
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 57
caccauggcu gcaguaauag ccaaaaguag cgucucugca      40

<210> SEQ ID NO 58
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 58
caccauggca gcuguaaucg cuaagucuag cguaagugca      40

<210> SEQ ID NO 59
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 59
caccauggca gcaguaauug cuaaaagcag ugucagcgca      40

<210> SEQ ID NO 60
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 60
caccauggca gcaguuauug caaaaagcuc ugugagcgca      40

<210> SEQ ID NO 61
<211> LENGTH: 40
<212> TYPE: RNA
<213> ORGANISM: Artificial

```
<220> FEATURE:
<223> OTHER INFORMATION: RbAmCyan variant mRNA sequence

<400> SEQUENCE: 61
caccauggcu gcaguaauug cuaagagcag cguaucagca                              40

<210> SEQ ID NO 62
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 62
caccauggcc gcagugauug caaaaucaag uguauccgcu                              40

<210> SEQ ID NO 63
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 63
caccauggca gccguuauag caaagagcuc uguaucugcu                              40

<210> SEQ ID NO 64
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 64
caccauggcu gcagucauag ccaaaaguuc aguuagcgcu                              40

<210> SEQ ID NO 65
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 65
caccauggca gccguaauug caaaaucaag cguaagcgca                              40

<210> SEQ ID NO 66
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 66
caccauggcu gcugucauug ccaaauccag uguaagugcu                              40

<210> SEQ ID NO 67
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 67
caccauggca gcaguaauag cuaagaguuc cguuucagcc                              40
```

<210> SEQ ID NO 68
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 68
caccauggca gcuguaaucg cuaaaucuuc agugagcgcu         40

<210> SEQ ID NO 69
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 69
caccauggcu gcagucauag caaagucuag uguuagugcc         40

<210> SEQ ID NO 70
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 70
caccauggcu gcaguuauag caaaaagcuc aguguccgcu         40

<210> SEQ ID NO 71
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 71
caccauggcu gcuguuauag cuaaaucauc cguaagcgcc         40

<210> SEQ ID NO 72
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 72
caccauggca gcaguaauag cuaagaguag ugucagcgca         40

<210> SEQ ID NO 73
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 73
caccauggcc gcuguuauug ccaaaucauc agucagugca         40

<210> SEQ ID NO 74
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 74
caccauggcu gcagucaucg caaaaucuuc aguuuccgca       40

<210> SEQ ID NO 75
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 75
caccauggca gcugugaucg cuaaaaguuc uguaucagcc       40

<210> SEQ ID NO 76
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 76
caccauggcu gcagucaucg cuaaaucuuc aguauccgcu       40

<210> SEQ ID NO 77
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 77
caccauggcc gccguaauag caaaaaguuc uguaagcgcu       40

<210> SEQ ID NO 78
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 78
caccauggcc gccgucauug caaaaaguuc aguaucagca       40

<210> SEQ ID NO 79
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 79
caccauggcu gccguaaucg cuaaaucauc ugucucugcu       40

<210> SEQ ID NO 80
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 80
caccauggcc gcuguuauug caaaauccuc cguaucugcu       40

<210> SEQ ID NO 81

```
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 81
caccauggcc gcaguaauug cuaaaucuuc agucuccgcu                       40

<210> SEQ ID NO 82
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 82
caccauggcc gcaguuaucg caaaaucauc agucucagca                       40

<210> SEQ ID NO 83
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 83
caccauggcc gccguaauug caaaaucauc uguuuccgcu                       40

<210> SEQ ID NO 84
<211> LENGTH: 40
<212> TYPE: RNA
<213> ORGANISM: Artificial
<220> FEATURE:
<223> OTHER INFORMATION: RbAmCyan variant mRNA sequence

<400> SEQUENCE: 84
caccauggcc gccguuaucg caaaaucauc aguaucagcu                       40

<210> SEQ ID NO 85
<211> LENGTH: 40
<212> TYPE: RNA
<213> ORGANISM: Artificial
<220> FEATURE:
<223> OTHER INFORMATION: RbAmCyan variant optimized for corn codon usage
      sequence

<400> SEQUENCE: 85
caccauggcu gcugucaucg cuaagucuag cgugucagca                       40

<210> SEQ ID NO 86
<211> LENGTH: 40
<212> TYPE: RNA
<213> ORGANISM: Artificial
<220> FEATURE:
<223> OTHER INFORMATION: RbAmCyan variant optimized for corn codon usage
      sequence

<400> SEQUENCE: 86
caccauggca gcugugauug caaagucauc aguuagcgca                       40

<210> SEQ ID NO 87
<211> LENGTH: 40
<212> TYPE: RNA
<213> ORGANISM: Artificial
<220> FEATURE:
<223> OTHER INFORMATION: RbAmCyan variant optimized for corn codon usage
``` sequence

<400> SEQUENCE: 87
caccauggca gcaguuauug caaaaagcuc ugugagcgca                              40

<210> SEQ ID NO 88
<211> LENGTH: 40
<212> TYPE: RNA
<213> ORGANISM: Artificial
<220> FEATURE:
<223> OTHER INFORMATION: RbAmCyan variant optimized for corn codon usage
      sequence

<400> SEQUENCE: 88
caccauggcu gcaguuauag caaaaagcuc aguguccgcu                              40

<210> SEQ ID NO 89
<211> LENGTH: 40
<212> TYPE: RNA
<213> ORGANISM: Artificial
<220> FEATURE:
<223> OTHER INFORMATION: RbAmCyan variant optimized for corn codon usage
      sequence

<400> SEQUENCE: 89
caccauggcu gcagucaucg caaaaucuuc aguuuccgca                              40

<210> SEQ ID NO 90
<211> LENGTH: 40
<212> TYPE: RNA
<213> ORGANISM: Artificial
<220> FEATURE:
<223> OTHER INFORMATION: RbAmCyan variant optimized for corn codon usage
      sequence

<400> SEQUENCE: 90
caccauggcc gcaguuaucg caaaaucauc agucucagca                              40

<210> SEQ ID NO 91
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 91
caccauggcc gccguaaucg ccaaaagcag cguaagcgcc                              40

<210> SEQ ID NO 92
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 92
caccauggcc gccguaaucg ccaaauccag cguaagcgcc                              40

<210> SEQ ID NO 93
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 93

```
caccauggcc gccgucauag ccaaaagcuc cguaagcgcc            40
```

<210> SEQ ID NO 94
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 94

```
caccauggcc gccguaaucg ccaaaagcuc cguaagcgcc            40
```

<210> SEQ ID NO 95
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 95

```
caccauggcc gccgucauag ccaagagcuc cgucuccgcc            40
```

<210> SEQ ID NO 96
<211> LENGTH: 40
<212> TYPE: RNA
<213> ORGANISM: Artificial
<220> FEATURE:
<223> OTHER INFORMATION: RbAmCyan variant with tobacco rare codons

<400> SEQUENCE: 96

```
caccauggcc gccguaauag ccaaaagcuc cgucuccgcc            40
```

<210> SEQ ID NO 97
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 97

```
aaccauggca gcauuaggaa caaaaggggg agcaggaacc            40
```

<210> SEQ ID NO 98
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 98

```
aaccauggca gcaaucggaa caaaagcagg aggagguacu            40
```

<210> SEQ ID NO 99
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 99

```
aaccauggca gcauaggaa caaaggcagg agcaggcagu             40
```

<210> SEQ ID NO 100

-continued

```
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 100
aaccauggca gcaauuggau caaaagcagg agcaggaacc                          40

<210> SEQ ID NO 101
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 101
aaccauggca gcauuaggua caagaggagc agcaggcacu                          40

<210> SEQ ID NO 102
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 102
aaccauggca gcaauaggua guagagcagc agcaggcaca                          40

<210> SEQ ID NO 103
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 103
aaccauggca gcuauggcaa cuaaagcagc agcaggcaca                          40

<210> SEQ ID NO 104
<211> LENGTH: 40
<212> TYPE: RNA
<213> ORGANISM: Artificial
<220> FEATURE:
<223> OTHER INFORMATION: RbAmCyan variant with mutation for EPSPS and
      excluding tobacco rare codons sequence

<400> SEQUENCE: 104
aaccauggcu gcuauggcua cuaaggcugc ugcuggaacu                          40

<210> SEQ ID NO 105
<211> LENGTH: 64
<212> TYPE: PRT
<213> ORGANISM: Artificial
<220> FEATURE:
<223> OTHER INFORMATION: Organelle targeting peptide sequence

<400> SEQUENCE: 105

Met Ala Phe Val Ala Ser Val Pro Val Phe Ala Asn Ala Ser Gly Leu
1               5                   10                  15

Lys Thr Glu Ala Lys Val Cys Gln Lys Pro Ala Leu Lys Asn Ser Phe
            20                  25                  30
```

-continued

Phe Arg Gly Glu Glu Val Thr Ser Arg Ser Phe Ala Ser Gln Ala
            35                  40                  45

Val Ser Ala Lys Pro Ala Thr Thr Gly Glu Val Asp Thr Thr Ile Arg
 50                  55                  60

<210> SEQ ID NO 106
<211> LENGTH: 34
<212> TYPE: PRT
<213> ORGANISM: Artificial
<220> FEATURE:
<223> OTHER INFORMATION: Organelle targeting peptide sequence

<400> SEQUENCE: 106

Met Asn Lys Ile Leu Gly Ile Asp Pro Leu Lys Lys Pro Ile Phe Gly
 1               5                  10                  15

Ile Ser Ala Phe Val Leu Leu Phe Trp Gln Leu Asn Val Gly Ala Ala
            20                  25                  30

Asn Ala

<210> SEQ ID NO 107
<211> LENGTH: 35
<212> TYPE: PRT
<213> ORGANISM: Artificial
<220> FEATURE:
<223> OTHER INFORMATION: Organelle targeting peptide sequence

<400> SEQUENCE: 107

Met Phe Lys Leu Phe Asn Gln Ala Ser Arg Ile Phe Gly Ile Ala
 1               5                  10                  15

Leu Pro Cys Leu Ile Phe Leu Gly Gly Ile Phe Ser Leu Gly Asn Thr
            20                  25                  30

Ala Leu Ala
        35

<210> SEQ ID NO 108
<211> LENGTH: 23
<212> TYPE: PRT
<213> ORGANISM: Artificial
<220> FEATURE:
<223> OTHER INFORMATION: Organelle targeting peptide sequence

<400> SEQUENCE: 108

Met Lys His Leu Leu Ala Leu Leu Ala Phe Thr Leu Trp Phe Asn
 1               5                  10                  15

Phe Ala Pro Ser Ala Ser Ala
            20

<210> SEQ ID NO 109
<211> LENGTH: 30
<212> TYPE: PRT
<213> ORGANISM: Artificial
<220> FEATURE:
<223> OTHER INFORMATION: Organelle targeting peptide sequence

<400> SEQUENCE: 109

Met Ala Leu Val Ala Arg Pro Val Leu Ser Ala Arg Val Ala Ala Ser
 1               5                  10                  15

Arg Pro Arg Val Ala Ala Arg Lys Ala Val Arg Val Ser Ala
            20                  25                  30

<210> SEQ ID NO 110
<211> LENGTH: 24
<212> TYPE: PRT

```
<213> ORGANISM: Artificial
<220> FEATURE:
<223> OTHER INFORMATION: Organelle targeting peptide sequence

<400> SEQUENCE: 110

Met Gln Ala Leu Ser Ser Arg Val Asn Ile Ala Ala Lys Pro Gln Arg
1               5                   10                  15

Ala Gln Arg Leu Val Val Arg Ala
            20

<210> SEQ ID NO 111
<211> LENGTH: 30
<212> TYPE: PRT
<213> ORGANISM: Artificial
<220> FEATURE:
<223> OTHER INFORMATION: Organelle targeting peptide sequence

<400> SEQUENCE: 111

Met Gln Thr Leu Ala Ser Arg Pro Ser Leu Arg Ala Ser Ala Arg Val
1               5                   10                  15

Ala Pro Arg Arg Ala Pro Arg Val Ala Val Val Thr Lys Ala
            20                  25                  30

<210> SEQ ID NO 112
<211> LENGTH: 26
<212> TYPE: PRT
<213> ORGANISM: Artificial
<220> FEATURE:
<223> OTHER INFORMATION: Organelle targeting peptide sequence

<400> SEQUENCE: 112

Met Gln Ala Leu Ala Thr Arg Pro Ser Ala Ile Arg Pro Thr Lys Ala
1               5                   10                  15

Ala Arg Arg Ser Ser Val Val Val Arg Ala
            20                  25

<210> SEQ ID NO 113
<211> LENGTH: 45
<212> TYPE: PRT
<213> ORGANISM: Artificial
<220> FEATURE:
<223> OTHER INFORMATION: Organelle targeting peptide sequence

<400> SEQUENCE: 113

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln
        35                  40                  45

<210> SEQ ID NO 114
<211> LENGTH: 35
<212> TYPE: PRT
<213> ORGANISM: Artificial
<220> FEATURE:
<223> OTHER INFORMATION: Organelle targeting peptide sequence

<400> SEQUENCE: 114

Met Ala Ala Met Leu Ala Ser Lys Gln Gly Ala Phe Met Gly Arg Ser
1               5                   10                  15

Ser Phe Ala Pro Ala Pro Lys Gly Val Ala Ser Arg Gly Ser Leu Gln
            20                  25                  30
```

Val Val Ala
        35

<210> SEQ ID NO 115
<211> LENGTH: 37
<212> TYPE: PRT
<213> ORGANISM: Artificial
<220> FEATURE:
<223> OTHER INFORMATION: Organelle targeting peptide sequence

<400> SEQUENCE: 115

Met Ala Ala Phe Val Ala Ala Leu Pro Val Ile Pro Ser Lys Ala Phe
1               5                   10                  15

Ile Ala Gly Lys Ala Asp Val Ala Lys Ala Pro Val Ala Thr Asn Lys
            20                  25                  30

Gly Gly Val Arg Met
        35

<210> SEQ ID NO 116
<211> LENGTH: 80
<212> TYPE: PRT
<213> ORGANISM: Artificial
<220> FEATURE:
<223> OTHER INFORMATION: Organelle targeting peptide sequence

<400> SEQUENCE: 116

Met Leu Ala Arg Gln Gly Gly Ser Leu Arg Ala Ser Gln Cys Asn Ala
1               5                   10                  15

Gly Leu Ala Arg Arg Val Glu Val Gly Ala Leu Val Val Pro Arg Pro
            20                  25                  30

Ile Ser Val Asn Asp Val Val Pro His Val Tyr Ser Ala Pro Leu Ser
        35                  40                  45

Val Ala Arg Arg Ser Cys Ser Lys Ser Ser Ile Arg Ser Thr Arg Arg
    50                  55                  60

Leu Gln Thr Thr Val Cys Ser Ala Thr Leu Ala Ala His Ser Ala Pro
65                  70                  75                  80

<210> SEQ ID NO 117
<211> LENGTH: 124
<212> TYPE: PRT
<213> ORGANISM: Artificial
<220> FEATURE:
<223> OTHER INFORMATION: Optimized chloroplast targeting peptide
      sequence

<400> SEQUENCE: 117

Met Ala Ser Ile Ser Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

```
Leu Gly Asn Val Ser Asn Gly Gly Arg Ile Arg Cys
            115                 120
```

<210> SEQ ID NO 118
<211> LENGTH: 18
<212> TYPE: PRT
<213> ORGANISM: Artificial
<220> FEATURE:
<223> OTHER INFORMATION: Organelle targeting peptide sequence

<400> SEQUENCE: 118

```
Met Arg Val Leu Leu Val Ala Leu Ala Leu Leu Ala Leu Ala Ala Ser
1               5                   10                  15

Ala Thr
```

<210> SEQ ID NO 119
<211> LENGTH: 29
<212> TYPE: PRT
<213> ORGANISM: Artificial
<220> FEATURE:
<223> OTHER INFORMATION: Organelle targeting peptide sequence

<400> SEQUENCE: 119

```
Met Met Ser Phe Val Ser Leu Leu Leu Val Gly Ile Leu Phe Trp Ala
1               5                   10                  15

Thr Glu Ala Glu Gln Leu Thr Lys Cys Glu Val Phe Gln
            20                  25
```

<210> SEQ ID NO 120
<211> LENGTH: 9
<212> TYPE: PRT
<213> ORGANISM: Artificial
<220> FEATURE:
<223> OTHER INFORMATION: Organelle targeting peptide sequence
<220> FEATURE:
<221> NAME/KEY: misc_feature
<222> LOCATION: (3)..(7)
<223> OTHER INFORMATION: Xaa can be any naturally occurring amino acid

<400> SEQUENCE: 120

```
Arg Leu Xaa Xaa Xaa Xaa Xaa His Leu
1               5
```

<210> SEQ ID NO 121
<211> LENGTH: 25
<212> TYPE: PRT
<213> ORGANISM: Artificial
<220> FEATURE:
<223> OTHER INFORMATION: Organelle targeting peptide sequence

<400> SEQUENCE: 121

```
Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25
```

<210> SEQ ID NO 122
<211> LENGTH: 23
<212> TYPE: PRT
<213> ORGANISM: Artificial
<220> FEATURE:
<223> OTHER INFORMATION: Organelle targeting peptide sequence

<400> SEQUENCE: 122

```
Met Leu Arg Ile Pro Val Arg Lys Ala Leu Val Gly Leu Ser Lys Ser
1               5                   10                  15
```

Ser Lys Gly Cys Val Arg Thr
            20

<210> SEQ ID NO 123
<211> LENGTH: 30
<212> TYPE: PRT
<213> ORGANISM: Artificial
<220> FEATURE:
<223> OTHER INFORMATION: Organelle targeting peptide sequence

<400> SEQUENCE: 123

Met Ala Leu Arg Thr Leu Ala Ser Lys Lys Val Leu Ser Phe Pro Phe
1               5                   10                  15

Gly Gly Ala Gly Arg Pro Leu Ala Ala Ala Ala Ser Ala Arg
            20                  25                  30

<210> SEQ ID NO 124
<211> LENGTH: 33
<212> TYPE: PRT
<213> ORGANISM: Artificial
<220> FEATURE:
<223> OTHER INFORMATION: Organelle targeting peptide sequence

<400> SEQUENCE: 124

Met Ala Tyr Arg Ala Ala Ala Ser Leu Ala Ser Lys Ala Arg Gln Ala
1               5                   10                  15

Gly Asn Ser Leu Ala Thr Arg Gln Val Gly Ser Arg Leu Ala Trp Ser
            20                  25                  30

Arg

<210> SEQ ID NO 125
<211> LENGTH: 37
<212> TYPE: PRT
<213> ORGANISM: Artificial
<220> FEATURE:
<223> OTHER INFORMATION: Organelle targeting peptide sequence

<400> SEQUENCE: 125

Met Lys Ala Phe Thr Leu Ala Leu Phe Leu Ala Leu Ser Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala
            35

<210> SEQ ID NO 126
<211> LENGTH: 21
<212> TYPE: PRT
<213> ORGANISM: Artificial
<220> FEATURE:
<223> OTHER INFORMATION: Organelle targeting peptide sequence

<400> SEQUENCE: 126

Met Gln Leu Ser Glu Ser Glu Met Arg Phe Arg Asp Arg Gln Cys Gln
1               5                   10                  15

Arg Glu Val Gln Asp
            20